United States Patent
Karsunky et al.

(10) Patent No.: US 9,631,026 B2
(45) Date of Patent: *Apr. 25, 2017

(54) ANTIBODIES THAT SPECIFICALLY BIND TO TIM3

(71) Applicant: Cellerant Therapeutics, Inc., San Carlos, CA (US)

(72) Inventors: Holger Karsunky, Redwood City, CA (US); Ying-Ping Jiang, Lafayette, CA (US)

(73) Assignee: Cellerant Therapeutics, Inc., San Carlos, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/458,053

(22) Filed: Aug. 12, 2014

(65) Prior Publication Data

US 2015/0086574 A1    Mar. 26, 2015

Related U.S. Application Data

(63) Continuation of application No. 13/538,778, filed on Jun. 29, 2012, now Pat. No. 8,841,418.

(60) Provisional application No. 61/660,530, filed on Jun. 15, 2012, provisional application No. 61/504,062, filed on Jul. 1, 2011.

(51) Int. Cl.
| | |
|---|---|
| *C07K 16/30* | (2006.01) |
| *C07K 16/28* | (2006.01) |
| *G01N 33/50* | (2006.01) |
| *G01N 33/574* | (2006.01) |
| *A61K 31/337* | (2006.01) |
| *A61K 31/4545* | (2006.01) |
| *A61K 31/704* | (2006.01) |
| *A61K 31/24* | (2006.01) |
| *A61K 38/16* | (2006.01) |
| *A61K 47/48* | (2006.01) |

(52) U.S. Cl.
CPC ......... *C07K 16/3092* (2013.01); *A61K 31/24* (2013.01); *A61K 31/337* (2013.01); *A61K 31/4545* (2013.01); *A61K 31/704* (2013.01); *A61K 38/168* (2013.01); *A61K 47/48561* (2013.01); *C07K 16/2803* (2013.01); *C07K 16/30* (2013.01); *C07K 16/3061* (2013.01); *G01N 33/5047* (2013.01); *G01N 33/5073* (2013.01); *G01N 33/57407* (2013.01); *G01N 33/57426* (2013.01); *C07K 2317/565* (2013.01); *C07K 2317/73* (2013.01); *C07K 2317/734* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 8,841,418 B2* | 9/2014 | Karsunky | C07K 16/2803 530/387.1 |
| 2003/0099655 A1 | 5/2003 | Watkins et al. | |
| 2006/0073145 A1 | 4/2006 | Leturcq et al. | |
| 2008/0199851 A1 | 8/2008 | Egan et al. | |
| 2009/0041783 A1 | 2/2009 | Takayama et al. | |
| 2009/0092614 A1* | 4/2009 | Demarest | C07K 16/2863 424/139.1 |
| 2009/0111687 A1 | 4/2009 | Gabriel et al. | |
| 2009/0208491 A1 | 8/2009 | Gurney et al. | |
| 2009/0304590 A1 | 12/2009 | Gill et al. | |
| 2010/0061992 A1 | 3/2010 | Anderson et al. | |
| 2010/0233079 A1 | 9/2010 | Jakob et al. | |
| 2011/0015090 A1 | 1/2011 | Majeti et al. | |
| 2011/0044894 A1 | 2/2011 | Karsunky | |
| 2012/0100131 A1 | 4/2012 | Takayanagi et al. | |
| 2012/0189617 A1 | 7/2012 | Takayanagi et al. | |

FOREIGN PATENT DOCUMENTS

| | | |
|---|---|---|
| WO | 96/23067 A1 | 8/1996 |
| WO | 2009/091547 A1 | 7/2009 |
| WO | 2010/078526 A1 | 7/2010 |

OTHER PUBLICATIONS

Anderson et al.; "Promotion of tissue inflammation by the immune receptor Tim-3 expressed on innate immune cells"; *Science*. 318:1141-1143 (2007).

Belkin et al.; "Killer cell Ig-like receptor and leukocyte Ig-like receptor transgenic mice exhibit tissue- and cell-specific transgene expression"; *J. Immunol*. 171(6):3056-3063 (Sep. 2003).

Bennett et al.; "The myelodysplastic syndromes: Diagnosis, molecular biology and risk assessment"; *Hematology*. 10(Suppl 1):258-269 (2005).

Dohner et al.; "Diagnosis and management of acute myeloid leukemia in adults: recommendations from an international expert panel, on behalf of the European LeukemiaNet"; *Blood*; 115:453-474 (2010) ePub on Oct. 30, 2009.

Funatsu et al.; "Characterization of a Novel Rat Brain Glycosylphosphatidylinositol-anchored Protein (Kilon), a Member of the IgLON Cell Adhesion Molecule Family"; *J. Biol. Chem.*; 274(12):8224-8230 (Mar. 1999).

Gal, H. et al.; "Gene expression profiles of AML derived stem cells: similarity to hematopoietic stem cells"; 2006, *Leukemia*, vol. 20, No. 12, pp. 2147-2154.

Hadidi et al.; "Preparation and functional properties of polyclonal and monoclonal antibodies to murine MD-1"; *Immunol. Lett.*; 77(2):97-103 (Jun. 2001).

Huang et al.; "Lymphoma endothelium preferentially express Tim-3 and facilitates the progression of lymphoma by mediating immune evasion"; *J. Exp. Med.*; 207(3):505-520 (2010) ePub Feb. 22, 2010.

(Continued)

*Primary Examiner* — Brad Duffy
*Assistant Examiner* — Nelson B Moseley, II
(74) *Attorney, Agent, or Firm* — Kilpatrick Townsend & Stockton LLP

(57) ABSTRACT

Provided herein are antibodies specific for TIM3 that can be used to detect cancer cells, in particular, cancer stem cells. The antibodies can also be used in therapeutic compositions for treating cancer and reducing inflammation.

12 Claims, 10 Drawing Sheets

(56) References Cited

OTHER PUBLICATIONS

Jan et al.; "Prospective separation of normal and leukemic stem cells based upon differential expression of TIM3, a human acute myeloid leukemia stem cell marker"; Proc. Natl. Acad. Sci. USA; 108(12):5009-25014 (2011).

Kikushige et al.; "TIM-3 as a therapeutic target for malignant stem cells in acute myelogenous leukemia"; *Ann. N.Y. Acad. Sci.*; 1266:118-123 (2012).

Kikushige et al.; "TIM-3 Is a Promising Target to Selectively Kill Acute Myeloid Leukemia Stem Cells"; *Cell Stem Cell*; 7:708-717. (Dec. 2010).

Krause et al.; "Characterization of MAX.3 antigen, a glycoprotein expressed on mature macrophages, dendritic cells and blood platelets : identity with CD84"; *Biochem. J.*; 346:729-736 (Mar. 2000).

Legare, R.D. et al.; "CBFA2, frequently rearranged in leukemia, is not responsible leukemia for a familial leukemia syndrome"; 1997, *Leukemia*, vol. 11, No. 12, pp. 2111-2119.

Miura et al.; "RP105 is associated with MD-1 and transmits an activation signal in human B cells"; *Blood*: 92(8):2815-2822 (Oct. 1998).

Nakajima et al.; "Cutting Edge: Human Myeloid Cells Express an Activating ILT Receptor (ILT1) That Associates with Fc Receptor γ-Chain"; *J. Immunol.*; 162(1):5-8 (Jan. 1999).

Nakayama et al.; "Tim-3 mediates phagocytosis of apoptotic cells and cross-presentation"; *Blood*; 113:3821-3830 (2009).

Schmitt et al.; "Quantitative expression of Toll-like receptor-2, -4, and -9 in dendritic cells generated from blasts of patients with acute myeloid leukemia"; *Transfusion*; 48(5):861-870 (Jan. 2008).

Sui et al.; "Human membrane protein Tim-3 facilitates hepatitis A virus entry into target cells"; *Int. J. Mol. Med.*; 17(6):1093-1099 (Jun. 2006).

Tefferi et al.; "Myeloproliferative neoplasms: contemporary diagnosis using histology and genetics"; *Nat. Rev. Clin. Oncol.*; 6:627-637 (2009).

Office Action from U.S. Appl. No. 12/810,006 dated Jan. 28, 2013.

Office Action from U.S. Appl. No. 12/810,006 dated May 17, 2012.

U.S. Appl. No. 12/810,006, filed Sep. 13, 2010 (73 pages).

Hastings, et al. "TIM-3 is expressed on activated human CD4+ T Cells and regulates Th1 and Th17 cytokines." *European Journal Immunology*; Sep. 2009 vol. 39.

PCT Search Report and Written Opinion mailed Jan. 24, 2013. This is the PCT Search Report and Written Opinion for WO 2013/006490, international publication date: Jan. 10, 2013. NBM II Feb. 17, 2017.

* cited by examiner

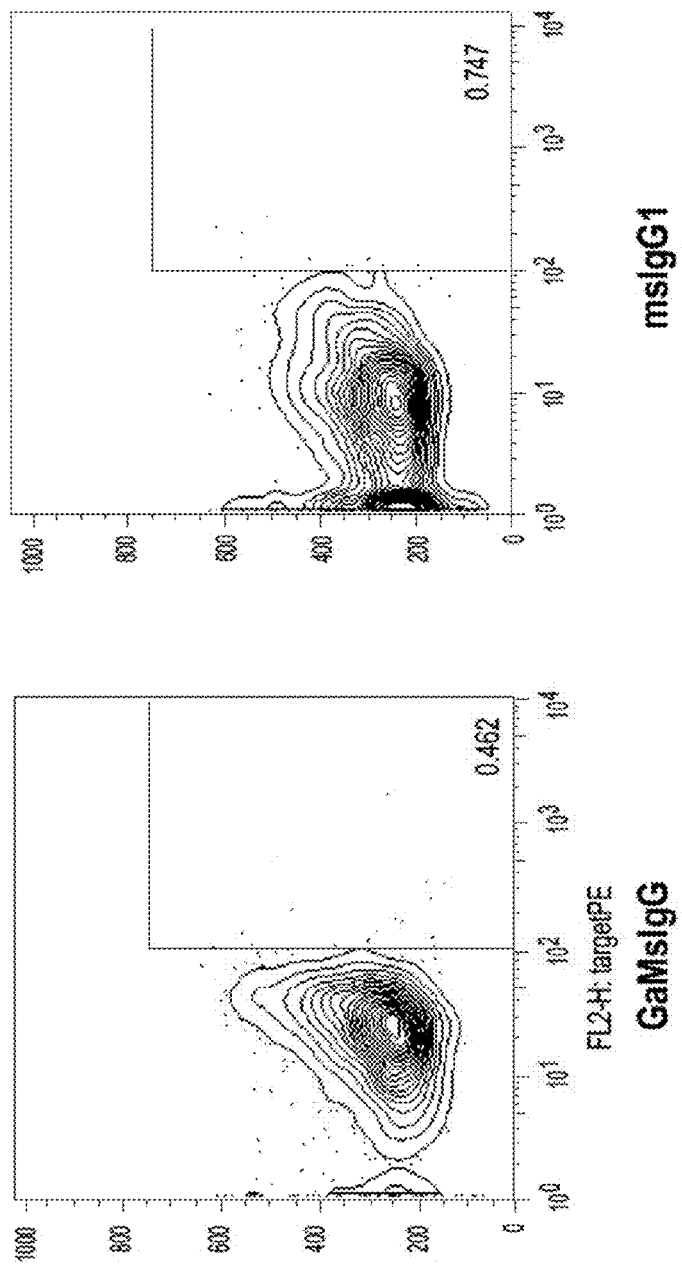
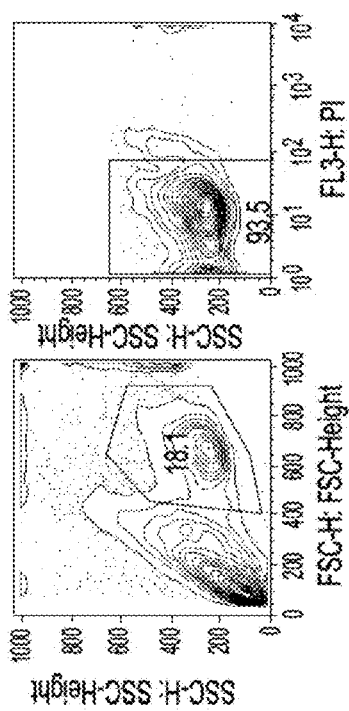
FIG. 2 (CONT.)

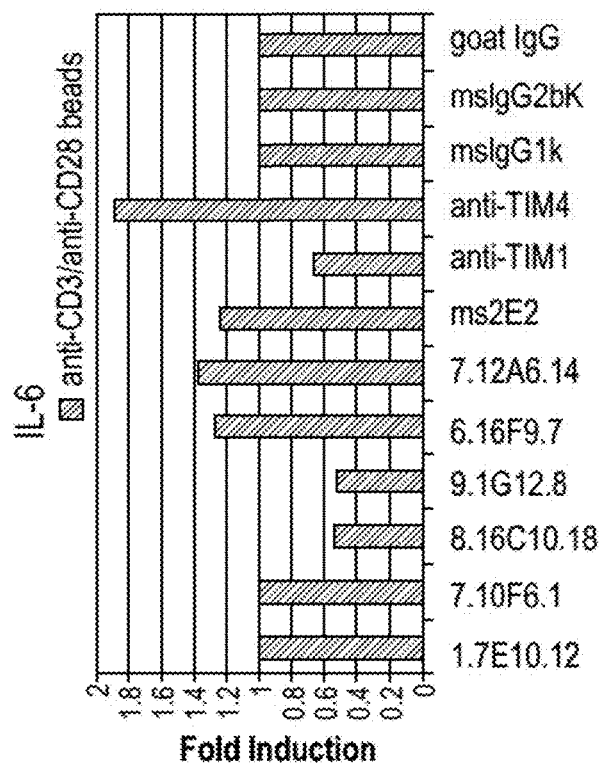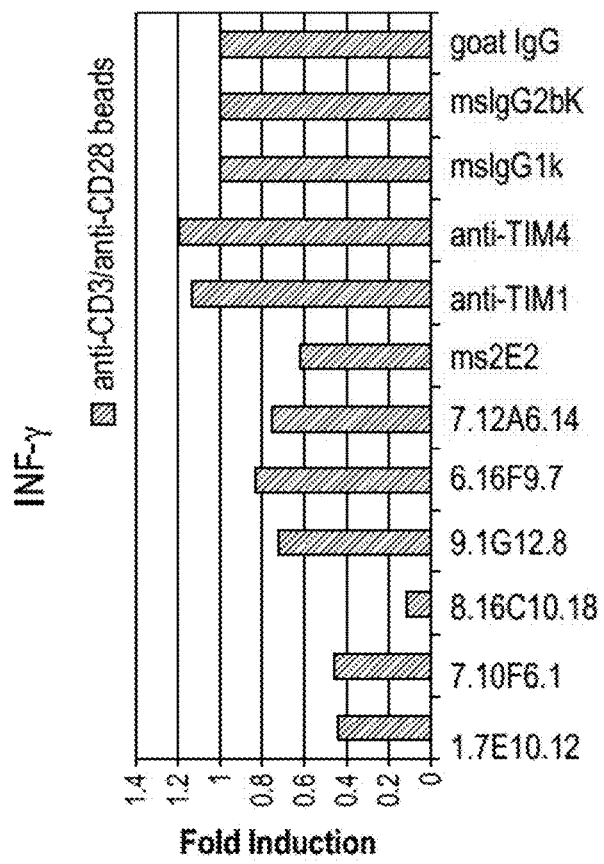
FIG. 7

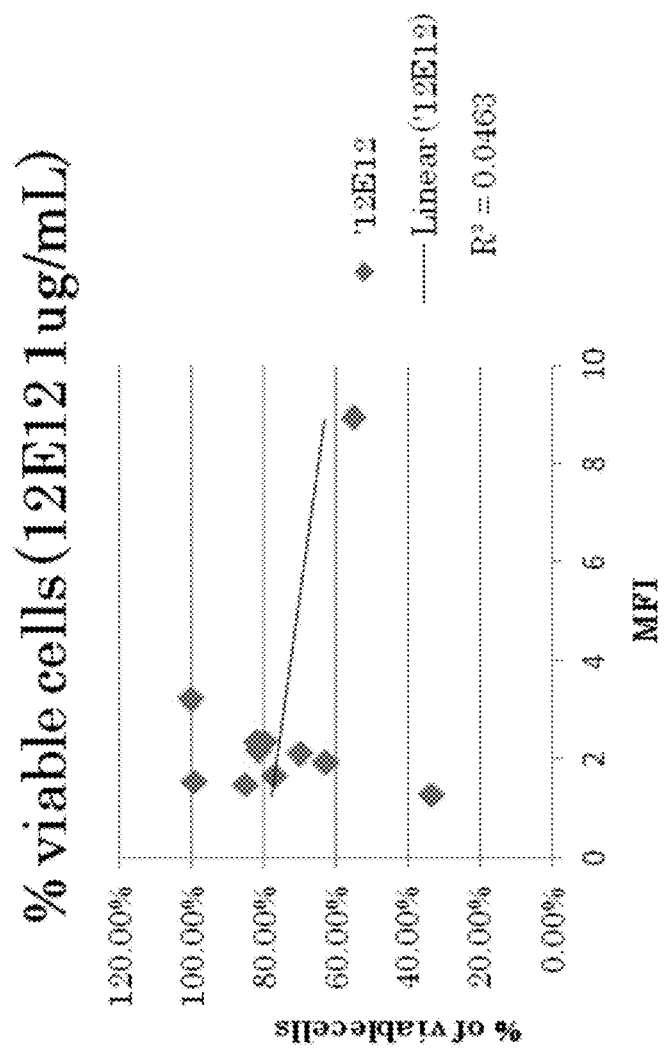

US 9,631,026 B2

ANTIBODIES THAT SPECIFICALLY BIND TO TIM3

CROSS-REFERENCES TO RELATED APPLICATIONS

The present application is a continuation of U.S. application Ser. No. 13/538,778, filed Jun. 29, 2012, which claims priority to U.S. Provisional Application No. 61/504,062, filed Jul. 1, 2011, and U.S. Provisional Application No. 61/660,530, filed Jun. 15, 2012, the disclosures of which are incorporated herein by reference in their entireties.

REFERENCE TO A SEQUENCE LISTING SUBMITTED AS A TEXT FILE

The Sequence Listing written in file SEQTXT_92950-913640.txt, created on Aug. 11, 2014, 77,707 bytes, machine format IBM-PC, MS-Windows operating system, is hereby incorporated by reference in its entirety for all purposes.

BACKGROUND OF THE INVENTION

T cell immunoglobulin and mucin domain-containing molecule 3 (TIM3) is an immunoglobulin (Ig) superfamily member, expressed on Th1 cells. TIM3 has been shown to play a role in modulating the immune response of Th1 cells, and reducing inflammation in a number of conditions.

TIM3 is also expressed on cancer cells, and on cancer stem cells (CSCs), which are cells that can give rise to additional cancer cells.

One of the major limitations of chemotherapy is the general inability of anticancer drugs to discriminate between normal and cancer cells. Almost all members of the major categories of antineoplastic agents have considerable toxicity for normal cells.

Compositions that specifically target cancer cells can avoid this problem. However, existing cancer targets do not target CSCs. For this reason, existing chemotherapeutic strategies, even when specifically delivered to cancer cells, do not effectively eliminate the cancer. Risk of recurrence remains because the surviving CSCs can give rise to new cancer cells.

Provided herein are anti-TIM3 antibodies that are rapidly internalized into TIM3 expressing cells. These antibodies provide novel diagnostic and therapeutic strategies for targeting TIM3-associated disorders.

BRIEF SUMMARY OF THE INVENTION

Provided herein are TIM3-specific antibodies with improved properties, e.g., for targeting cancer cells, reducing cancer cell growth, and reducing inflammation due to CD4 T cells. In some embodiments, the invention provides an isolated antibody that specifically binds the extracellular domain of TIM3 (a TIM3-specific antibody), wherein said binding results in internalization into a TIM3-expressing cell. In some embodiments, the TIM3-specific antibody is linked to a cytotoxic agent. In some embodiments, the cytotoxic agent is selected from saporin, a taxane, a vinca alkaloid, an anthracycline, and cisplatin.

In some embodiments, the TIM3-expressing cell (in which the TIM3-specific antibody is internalized) is a cancer stem cell (CSC). In some embodiments, the TIM3-expressing cell is a hematopoietic cancer cell, e.g., a lymphoma such as a B cell lymophoma, T cell lymphoma, Burkitt's lymphoma, Hodgkin's lymphoma, or non-Hodgkin's lymphoma. In some embodiments, the hematopoietic cancer cell is from a leukemia or myeloma, e.g., acute myelogenous leukemia (AML), acute lymphoblastic leukemia (ALL), chronic myelogenous leukemia (CML), chronic lymphoblastic leukemia (CLL), Chronic Myelomonocytic Leukemia (CMML), Myelodysplastic Syndrome (MDS), etc. In some embodiments, the TIM3-expressing cell is a solid tumor cell from, e.g., colon cancer, ovarian cancer, liver cancer, prostate cancer, uterine cancer, breast cancer, or renal cancer.

In some embodiments, at least 50% of the TIM3-specific antibody is internalized in 20 minutes in appropriate conditions as described herein (e.g., at appropriate temperature (e.g., 20-37 C), accounting for antibody concentration relative to cell numbers, etc.). In some embodiments, the TIM3-specific antibody is internalized at a higher rate than the 2E2 antibody.

In some embodiments, the internalizing TIM3-specific antibody can bind a TIM3-expressing cell, wherein said binding inhibits proliferation of the TIM3-expressing cell. In some embodiments, the internalizing TIM3-specific antibody binds a higher percentage of peripheral blood mononuclear cells (PBMCs) from an individual having a hematopoietic cell cancer than the anti-TIM3 antibody 2E2. In some embodiments, the internalizing TIM3-specific antibody can mediate complement dependent cytotoxicity (CDC), e.g., such that more than 10, 20, 30, 40, 50% or higher percentage of TIM3 expressing cells in a sample are killed by CDC within 1 hour under appropriate conditions as described herein (e.g., with functional complement proteins, at appropriate temperature, accounting for antibody concentration relative to amount of complement and cell numbers, etc.). In some embodiments, the internalizing TIM3-specific antibody does not mediate CDC, e.g., less than 10% of TIM3 expressing cells in a sample are killed by CDC within 1 hour under appropriate conditions. In some embodiments, the internalizing TIM3-specific antibody can inhibit release of an inflammatory cytokine from an activated CD4+ T cell, compared to the release of the inflammatory cytokine in the absence of the antibody.

In some embodiments, the internalizing TIM3-specific antibody competes for binding with a competitor antibody selected from the group consisting of:

an antibody having light chain complementarity determining region (CDR) sequences of SEQ ID NOs:8-10 and heavy chain CDR sequences of SEQ ID NOs:3-5 (1.7E10);

an antibody having light chain CDR sequences of SEQ ID NOs:18-20 and heavy chain CDR sequences of SEQ ID NOs:13-15 (7.10F6);

an antibody having light chain CDR sequences of SEQ ID NOs:28-30 and heavy chain CDR sequences of SEQ ID NOs:23-25 (8.16C10);

an antibody having light chain CDR sequences of SEQ ID NOs:108-110 and heavy chain CDR sequences of SEQ ID NOs:103-105 (27.12E12); and an antibody having light chain CDR sequences of SEQ ID NOs:118-120 and heavy chain CDR sequences of SEQ ID NOs: 113-115 (9.1G12).

In some embodiments, the internalizing TIM3-specific antibody is selected from the group consisting of the above competitor antibodies. In some embodiments, the internalizing TIM3-specific antibody comprises the heavy and light chain CDR sequences of 1.7E10. In some embodiments, the internalizing TIM3-specific antibody comprises the heavy and light chain CDR sequences of 7.10F6. In some embodiments, the internalizing TIM3-specific antibody comprises the heavy and light chain CDR sequences of 8.16C10. In some embodiments, the internalizing TIM3-specific antibody comprises the heavy and light chain CDR sequences of 27.12E12. In some embodiments, the internalizing TIM3-specific antibody comprises the heavy and light chain CDR sequences of 9.1G12.

In some embodiments, the internalizing TIM3-specific antibody is selected from the group consisting of:
- an antibody having a light chain variable region sequence comprising SEQ ID NO:7 and a heavy chain variable region sequence of SEQ ID NO:2 (1.7E10);
- an antibody having a light chain variable region sequence comprising SEQ ID NO:17 and a heavy chain variable region sequence comprising SEQ ID NO:12 (7.10F6);
- an antibody having a light chain variable region sequence comprising SEQ ID NO:27 and a heavy chain variable region sequence comprising SEQ ID NO:22 (8.16C10);
- an antibody having a light chain variable region sequence comprising SEQ ID NO:107 and a heavy chain variable region sequence comprising SEQ ID NO:102 (27.12E12); and
- an antibody having a light chain variable region sequence comprising SEQ ID NOs:117 and a heavy chain variable region sequence comprising SEQ ID NO:112 (9.1G12).

Internalizing TIM3-specific antibodies can be used in methods of treating cancer, including but not limited to killing cancer cells using the internalizing TIM3-specific antibody linked to a cytotoxic agent. The internalizing TIM3-specific antibody can be formulated in a pharmaceutical composition. In some embodiments, the method comprises contacting a TIM3 expressing cancer cell with the internalizing TIM3-specific antibody. In some embodiments, the TIM3 expressing cancer cell is a hematopoietic cancer cell (e.g., lymphoma, leukemia, myeloma, and subsets thereof described herein). In some embodiments the TIM3 expressing cancer cell is a cancer stem cell. In some embodiments, the TIM3 expressing cancer cell is from a solid tumor, including but not limited to cells from colon cancer, ovarian cancer, liver cancer, prostate cancer, uterine cancer, breast cancer, and kidney cancer. In some embodiments, the contacting comprises administering the internalizing TIM3-specific antibody to an individual having a TIM3-expressing cancer as described herein.

Further provided are TIM3-specific antibodies that specifically bind to the extracellular domain of TIM3 and inhibit proliferation of TIM3-expressing cells upon binding, e.g., compared to proliferation in the absence of the antibody. In some embodiments, the proliferation inhibiting TIM3-specific antibody (or TIM3-binding portion thereof) is cross-linked, e.g., to a solid or semisolid matrix (e.g., a bead). In some embodiments, the proliferation inhibiting TIM3-specific antibody (or TIM3-binding portion thereof) is multimerized, e.g., linked to each other, in a multivalent antibody, or multivalent antibody isotype (e.g., IgM or IgA).

In some embodiments, the TIM3 expressing cancer cell is a hematopoietic cancer cell (e.g., lymphoma, leukemia, myeloma, and subsets thereof described herein). In some embodiments, the TIM3 expressing cancer cell is a cancer stem cell. In some embodiments, the TIM3 expressing cancer cell is from a solid tumor, e.g., selected from the group consisting of colon cancer, ovarian cancer, liver cancer, prostate cancer, uterine cancer, breast cancer, and kidney cancer.

In some embodiments, the proliferation inhibiting TIM3-specific antibody is selected from the group consisting of:
- an antibody comprising the CDR sequences of 1.7E10 (CDRH1-3=SEQ ID NOs:3-5; CDRL1-3=SEQ ID NOs:8-10); and
- an antibody comprising the CDR sequences of 7.10F6 (CDRH1-3=SEQ ID NOs:13-15; CDRL1-3=SEQ ID NOs:18-20).

In some embodiments, the proliferation inhibiting TIM3-specific antibody is selected from the group consisting of:
- an antibody comprising variable region sequences of 1.7E10 (Vl=SEQ ID NO: 7; Vh=SEQ ID NO:2); and
- an antibody having variable region sequences of 7.10F6 (Vl=SEQ ID NO:17; Vh=SEQ ID NO:12).

In some embodiments, the proliferation inhibiting TIM3-specific antibody is conjugated to (linked to) a cytotoxic agent. In some embodiments, the proliferation inhibiting TIM3-specific antibody is not linked to a cytotoxic agent. In some embodiments, the TIM3-specific antibody is conjugated to a detectable agent. In some embodiments, the antibody is formulated into a pharmaceutical composition.

In some embodiments, the proliferation inhibiting TIM3-specific antibodies can be used in methods for treating cancer. In some embodiments, the method comprises contacting a TIM3 expressing cancer cell (e.g., as described above) with the proliferation inhibiting TIM3-specific antibody. In some embodiments, the contacting comprises administering the proliferation inhibiting TIM3-specific antibody to an individual, e.g., an individual having a TIM3-expressing cancer. In some embodiments, the proliferation inhibiting TIM3-specific antibody is cross-linked or multimerized prior to administration.

In some embodiments, the TIM3-specific antibody that reduces (inhibits) TIM3-expressing cell proliferation also is internalized into TIM3-expressing cells. In some embodiments, the TIM3-specific antibody that reduces TIM3-expressing cell proliferation also mediates CDC. In some embodiments, the proliferation inhibiting TIM3-specific antibody does not mediate CDC. In some embodiments, the TIM3-specific antibody that reduces TIM3-expressing cell proliferation also reduces release of an inflammatory cytokine from an activated T cell, e.g., compared to release of the inflammatory cytokine in the absence of the antibody.

In some embodiments, the proliferation inhibiting TIM3-specific antibody binds a higher percentage of PBMCs or BMMCs from an individual having a hematopoietic cell cancer (e.g., AML or B cell lymphoma) than 2E2. For example, the TIM3-specific antibody can bind more than 2%, 5%, 8%, 10%, or higher percentage of PBMCs or BMMCs from an individual having leukemia or lymphoma (e.g., a primary patient sample).

Further provided are antibodies that specifically bind the extracellular domain of TIM3, wherein the antibody binds a high percentage of PBMCs or BMMCs from an individual having a hematopoietic cell cancer with high intensity (e.g., as determined by brighter staining by FACS). In some embodiments, the TIM3-specific antibody binds a higher percentage of PBMCs or BMMCs than the anti-TIM3 antibody 2E2 (and can be referred to as a "high hematopoietic cancer cell binding TIM3-specific antibody"). In some embodiments, the hematopoietic cell cancer is selected from lymphoma (e.g., Burkitt's lymphoma, B cell lymphoma, Hodgkin's lymphoma, non-Hodgkin's lymphoma); leukemia (e.g., an acute or chronic leukemia, or preleukemia such as myelodysplastic syndrome, chronic myelomonocytic leukemia, etc.); and myeloma (e.g., AML, CML, etc.).

In some embodiments, the high hematopoietic cancer cell binding TIM3-specific antibody binds at least 3%, 5%, 8%, 10%, 12%, 15%, 20% or higher % of the PBMCs from the individual. In some embodiments, the high hematopoietic cancer cell binding TIM3-specific antibody is linked to a detectable label. In some embodiments, the high hematopoietic cancer cell binding TIM3-specific antibody is linked to a cytotoxic agent.

In some embodiments, the high hematopoietic cancer cell binding TIM3-specific antibody competes for binding with a competitor antibody selected from:
- an antibody comprising light chain CDR sequences of SEQ ID NOs:8-10 and heavy chain CDR sequences of SEQ ID NOs:3-5 (1.7E10);
- an antibody comprising light chain CDR sequences of SEQ ID NOs:18-20 and heavy chain CDR sequences of SEQ ID NOs:13-15 (7.10F6);
- an antibody comprising light chain CDR sequences of SEQ ID NOs:108-110 and heavy chain CDR sequences of SEQ ID NOs:103-105 (27.12E12); and
- an antibody comprising light chain CDR sequences of SEQ ID NOs:118-120 and heavy chain CDR sequences of SEQ ID NOs: 113-115 (9.1G12).

In some embodiments, the high hematopoietic cancer cell binding TIM3-specific antibody comprises the CDR sequences or the variable region sequences of 1.7E10. In some embodiments, the high hematopoietic cancer cell binding TIM3-specific antibody comprises the CDR sequences or the variable region sequences of 7.10F6. In some embodiments, the high hematopoietic cancer cell binding TIM3-specific antibody comprises the CDR sequences or the variable region sequences of 27.12E12. In some embodiments, the high hematopoietic cancer cell binding TIM3-specific antibody comprises the CDR sequences or variable region sequences of 9.1G12.

The high hematopoietic cancer cell binding TIM3-specific antibodies can be used for diagnosing a hematopoietic cancer in an individual, e.g., where the antibody is linked to a detectable label. In some embodiments, the method of diagnosis can comprise contacting a high hematopoietic cancer cell binding TIM3-specific antibody with a biological sample from an individual, and determining binding of the antibody to cells in the biological sample, wherein binding indicates that the individual has hematopoietic cell cancer. In some embodiments, the sample is blood or a blood fraction. In some embodiments, the method comprises administering a high hematopoietic cancer cell binding TIM3-specific antibody to an individual and determining binding of the antibody to cells in the individual wherein binding indicates that the individual has hematopoietic cell cancer. In this in vivo diagnostic method, the hematopoietic cancer can be also be localized in the individual.

In some embodiments, the method further comprises treating the individual for hematopoietic cell cancer, i.e., where the determining step indicates that the individual has a hematopoietic cell cancer. Thus, in some embodiments, the method further comprises administering a chemotherapeutic agent to the individual. In some embodiments, the chemotherapeutic agent comprises the same high hematopoietic cancer cell binding TIM3-specific antibody that was used for the contacting (detecting) step. In some embodiments, the chemotherapeutic agent comprises a high hematopoietic cancer cell binding TIM3-specific antibody that is not the antibody used for the contacting step. In some embodiments, the chemotherapeutic agent comprises a TIM3-specific antibody that competes for binding to TIM3 with a competitor antibody comprising the CDR sequences of an antibody selected from the group consisting of 1.7E10, 7.10F6, 8.16C10, 27.12E12, and 9.1G12. In some embodiments, the chemotherapeutic agent comprises a TIM-3 specific antibody comprising the CDR sequences of an antibody selected from the group consisting of 1.7E10, 7.10F6, 8.16C10, 27.12E12, and 9.1G12. In some embodiments, the chemotherapeutic agent comprises a TIM3-specific antibody comprising the variable region sequences of an antibody selected from the group consisting of 1.7E10, 7.10F6, 8.16C10, 27.12E12, and 9.1G12. In some embodiments, the chemotherapeutic agent comprises a cytotoxic agent, e.g., linked to a TIM3-specific antibody.

The high hematopoietic cancer cell binding TIM3-specific antibodies can be used for methods of treating hematopoietic cell cancers. In some embodiments, the method of treatment can comprise administering a high hematopoietic cancer cell binding TIM3-specific antibody to an individual, thereby treating the hematopoietic cell cancer in the individual. In some embodiments, the high hematopoietic cancer cell binding TIM3-specific antibody is linked to a cytotoxic agent. In some embodiments, the high hematopoietic cancer cell binding TIM3-specific antibody is cross-linked or multimerized prior to administration. In some embodiments, the method of treatment is combined with the diagnostic method, so that individuals having a hematopoietic cell cancer that displays an epitope that is well-recognized by a particular TIM3-specific antibody, as determined in the diagnostic method, are treated with the same antibody. In this way, the cancer cells in that individual can be more effectively targeted, e.g., than in a non-targeted, or non-individualized, therapeutic method. In this context, the term "well-recognized" indicates that a high percentage of PBMC or BMMC from the individual are bound by the TIM3-specific antibody, e.g., greater than 5%, 10%, 12%, 15%, 20% or more, or that the TIM3-specific antibody binds with high intensity, e.g., higher intensity than the 2E2 antibody as determined by FACS.

In some embodiments, the invention provides an isolated antibody specific for the extracellular domain of TIM3, wherein said antibody competes for binding to TIM3 with a competitor antibody comprising the CDR sequences of an antibody selected from 1.7E10, 7.10F6, 8.16C10, 27.12E12, 27.12A6, 27.2H4, 9.1G12, 6.16F9, 6.14B9, 33.1G12, 33.2A5, and 33.14A5 (see the sequence listing). In some embodiments, the TIM3-specific antibody competes for binding to TIM3 with a competitor antibody selected from the group consisting of 1.7E10, 7.10F6, 8.16C10, 27.12E12, 27.12A6, 27.2H4, 9.1G12, 6.16F9, 6.14B9, 33.1G12, 33.2A5, and 33.14A5. In some embodiments, the TIM3-specific antibody binds the same epitope on TIM3 as an antibody selected from 1.7E10, 7.10F6, 8.16C10, 27.12E12, 27.12A6, 27.2H4, 9.1G12, 6.16F9, 6.14B9, 33.1G12, 33.2A5, and 33.14A5. In some embodiments, the TIM3-specific antibody comprises the variable region sequences of an antibody selected from 1.7E10, 7.10F6, 8.16C10, 27.12E12, 27.12A6, 27.2H4, 9.1G12, 6.16F9, 6.14B9, 33.1G12, 33.2A5, and 33.14A5. In some embodiments, the TIM3-specific antibody is conjugated to a detectable label. In some embodiments, the TIM3-specific antibody is conjugated to a cytotoxic agent. In some embodiments, the TIM3-specific antibody is formulated in a pharmaceutical composition.

In some embodiments, the TIM3-specific antibody is used in a method for detecting the presence of a cancer cell, wherein the method comprises contacting any one of the TIM3-specific antibodies described herein with a plurality of cells and determining whether the TIM3-specific antibody binds to a cell in the plurality of cells, wherein binding indicates that the cell is a cancer cell. In some embodiments, the plurality of cells are in a biological sample from an individual and the method is practiced in vitro. In some embodiments, the plurality of cells are in an individual and the method is practiced in vivo. In some embodiments, the TIM3-specific antibody is conjugated to a detectable label. In some embodiments, the cancer cell is a cancer stem cell (CSC). In some embodiments, the cancer cell is a lymphoma cell (e.g., B cell, Hodgkin's, or Burkitt's lymphoma). In some embodiments, the cancer cell is a myeloma or leukemia cell (e.g., AML, CMML, CML). In some embodiments, the cancer cell is a solid tumor cell (e.g., from colon, ovarian, hepatic, prostate, renal, uterine, or breast cancer). In some embodiments, the method further comprises administering a chemotherapeutic agent to the individual.

Further provided are TIM3 specific antibodies that specifically bind the extracellular domain of TIM3, wherein the TIM3 specific antibody mediates complement dependent cytotoxicity (CDC). In this case, the TIM3-specific antibody is typically administered to an individual diagnosed with, or at risk of developing, cancer, wherein the individual has a functional complement system. In some embodiments, the TIM3-specific antibody is a chimeric antibody, e.g., comprising a human Fc region when the recipient of the TIM3-specific antibody is human. In some embodiments, the TIM3-specific antibody mediates CDC in at least 20% of the TIM3-expressing cells in a population under conditions appropriate for CDC. In some embodiments, the TIM3 specific antibody is selected from the group consisting of:

an antibody comprising the CDR sequences of 1.7E10 (CDRH1-3=SEQ ID NOs:3-5; CDRL1-3=SEQ ID NOs:8-10);
an antibody comprising the CDR sequences of 7.10F6 (CDRH1-3=SEQ ID NOs:13-15; CDRL1-3=SEQ ID NOs:18-20);
an antibody having the CDR sequences of 8.16C10 (CDRH1-3=SEQ ID NOs:23-25; CDRL1-3=SEQ ID NOs:28-30);
an antibody having variable region sequences of 1.7E10 (Vl=SEQ ID NO:7; Vh=SEQ ID NO:2)
an antibody having variable region sequences of 7.10F6 (Vl=SEQ ID NO:17; Vh=SEQ ID NO:12); and
an antibody having variable region sequences of 8.16C10 (Vl=SEQ ID NO:27; Vh=SEQ ID NO:22).

Further provided are antibodies that specifically bind the extracellular domain of TIM3, wherein said binding inhibits release of an inflammatory cytokine from an activated CD4+ T cell, compared to the release of the inflammatory cytokine in the absence of the antibody. In some embodiments, the inflammatory cytokine is IL-6. In some embodiments the inflammatory cytokine is IFN-gamma. In some embodiments, the inflammatory cytokine reducing TIM3 specific antibody reduces release of the inflammatory cytokine (e.g., IL-6 or IFN-gamma) more than the 2E2 antibody.

In some embodiments, the inflammatory cytokine reducing TIM3-specific antibody is selected from the group consisting of:

an antibody comprising the CDR sequences of 1.7E10 (CDRH1-3=SEQ ID NOs:3-5; CDRL1-3=SEQ ID NOs:8-10);
an antibody comprising the CDR sequences of 7.10F6 (CDRH1-3=SEQ ID NOs:13-15; CDRL1-3=SEQ ID NOs:18-20);
an antibody comprising the CDR sequences of 8.16C10 (CDRH1-3=SEQ ID NOs:23-25; CDRL1-3=SEQ ID NOs:28-30);
an antibody comprising the CDR sequences of 9.1G12 (CDRH1-3=SEQ ID NOs:113-115; CDRL1-3=SEQ ID NOs:118-120);
an antibody comprising variable region sequences of 1.7E10 (Vl=SEQ ID NO:7; Vh=SEQ ID NO:2)
an antibody comprising variable region sequences of 7.10F6 (Vl=SEQ ID NO:17; Vh=SEQ ID NO:12);
an antibody comprising variable region sequences of 8.16C10 (Vl=SEQ ID NO:27; Vh=SEQ ID NO:22);
an antibody comprising variable region sequences of 9.1G12 (Vl=SEQ ID NO:117; Vh=SEQ ID NO:112).

In some embodiments, the TIM3-specific antibody is used in a method for reducing the release of inflammatory (e.g., Th1) cytokines from CD4+ T cells, wherein the method comprises contacting any one of the TIM-3 specific antibodies described herein with a CD4+ T cell (e.g., a CD4+ T cell prior to activation or an activated CD4+ T cell). The reduction is typically determined by reference to a control, e.g., the release of inflammatory cytokines before contact with the TIM3-specific antibody, or in a sample or individual not treated with the TIM3-specific antibody. In some embodiments, the inflammatory cytokine is interferon-gamma (IFN-gamma). In some embodiments, the inflammatory cytokine is IL-6. In some embodiments, the method is carried out in vitro. In some embodiments, the method is carried out in vivo, and the contacting comprises administering the selected TIM3-specific antibody to an individual with an inflammatory condition (e.g., chronic inflammation, over-recruitment or over-activation of leukocytes or macrophages, autoimmunity, multiple sclerosis, rheumatoid arthritis, type I diabetes, Crohn disease, atherosclerosis, allergic conditions (e.g., allergic encephalomyelitis, asthma), and glomerulonephritis).

BRIEF DESCRIPTION OF THE DRAWINGS

FIG. 7. The presently disclosed TIM3-specific antibodies reduce release of Th1 inflammatory cytokines from activated CD4+ T cells. Cytokine levels with the isotype control antibodies were arbitrarily set to 1.0. Addition of the indicated TIM3-specific antibodies to activated T cells reduced IFN-gamma release, and to a lesser extent, reduced IL-6 release.

FIGS. 8A and 8B. TIM3-specific 12E12 antibody shows CDC activity on cells from AML patient samples. FIG. 8A shows the intensity of staining denoted by the mean fluorescent intensity (MFI) versus the CDC activity. FIG. 8B shows the CDC activity of 12E12 (ms12E12), and was also split into responsive (n=5) and non-responsive (n=6) groups. Data was normalized to IgG control.

DETAILED DESCRIPTION OF THE INVENTION

Figure 1:
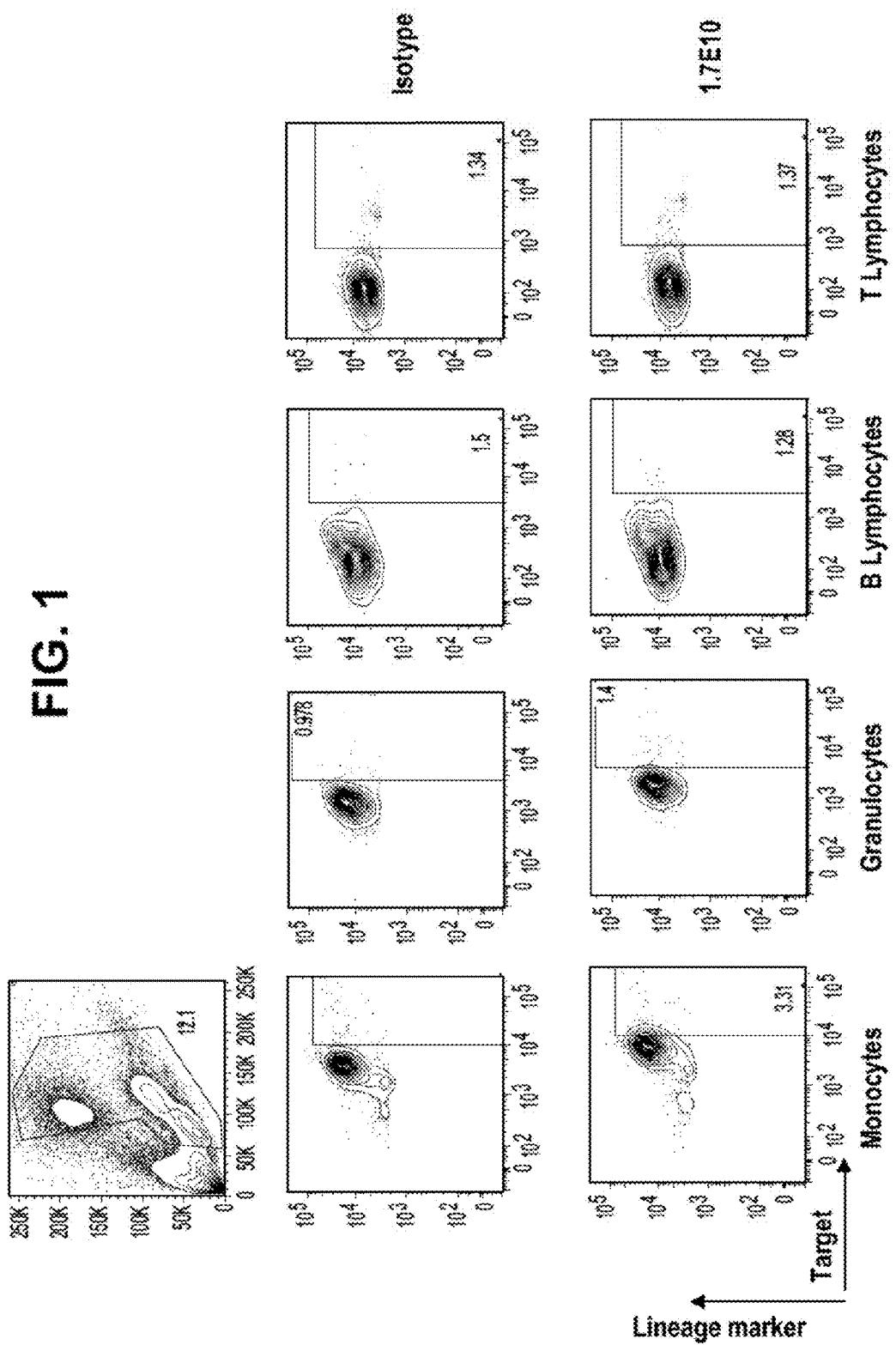
FIG. 1. TIM3-specific antibodies do not stain the majority of mature peripheral blood cells. Peripheral blood mononuclear cells (PBMCs) obtained from a normal donor were stained for various hematopoietic lineage markers and either the 1.7E10 antibody or isotype control.

Provided herein are antibodies specific for the extracellular region of TIM3 and that are rapidly internalized upon binding to a TIM3-expressing cell. In view of this discovery, the internalizing TIM3-specific antibodies can be used to deliver a cytotoxic agent specifically to TIM3-expressing cells, for example, cancer cells such as Cancer Stem Cells (CSC), leukemias, lymphomas, and solid tumor cells.

Also provided are TIM3-specific antibodies that inhibit cancer cell growth in the absence of a cytotoxic agent, e.g., under cross-linked or multimerized conditions. In some embodiments, the present TIM3-specific antibodies further provoke complement dependent cytotoxicity (CDC).

Also provided are TIM3-specific antibodies that are effective for reducing the release of inflammatory cytokines from CD4+ T cells. In addition to, or in combination with the therapeutic applications, the anti-TIM3 antibodies disclosed herein are useful for in vivo and in vitro diagnostic agents.

I. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4$^{th}$ ed. 2007); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

T cell Immunoglobulin- and Mucin domain—containing molecule 3 (TIM3), also known as HAVCR2, KIM-3, TIMD3, and FLJ14428, is a T helper cell type 1-specific cell surface protein that regulates macrophage activation and the severity of inflammatory conditions. TIM3 is also associated with cancer, in particular, with cancer stem cells. The nucleotide and protein sequences of TIM3 are known for many species. For example, the human sequences can be found at Genbank accession number AF251707.1 (SEQ ID NO:121) and Uniprot accession number Q8TDQ0 (SEQ ID NO:122). TIM3 is part of the TIM family of proteins which includes 4 members in mice and at least 3 members in humans. This family of proteins is characterized by an extracellular domain comprising an Ig like domain and a mucin domain (further comprising O-linked and N-linked glycosylation sites), a transmembrane domain, and an intracellular (cytoplasmic) domain. For the human TIM3 protein shown as SEQ ID NO: 122, the extracellular domain comprises approximately amino acids 22-202, the transmembrane domain comprises approximately amino acids 203-223, and the cytoplasmic domain comprises approximately amino acids 224-301. One of skill will understand that TIM3 variants (e.g., species homologs, allelic variants, etc.) can be optimally aligned, e.g., for identification of conserved residues and domains. For review, see Kuchroo et al. (2003) *Nature Rev. Immunol.* 3:454.

The terms "TIM3-specific antibody," "anti-TIM3 antibody," "TIM3 antibody," and "anti-TIM3" are used synonymously herein to refer to an antibody that specifically binds to TIM3. The TIM3 antibodies described herein specifically bind the TIM3 polypeptide expressed, e.g., on the surface of certain cancer cells (e.g., cancer stem cells (CSCs) or hematopoietic tumor cells (HTCs)), but not to most mature peripheral blood cells. As discussed in more detail below, the present anti-TIM3 antibodies can bind TIM3 expressing cells, inhibit their proliferation and/or mediate their destruction.

A "TIM3-associated disorder" (or TIM3 related disorder, TIM3 disorder, TIM3 related condition or disease, etc.) refers to conditions and diseases correlated with elevated or reduced cell surface expression of TIM3 as compared to TIM3 expression in a standard control (e.g., a normal, non-disease, non-cancer cell). Elevated TIM3 levels are associated with cancer cells, in particular, cancer stem cells.

The terms "internalize," "internalization," "endocytose," "endocytosis," "engulf," and like terms refer to uptake of a substance by a cell, e.g., by antibody (or receptor)-mediated endocytosis or phagocytosis.

The terms "engraft" or "engraftment" refers to the ability of a cell to survive, proliferate, and/or properly localize upon introduction into an individual or tissue. In the case of a cancer stem cell (CSC), the term can refer to the ability of the CSC to generate a tumor de novo or to spread to a different site. The term is commonly used to describe the ability of a population of cells to survive and function in a xenograft model (e.g., engraftment of human cells in a mouse). Engraftment of hematopoietic cells can be determined as described, e.g., in WO2006/047569. Engraftment of tumor cells can be determined as described, e.g., in Beckhove et al. (2003) *Int. J. Cancer* 105:444.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

A variety of methods of specific DNA and RNA measurements that use nucleic acid hybridization techniques are known to those of skill in the art (see, Sambrook, Id.). Some methods involve electrophoretic separation (e.g., Southern blot for detecting DNA, and Northern blot for detecting RNA), but measurement of DNA and RNA can also be carried out in the absence of electrophoretic separation (e.g., quantitative PCR, dot blot, or array).

The words "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following amino acids are typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "identical" or "percent identity," in the context of two or more nucleic acids, or two or more polypeptides, refer to two or more sequences or subsequences that are the same or have a specified percentage of nucleotides, or amino acids, that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nih.gov/BLAST. Such sequences are then said to be "substantially identical." This definition also refers to, or may be applied to, the compliment of a nucleotide test sequence. The definition also includes sequences that have deletions and/or additions, as well as those that have substitutions. As described below, the algorithms can account for gaps and the like. Typically, identity exists over a region comprising an antibody epitope, or a sequence that is at least about 25 amino acids or nucleotides in length, or over a region that is 50-100 amino acids or nucleotides in length, or over the entire length of the reference sequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "antibody" refers to a polypeptide comprising a framework region from an immunoglobulin gene, or fragments thereof, that specifically bind and recognize an antigen, e.g., TIM3, a particular cell surface marker, or any desired target. Typically, the "variable region" contains the antigen-binding region of the antibody (or its functional equivalent) and is most critical in specificity and affinity of binding. See Paul, *Fundamental Immunology* (2003).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

An "isotype" is a class of antibodies defined by the heavy chain constant region. Immunoglobulin genes include the kappa, lambda, alpha, gamma, delta, epsilon, and mu constant region genes. Light chains are classified as either kappa or lambda. Heavy chains are classified as gamma, mu, alpha, delta, or epsilon, which in turn define the isotype classes, IgG, IgM, IgA, IgD and IgE, respectively.

Antibodies can exist as intact immunoglobulins or as any of a number of well-characterized fragments that include specific antigen-binding activity. Such fragments can be produced by digestion with various peptidases. Pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

A "monoclonal antibody" refers to a clonal preparation of antibodies with a single binding specificity and affinity for a given epitope on an antigen. A "polyclonal antibody" refers to a preparation of antibodies that are raised against a single antigen, but with different binding specificities and affinities.

As used herein, "V-region" refers to an antibody variable region domain comprising the segments of Framework 1, CDR1, Framework 2, CDR2, and Framework 3, including CDR3 and Framework 4, which segments are added to the V-segment as a consequence of rearrangement of the heavy chain and light chain V-region genes during B-cell differentiation.

As used herein, "complementarity-determining region (CDR)" refers to the three hypervariable regions in each chain that interrupt the four "framework" regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, (1987) *J. Mol. Biol.* 196, 901-917; Chothia et al. (1989) Nature 342, 877-883; Chothia et al. (1992) J. Mol. Biol. 227, 799-817; Al-Lazikani et al., *J. Mol. Biol* 1997, 273(4)). Definitions of antigen combining sites are also described in the following: Ruiz et al. *Nucleic Acids Res.*, 28, 219-221 (2000); and Lefranc *Nucleic Acids Res.* January 1; 29(1):207-9 (2001); MacCallum et al., *J. Mol. Biol.*, 262: 732-745 (1996); and Martin et al, *Proc. Natl Acad. Sci. USA,* 86, 9268-9272 (1989); Martin, et al, *Methods Enzymol.,* 203: 121-153, (1991); Pedersen et al, *Immunomethods,* 1, 126, (1992); and Rees et al, In Sternberg M. J. E. (ed.), Protein Structure Prediction. Oxford University Press, Oxford, 141-172 1996).

A "chimeric antibody" is an antibody molecule in which (a) the constant region, or a portion thereof, is altered, replaced or exchanged so that the antigen binding site (variable region, CDR, or portion thereof) is linked to a constant region of a different or altered class, effector function and/or species, or an entirely different molecule which confers new properties to the chimeric antibody (e.g., an enzyme, toxin, hormone, growth factor, drug, etc.); or (b) the variable region, or a portion thereof, is altered, replaced or exchanged with a variable region having a different or altered antigen specificity (e.g., CDR and framework regions from different species).

The antibody binds to an "epitope" on the antigen. The epitope is the specific antibody binding interaction site on the antigen, and can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope). The same is true for other types of target molecules that form three-dimensional structures.

The term "specifically bind" refers to a molecule (e.g., antibody or antibody fragment) that binds to a target with at least 2-fold greater affinity than non-target compounds, e.g., at least 4-fold, 5-fold, 6-fold, 7-fold, 8-fold, 9-fold, 10-fold, 20-fold, 25-fold, 50-fold, or 100-fold greater affinity. For example, an antibody that specifically binds TIM3 will typically bind to TIM3 with at least a 2-fold greater affinity than a non-TIM3 target (e.g., a different TIM family member).

The term "binds" with respect to a cell type (e.g., an antibody that binds lymphoma cells), typically indicates that an agent binds a majority of the cells in a pure population of those cells. For example, an antibody that binds a given cell type typically binds to at least ⅔ of the cells in a population of the indicated cells (e.g., 75, 80, 85, 90, 91, 92, 93, 94, 95, 96, 97, 98, 99, or 100%). One of skill will recognize that some variability will arise depending on the method and/or threshold of determining binding.

The term "cross-linked" with respect to an antibody refers to attachment of the antibody to a solid or semisolid matrix (e.g., sepharose, beads, culture plate), or to another protein or antibody. For example, the antibody can be multimerized to create an antibody complex with multiple (more than 2) antigen-binding sites. The antibody can be multimerized by expressing the antibody as a high-valency isotype (e.g., IgA or IgM, which typically form complexes of 2 or 5 antibodies, respectively). Antibody multimerization can also be carried out by using a cross-linker comprising a reactive group capable of linking proteins (e.g., carbodiimide, NHS esters, etc). Methods and compositions for cross-linking an antibody to a matrix are described, e.g., in the Abcam and New England Biolab catalogs and websites (available at abcam-.com and neb.com). Cross-linker compounds with various reactive groups are described, e.g., in Thermo Fisher Scientific catalog and website (available at piercenet.com).

As used herein, a first antibody, or an antigen-binding portion thereof, "competes" for binding to a target with a second antibody, or an antigen-binding portion thereof, when binding of the second antibody with the target is detectably decreased in the presence of the first antibody compared to the binding of the second antibody in the absence of the first antibody. The alternative, where the binding of the first antibody to the target is also detectably decreased in the presence of the second antibody, can, but need not be the case. That is, a second antibody can inhibit the binding of a first antibody to the target without that first antibody inhibiting the binding of the second antibody to the target. However, where each antibody detectably inhibits the binding of the other antibody to its cognate epitope or ligand, whether to the same, greater, or lesser extent, the antibodies are said to "cross-compete" with each other for binding of their respective epitope(s). Both competing and cross-competing antibodies are encompassed by the present invention. The term "competitor" antibody can be applied to the first or second antibody as can be determined by one of skill in the art. In some cases, the presence of the competitor antibody (e.g., the first antibody) reduces binding of the second antibody to the target by at least 10%, e.g., 20%, 30%, 40%, 50%, 60%, 70%, 80%, or more, e.g., so that binding of the second antibody to target is undetectable in the presence of the first (competitor) antibody.

The term "differentially expressed" or "differentially regulated" refers generally to a protein or nucleic acid biomarker that is overexpressed (upregulated) or underexpressed (downregulated) in one sample compared to at least one other sample. In the context of the present invention, the term generally refers to overexpression of a biomarker (TIM3) on a cancer cell compared to a normal, non-cancer cell.

For example, the terms "overexpressed" or "upregulated" interchangeably refer to a protein or nucleic acid, generally a biomarker, that is transcribed or translated at a detectably greater than control level. The term includes overexpression due to transcription, post transcriptional processing, translation, post-translational processing, cellular localization (e.g., organelle, cytoplasm, nucleus, cell surface), and RNA and protein stability. Overexpression can be detected using conventional techniques for detecting biomarkers, whether mRNA (i.e., RT-PCR, hybridization) or protein (i.e., flow cytometry, imaging, ELISA, immunohistochemical techniques). Overexpression can be 10%, 20%, 30%, 40%, 50%, 60%, 70%, 80%, 90% or more in comparison to a normal cell.

The terms "agonist," "activator," "inducer" and like terms refer to molecules that increase activity or expression as compared to a control. Agonists are agents that, e.g., bind to, stimulate, increase, activate, enhance activation, sensitize or upregulate the activity of the target. The expression or activity can be increased 10%, 20%, 30%, 40%, 50%, 60%, 70%, 80%, 90% 100% or more than that in a control. In certain instances, the activation is 1.5-fold, 2-fold, 3-fold, 4-fold, 5-fold, 10-fold, or more in comparison to a control.

The terms "inhibitor," "repressor" or "antagonist" or "downregulator" interchangeably refer to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of benefit and/or side effects). Controls can be designed for in vitro applications. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, Bioconjugate Techniques 1996, Academic Press, Inc., San Diego.

A "labeled" molecule (e.g., nucleic acid, protein, or antibody) is one that is bound, either covalently, through a linker or a chemical bond, or noncovalently, through ionic, van der Waals, electrostatic, or hydrogen bonds to a label such that the presence of the molecule may be detected by detecting the presence of the label bound to the molecule.

The term "diagnosis" refers to a relative probability that a disorder such as cancer or an inflammatory condition is present in the subject. Similarly, the term "prognosis" refers to a relative probability that a certain future outcome may occur in the subject. For example, in the context of the present invention, prognosis can refer to the likelihood that an individual will develop cancer, have recurrence, or the likely severity of the disease (e.g., severity of symptoms, rate of functional decline, survival, etc.). The terms are not intended to be absolute, as will be appreciated by any one of skill in the field of medical diagnostics.

"Biopsy" or "biological sample from a patient" as used herein refers to a sample obtained from a patient having, or suspected of having, a TIM3 associated disorder. In some embodiments, the sample may be a tissue biopsy, such as needle biopsy, fine needle biopsy, surgical biopsy, etc. The sample can also be a blood sample or blood fraction, e.g., white blood cell fraction, serum, or plasma. The sample can comprise a tissue sample harboring a lesion or suspected lesion, although the biological sample may be also be derived from another site, e.g., a site of suspected metastasis, a lymph node, or from the blood. In some cases, the biological sample may also be from a region adjacent to the lesion or suspected lesion.

A "biological sample" can be obtained from a patient, e.g., a biopsy, from an animal, such as an animal model, or from cultured cells, e.g., a cell line or cells removed from a patient and grown in culture for observation. Biological samples include tissues and bodily fluids, e.g., blood, blood fractions, lymph, saliva, urine, feces, etc.

The terms "therapy," "treatment," and "amelioration" refer to any reduction in the severity of symptoms. In the case of treating cancer, treatment can refer to, e.g., reducing tumor size, number of cancer cells, growth rate, metastatic activity, reducing cell death of non-cancer cells, reduced nausea and other chemotherapy or radiotherapy side effects, etc. In the case of treating an inflammatory condition, the treatment can refer to, e.g., reducing blood levels of inflammatory cytokines, pain, swelling, recruitment of immune cells, etc. As used herein, the terms "treat" and "prevent" are not intended to be absolute terms. Treatment and prevention can refer to any delay in onset, amelioration of symptoms, improvement in patient survival, increase in survival time or rate, etc. Treatment and prevention can be complete (undetectable levels of neoplastic cells) or partial, such that fewer neoplastic cells are found in a patient than would have occurred without the present invention. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

The terms "effective amount," "effective dose," "therapeutically effective amount," etc. refer to that amount of the therapeutic agent sufficient to ameliorate a disorder, as described above. For example, for the given parameter, a therapeutically effective amount will show an increase or decrease of therapeutic effect at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

As used herein, the term "pharmaceutically acceptable" is used synonymously with physiologically acceptable and pharmacologically acceptable. A pharmaceutical composition will generally comprise agents for buffering and preservation in storage, and can include buffers and carriers for appropriate delivery, depending on the route of administration.

The terms "dose" and "dosage" are used interchangeably herein. A dose refers to the amount of active ingredient given to an individual at each administration. For the present invention, the dose can refer to the concentration of the antibody or associated components, e.g., the amount of therapeutic agent or dosage of radiolabel. The dose will vary depending on a number of factors, including frequency of administration; size and tolerance of the individual; severity of the condition; risk of side effects; the route of administration; and the imaging modality of the detectable moiety (if present). One of skill in the art will recognize that the dose can be modified depending on the above factors or based on therapeutic progress. The term "dosage form" refers to the particular format of the pharmaceutical, and depends on the route of administration. For example, a dosage form can be in a liquid, e.g., a saline solution for injection.

"Subject," "patient," "individual" and like terms are used interchangeably and refer to, except where indicated, mammals such as humans and non-human primates, as well as rabbits, rats, mice, goats, pigs, and other mammalian species. The term does not necessarily indicate that the subject has been diagnosed with a particular disease, but typically refers to an individual under medical supervision. A patient can be an individual that is seeking treatment, monitoring, adjustment or modification of an existing therapeutic regimen, etc. A "cancer patient" can refer to an individual that has been diagnosed with cancer, is currently following a therapeutic regimen, or is at risk of recurrence, e.g., after surgery to remove a tumor. In some embodiments, the cancer patient has been diagnosed with cancer and is a candidate for therapy. Cancer patients can include individuals that have not received treatment, are currently receiving treatment, have had surgery, and those that have discontinued treatment.

In the context of treating cancer, a subject in need of treatment can refer to an individual that has cancer or a pre-cancerous condition, has had cancer and is at risk of recurrence, is suspected of having cancer, is undergoing standard treatment for cancer, such as radiotherapy or chemotherapy, etc. Similarly, in the context of treating inflammation, a subject in need to treatment can refer to an individual that has an inflammatory condition (e.g., an allergic or immune response), is at risk of developing inflammation from a preexisting condition (e.g., allergies), or is at risk of developing inflammation due to exposure or likely exposure to an inflammatory or antigenic substance, e.g., due to travel.

"Cancer", "tumor," "transformed" and like terms include precancerous, neoplastic, transformed, and cancerous cells, and can refer to a solid tumor, or a non-solid cancer (see, e.g., Edge et al. *AJCC Cancer Staging Manual* ($7^{th}$ ed. 2009); Cibas and Ducatman *Cytology: Diagnostic principles and clinical correlates* ($3^{rd}$ ed. 2009)). Cancer includes both benign and malignant neoplasms (abnormal growth). "Transformation" refers to spontaneous or induced phenotypic changes, e.g., immortalization of cells, morphological changes, aberrant cell growth, reduced contact inhibition and anchorage, and/or malignancy (see, Freshney, *Culture of Animal Cells a Manual of Basic Technique* ($3^{rd}$ ed. 1994)). Although transformation can arise from infection with a transforming virus and incorporation of new genomic DNA, or uptake of exogenous DNA, it can also arise spontaneously or following exposure to a carcinogen.

The term "cancer" can refer to carcinomas, sarcomas, adenocarcinomas, lymphomas, leukemias, solid and lymphoid cancers, etc. Examples of different types of cancer include, but are not limited to, lung cancer (e.g., non-small cell lung cancer or NSCLC), ovarian cancer, prostate cancer, colorectal cancer, liver cancer (i.e., hepatocarcinoma), renal cancer (i.e., renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma; head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia (AML), chronic myeloid leukemia (CML), and multiple myeloma. In some embodiments, the compositions and methods of the present invention are useful for treating cancer.

A "cancer target" or "cancer marker" is a molecule that is differentially expressed or processed in cancer, e.g., on a cancer cell or in the cancer milieu. Exemplary cancer targets are cell surface proteins such as TIM3 (also, e.g., cell adhesion molecules and receptors), intracellular receptors, hormones, and molecules such as proteases that are secreted by cells into the cancer milieu. Markers for specific cancers are known in the art, e.g., MUC1 expression on colon and colorectal cancers, bombesin receptors in lung cancer, and prostate specific membrane antigen (PSMA) on prostate cancer.

In some embodiments, the cancer target can be associated with a certain type of cancer cell, e.g., leukemia, myeloma, lymphoma, AML, non-small cell lung cancer cells, prostate cancer, colorectal cancer, breast cancer or ovarian cancer. A cell type specific target is typically expressed at levels at least 2 fold greater in that cell type than in a reference population of cells. In some embodiments, the cell type specific marker is present at levels at least 3, 4, 5, 6, 7, 8, 9, 10 20, 50, 100, or 1000 fold higher than its average expression in a reference population. Thus, the target can be detected or measured to distinguish the cell type or types of interest from other cells. For example, AML cancer targets include Ly86, LILRA1, and CD180.

A cancer stem cell (CSC) is a cell found in a tumor or blood cancer that can give rise to the cells that make up the bulk of the cancer. The CSC can also be self-renewing, similar to a normal (non-cancer) stem cell. CSCs can thus mediate metastasis by migrating to a non-tumor tissue in an individual and starting a "new" tumor. CSCs make up a very small percentage of any given cancer, depending on the stage that the cancer is detected. For example, the average frequency of CSCs in a sample of AML cells is believed to be about 1:10,000. Hematopoietic CSCs can be identified as CD34+, similar to normal hematopoietic stem cells (HSCs). Other CSC associated markers include CD44 (breast), CD133 (glial cancers), and Notch (e.g., myelomas and neuroblastoma).

An "inflammatory condition" refers to any inflammation in an individual, and can be transient (e.g., in response to exposure to a pathogen or allergen) or chronic. Inflammation is characterized by inflammatory cytokines such as IFN-gamma, IL-6, and TNF-alpha that recruit and activate macrophages and other leukocytes. In some cases, inflammation can develop into a chronic, harmful condition or autoimmune condition (e.g., MS, lupus, rheumatoid arthritis, Crohn's disease). Inflammation can be evident locally (e.g., at a localized site of infection or exposure) or systemically (e.g., atherosclerosis, high blood pressure).

II. TIM3 and TIM3-Associated Disorders

TIM3-associated disorders include cancers associated with elevated TIM3 expression and inflammatory disorders associated with reduced TIM3 expression, as described below. The antibodies of the invention can be used for diagnosis and monitoring of these disorders, as well as targeted therapy, e.g., in the case of delivering a chemotherapeutic (or cytotoxic) agent specifically to a TIM3-expressing cancer cell. In some cases, the targeted therapy can comprise contacting a TIM3-expressing cell with an antibody, as described herein.

TIM3 is expressed on Th1 (T helper type 1) cells, which are typically pro-inflammatory. As shown herein, however, TIM3 can be targeted as a negative regulator of pro-inflammatory pathways. Thus, some TIM3 specific antibodies described herein can be used in cases where it is desirable to reduce inflammation. TIM3 antibodies described herein can be used to reduce the onset or severity of autoimmune and inflammatory conditions, e.g., multiple sclerosis, rheumatoid arthritis, type I diabetes, Crohn disease, atherosclerosis, allergic conditions (e.g., allergic encephalomyelitis, asthma), and glomerulonephritis. Release of inflammatory cytokines (e.g., IFN-gamma) from activated T cells can lead to increased macrophage infiltration into an affected site, and increased tissue damage.

TIM3 is also associated with cancer cells and cancer stem cells, and binding TIM3 (e.g., with a TIM3 specific antibody, or a TIM3 specific antibody linked to a cytotoxic agent) can effectively inhibit cancer cell growth. The present TIM3 specific antibodies can also be used for diagnosis or localization of a TIM3 expressing cancer, optionally followed by targeted therapy using a TIM3 specific antibody (e.g., the same antibody, or a different TIM3 specific antibody with different binding characteristics).

The results described herein provide the first demonstration that TIM3 is expressed on B cell lymphoma cells. The presently described TIM3 specific antibodies can thus be used to target B cell lymphomas (e.g., for diagnostic and/or therapeutic applications) as well as the other cancers associated with TIM3 expression. TIM3 expression is associated with myelomas and other hematopoietic cell cancers, and carcinomas (e.g., carcinomas of the colon, ovary, liver, prostate, uterus, breast, and kidney). Examples of cancers that can be targeted using anti-TIM3 antibodies thus include hematopoietic cell cancers (e.g., B cell lymphoma, Burkitt's lymphoma, Hodgkin's lymphoma, non-Hodgkin's lymphoma, myelodysplastic syndrome (preleukemia), leukemias, and myelomas (e.g., acute myeloid leukemia (AML), chronic myeloid leukemia (CML), chronic myelomoncytic leukemia (CMML), multiple myeloma, plasmacytoma)). Additional TIM3 expressing cancers that can be targeted using the presently disclosed antibodies include but are not limited to colon carcinoma, ovarian carcinoma, prostate carcinoma, breast carcinoma, renal carcinoma, liver carcinoma, and uterine carcinoma.

III. Anti-TIM3 Antibodies

Provided herein are anti-TIM3 antibodies (i.e., TIM3-specific antibodies, anti-TIM3) that specifically bind to the extracellular domain of TIM3. In some embodiments, the anti-TIM3 antibodies are rapidly internalized into TIM3-expressing cells (see, e.g., FIGS. 3 and 4). For example, in some embodiments, a higher percentage of the presently described TIM3 specific antibodies are internalized into TIM3-expressing cells than the 2E2 antibody at the same concentration, same temperature, and in the same time period (e.g., 1, 2, 5, 10, 20, or 30 minutes). In some embodiments, more than 30, 40, 50, 60, 70, 80% or higher percentage of the present TIM3 specific antibodies are internalized into a population of TIM3 expressing cells in less than 30 minutes. One of skill will appreciate that the amount of antibody and cell number will affect the percentage of antibody internalization. Typically, an excess of antibody is used (greater than 1 antibody/cell, e.g., at least $10^3$ antibody/cell) so that antibody concentration is not a limiting factor. The internalizing anti-TIM3 antibodies can thus be used to efficiently deliver a therapeutic agent to targeted TIM3-expressing cells (e.g. cancer cells).

Figure 5:
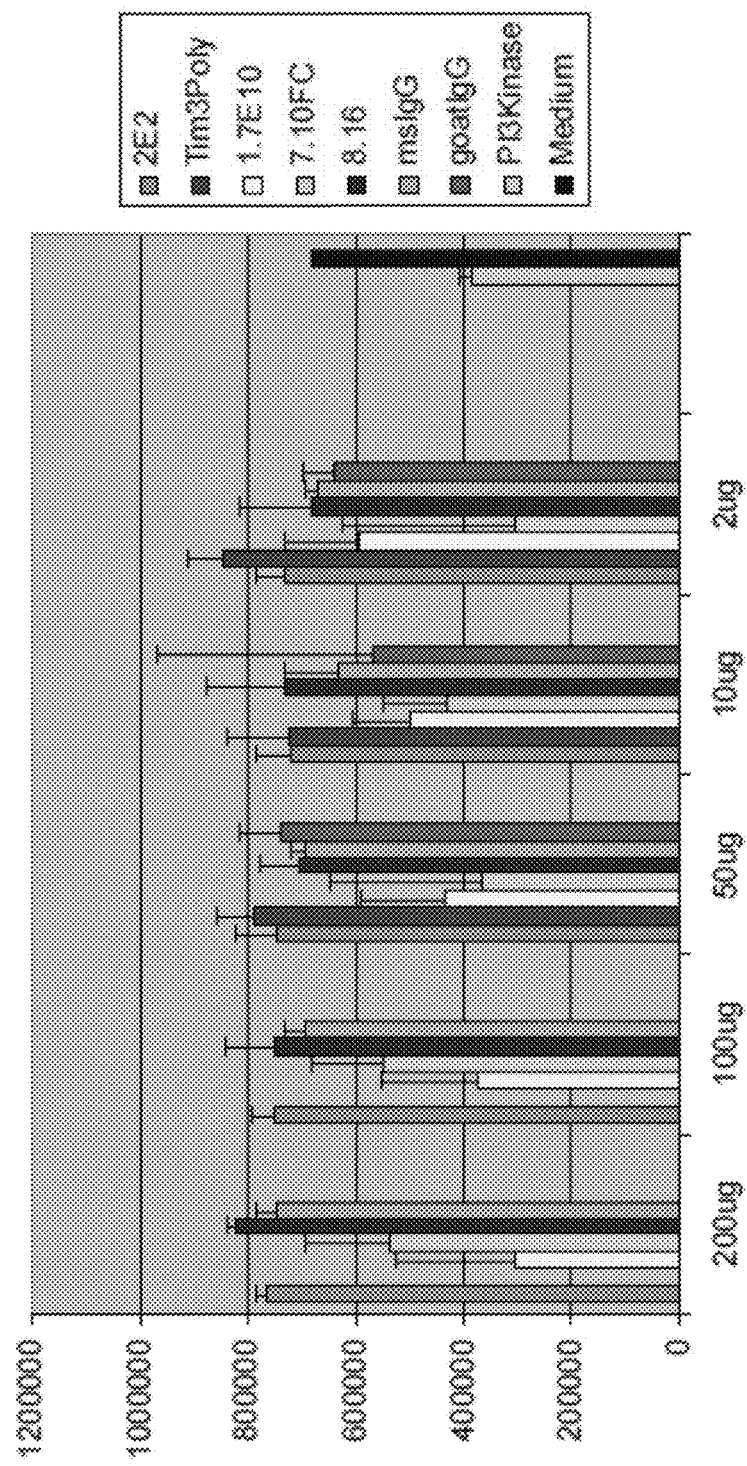
FIG. 5. The presently disclosed TIM3-specific antibodies inhibit proliferation of TIM3-expressing leukemia cells (CMK AML cell line) in cross-linking conditions. The indicated antibodies were plated at various levels (indicated below each set of data) before addition of cells. Relative cell numbers are indicated on the left.

Surprisingly, anti-TIM3 antibodies described herein can also inhibit growth of TIM3-expressing cells, when cross-linked or multimerized (see, e.g., FIG. 5). These anti-TIM3 antibodies can be used to inhibit cell growth of TIM3 expressing cells (e.g., cancer cells) in the absence of a conjugated cytotoxic agent.

Figure 6:
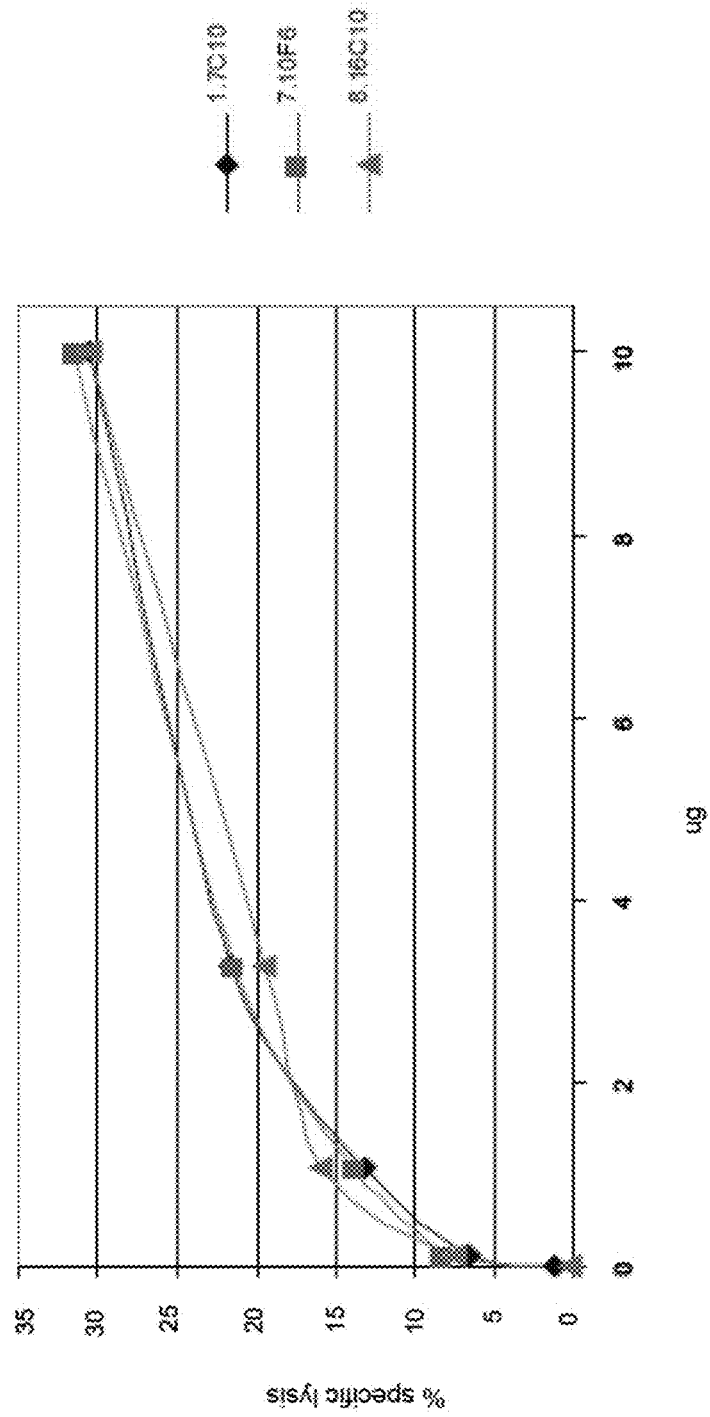
FIG. 6. The presently disclosed TIM3-specific antibodies induce complement dependent cytotoxicity. The variable regions for each indicated antibody (1.7E10, 7.10F6, and 8.16C10) were conjugated to the Fc regions from human antibody. Lysis of TIM3-expressing cells increased in a dose-dependent manner.

Anti-TIM3 antibodies described herein also show complement dependent cytotoxicity (CDC) activity (see, e.g., FIG. 6). These anti-TIM3 antibodies can also thus be used to target TIM3 expressing cells for destruction, e.g. in the absence of a conjugated cytotoxic agent.

Also unexpected were anti-TIM3 antibodies described herein that can reduce release of inflammatory cytokines from activated T cells, and thereby reduce the severity of inflammatory responses (see, e.g., FIG. 7). Anti-TIM3 antibodies having this activity can thus be used to inhibit inflammation in individuals in need thereof.

Anti-TIM3 antibodies described herein have unique cell binding activities, for example, as described in Examples 2 and 3. For example, it was previously unknown that TIM3 could be used to target B cell lymphoma cells (exemplified as Pfeiffer cells). Yet the present results show that several of the disclosed anti-TIM3 antibodies are able to target these cells at a high level (see, e.g., FIGS. 3 and 4 and Table 2). In addition, several of the presently disclosed anti-TIM3 antibodies bind to leukemia cells, e.g., from AML patients, at a higher percentage and/or with high intensity than the 2E2 antibody (see, e.g., FIG. 2 and Tables 3 and 4). These antibodies can be used for detecting cancer cells that display an epitope that is targeted with high affinity by at least one of the anti-TIM3 antibodies disclosed herein. In some embodiments, those cancer cells can then be targeted for destruction with the same anti-TIM3 antibody. Such methods can include treating an individual having TIM3 expressing cancer cells, e.g., as described herein, comprising administering the anti-TIM3 antibody to the individual.

In some embodiments, the invention includes anti-TIM3 antibodies that compete for binding to TIM3 with a competitor antibody selected from the group consisting of:

an antibody having the CDR sequences of 1.7E10 (CDRH1-3=SEQ ID NOs:3-5; CDRL1-3=SEQ ID NOs:8-10)

an antibody having the CDR sequences of 7.10F6 (CDRH1-3=SEQ ID NOs:13-15; CDRL1-3=SEQ ID NOs:18-20);

an antibody having the CDR sequences of 8.16C10 (CDRH1-3=SEQ ID NOs:23-25; CDRL1-3=SEQ ID NOs:28-30);

an antibody having the CDR sequences of 27.12E12 (CDRH1-3=SEQ ID NOs:103-105; CDRL1-3=SEQ ID NOs:108-110);

an antibody having the CDR sequences of 27.2H4 (CDRH1-3=SEQ ID NOs:33-35; CDRL1-3=SEQ ID NOs:38-40);

an antibody having the CDR sequences of 27.12A6 (CDRH1-3=SEQ ID NOs:43-45; CDRL1-3=SEQ ID NOs:48-50);

an antibody having the CDR sequences of 9.1G12 (CDRH1-3=SEQ ID NOs:113-115; CDRL1-3=SEQ ID NOs:118-120);

an antibody having the CDR sequences of 6.16F9 (CDRH1-3=SEQ ID NOs:63-65; CDRL1-3=SEQ ID NOs:68-70);

an antibody having the CDR sequences of 6.14B9 (CDRH1-3=SEQ ID NOs:53-55; CDRL1-3=SEQ ID NOs:58-60);

an antibody having the CDR sequences of 33.1G12 (CDRH1-3=SEQ ID NOs:73-75; CDRL1-3=SEQ ID NOs:78-80);

an antibody having the CDR sequences of 33.2A5 (CDRH1-3=SEQ ID NOs:83-85; CDRL1-3=SEQ ID NOs:88-90); and an antibody having the CDR sequences of 33.14A5 (CDRH1-3=SEQ ID NOs:93-95; CDRL1-3=SEQ ID NOs:98-100).

In some embodiments, the anti-TIM3 antibodies competes for binding with an antibody selected from the group consisting of:

an antibody comprising variable region sequences with substantial identity (at least (85, 90, 95, or 98% identity) to those of 1.7E10 (Vl=SEQ ID NO:7; Vh=SEQ ID NO:2)

an antibody comprising variable region sequences with substantial identity to those of 7.10F6 (Vl=SEQ ID NO:17; Vh=SEQ ID NO:12);

an antibody comprising variable region sequences with substantial identity to those of 8.16C10 (Vl=SEQ ID NO:27; Vh=SEQ ID NO:22);

an antibody comprising variable region sequences with substantial identity to those of 27.12E12 (Vl=SEQ ID NO:107; Vh=SEQ ID NO:102);

an antibody comprising variable region sequences with substantial identity to those of 27.2H4 (Vl=SEQ ID NO:37; Vh=SEQ ID NO:32);

an antibody comprising variable region sequences with substantial identity to those of 27.12A6 (Vl=SEQ ID NO:47; Vh=SEQ ID NO:42);

an antibody comprising variable region sequences with substantial identity to those of 9.1G12 (Vl=SEQ ID NO:117; Vh=SEQ ID NO:112);

an antibody comprising variable region sequences with substantial identity to those of 6.16F9 (Vl=SEQ ID NO:67; Vh=SEQ ID NO:62);

an antibody comprising variable region sequences with substantial identity to those of 6.14B9 (Vl=SEQ ID NO:57; Vh=SEQ ID NO:52);

an antibody comprising variable region sequences with substantial identity to those of 33.1G12 (Vl=SEQ ID NO:77; Vh=SEQ ID NO:72);

an antibody comprising variable region sequences with substantial identity to those of 33.2A5 (Vl=SEQ ID NO:87; Vh=SEQ ID NO:82); and an antibody comprising variable region sequences with substantial identity to those of 33.14A5 (Vl=SEQ ID NO:97; Vh=SEQ ID NO:92).

Numerous types of competitive binding assays are known, including solid phase direct or indirect radioimmunoassay (RIA); solid phase direct or indirect enzyme immunoassay (EIA), sandwich competition assay (see Stahli et al., *Methods in Enzymology* 9:242-253 (1983)); solid phase direct biotin-avidin EIA (see Kirkland et al., *J. Immunol.* 137:3614-3619 (1986)); solid phase direct labeled assay; solid phase direct labeled sandwich assay (see Harlow and Lane, *Antibodies, A Laboratory Manual*, Cold Spring Harbor Press (1988)); solid phase direct label RIA using 1-125 label (see Morel et al., *Molec. Immunol.* 25(1):7-15 (1988)); solid phase direct biotin-avidin EIA (Cheung et al., *Virology* 176:546-552 (1990)); and direct labeled RIA (Moldenhauer et al., *Scand. J. Immunol.* 32:77-82 (1990)). Typically, such an assay involves the use of purified antigen bound to a solid surface or cells bearing either of these, an unlabelled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

In some embodiments, the anti-TIM3 antibody binds the same epitope as an antibody selected from the group consisting of:
  an antibody having the CDR sequences of 1.7E10 (CDRH1-3=SEQ ID NOs:3-5; CDRL1-3=SEQ ID NOs:8-10)
  an antibody having the CDR sequences of 7.10F6 (CDRH1-3=SEQ ID NOs:13-15; CDRL1-3=SEQ ID NOs:18-20);
  an antibody having the CDR sequences of 8.16C10 (CDRH1-3=SEQ ID NOs:23-25; CDRL1-3=SEQ ID NOs:28-30);
  an antibody having the CDR sequences of 27.12E12 (CDRH1-3=SEQ ID NOs:103-105; CDRL1-3=SEQ ID NOs:108-110);
  an antibody having the CDR sequences of 27.2H4 (CDRH1-3=SEQ ID NOs:33-35; CDRL1-3=SEQ ID NOs:38-40);
  an antibody having the CDR sequences of 27.12A6 (CDRH1-3=SEQ ID NOs:43-45; CDRL1-3=SEQ ID NOs:48-50);
  an antibody having the CDR sequences of 9.1G12 (CDRH1-3=SEQ ID NOs:113-115; CDRL1-3=SEQ ID NOs:118-120);
  an antibody having the CDR sequences of 6.16F9 (CDRH1-3=SEQ ID NOs:63-65; CDRL1-3=SEQ ID NOs:68-70);
  an antibody having the CDR sequences of 6.14B9 (CDRH1-3=SEQ ID NOs:53-55; CDRL1-3=SEQ ID NOs:58-60);
  an antibody having the CDR sequences of 33.1G12 (CDRH1-3=SEQ ID NOs:73-75; CDRL1-3=SEQ ID NOs:78-80);
  an antibody having the CDR sequences of 33.2A5 (CDRH1-3=SEQ ID NOs:83-85; CDRL1-3=SEQ ID NOs:88-90); and
  an antibody having the CDR sequences of 33.14A5 (CDRH1-3=SEQ ID NOs:93-95; CDRL1-3=SEQ ID NOs:98-100).

In some embodiments, the anti-TIM3 antibody has light chain CDR sequences and heavy chain CDR sequences having up to 1, 2, or 3 amino acid substitutions, additions, or deletions/CDR relative to the CDR sequences of an antibody selected from the group consisting of 1.7E10, 7.10F6, 8.16C10, 22.12E12, 27.2H4, 9.1G12, 6.16F9, 6.14B9, 33.1G12, 33.2A5, and 33.14A5. In some embodiments, the light chain CDR sequences include up to 1, 2, or 3 amino acid substitutions, additions or deletions/CDR relative to the light chain CDR sequences of the aforementioned anti-TIM3 antibodies. In some embodiments, the heavy chain CDR sequences include up to 1, 2, or 3 amino acid substitutions, additions, or deletions/CDR relative to the heavy chain CDR sequences of the aforementioned anti-TIM3 antibodies. In some embodiments, substitution, addition or deletion occurs in only 1, 2, 3, 4, or 5 CDRs of the 6 total CDRs.

In some embodiments, the anti-TIM3 antibody is selected from the group consisting of:
  an antibody having the CDR sequences of 1.7E10 (CDRH1-3=SEQ ID NOs:3-5; CDRL1-3=SEQ ID NOs:8-10)
  an antibody having the CDR sequences of 7.10F6 (CDRH1-3=SEQ ID NOs:13-15; CDRL1-3=SEQ ID NOs:18-20);
  an antibody having the CDR sequences of 8.16C10 (CDRH1-3=SEQ ID NOs:23-25; CDRL1-3=SEQ ID NOs:28-30);
  an antibody having the CDR sequences of 27.12E12 (CDRH1-3=SEQ ID NOs:103-105; CDRL1-3=SEQ ID NOs:108-110);
  an antibody having the CDR sequences of 27.2H4 (CDRH1-3=SEQ ID NOs:33-35; CDRL1-3=SEQ ID NOs:38-40);
  an antibody having the CDR sequences of 27.12A6 (CDRH1-3=SEQ ID NOs:43-45; CDRL1-3=SEQ ID NOs:48-50);
  an antibody having the CDR sequences of 9.1G12 (CDRH1-3=SEQ ID NOs:113-115; CDRL1-3=SEQ ID NOs:118-120);
  an antibody having the CDR sequences of 6.16F9 (CDRH1-3=SEQ ID NOs:63-65; CDRL1-3=SEQ ID NOs:68-70);
  an antibody having the CDR sequences of 6.14B9 (CDRH1-3=SEQ ID NOs:53-55; CDRL1-3=SEQ ID NOs:58-60);
  an antibody having the CDR sequences of 33.1G12 (CDRH1-3=SEQ ID NOs:73-75; CDRL1-3=SEQ ID NOs:78-80);
  an antibody having the CDR sequences of 33.2A5 (CDRH1-3=SEQ ID NOs:83-85; CDRL1-3=SEQ ID NOs:88-90); and
  an antibody having the CDR sequences of 33.14A5 (CDRH1-3=SEQ ID NOs:93-95; CDRL1-3=SEQ ID NOs:98-100).

In some embodiments, the anti-TIM3 antibody is selected from the group consisting of:
  an antibody having variable region sequences with at least 95% identity to those of 1.7E10 (Vl=SEQ ID NO:7; Vh=SEQ ID NO:2)
  an antibody having variable region sequences with at least 95% identity to those of 7.10F6 (Vl=SEQ ID NO:17; Vh=SEQ ID NO:12);
  an antibody having variable region sequences with at least 95% identity to those of 8.16C10 (Vl=SEQ ID NO:27; Vh=SEQ ID NO:22);
  an antibody having variable region sequences with at least 95% identity to those of 27.12E12 (Vl=SEQ ID NO:107; Vh=SEQ ID NO:102);
  an antibody having variable region sequences with at least 95% identity to those of 27.2H4 (Vl=SEQ ID NO:37; Vh=SEQ ID NO:32);
  an antibody having variable region sequences with at least 95% identity to those of 27.12A6 (Vl=SEQ ID NO:47; Vh=SEQ ID NO:42);
  an antibody having variable region sequences with at least 95% identity to those of 9.1G12 (Vl=SEQ ID NO:117; Vh=SEQ ID NO:112);
  an antibody having variable region sequences with at least 95% identity to those of 6.16F9 (Vl=SEQ ID NO:67; Vh=SEQ ID NO:62);

an antibody having variable region sequences with at least 95% identity to those of 6.14B9 (Vl=SEQ ID NO:57; Vh=SEQ ID NO:52);

an antibody having variable region sequences with at least 95% identity to those of 33.1G12 (Vl=SEQ ID NO:77; Vh=SEQ ID NO:72);

an antibody having variable region sequences with at least 95% identity to those of 33.2A5 (Vl=SEQ ID NO:87; Vh=SEQ ID NO:82); and an antibody having variable region sequences with at least 95% identity to those of 33.14A5 (Vl=SEQ ID NO:97; Vh=SEQ ID NO:92).

In some embodiments, the antibody also has at least one activity selected from

Binding to TIM3 with a $K_D$ of 100 nM or lower (e.g., 1-10 nM, 0.1-10 nM, 10-50 nM, about 20 nM, etc.);

Internalizing into TIM3-expressing cells at a higher rate than the anti-TIM3 antibody 2E2;

Reducing release of IFN-gamma and/or IL-6 from activated CD4+ T cells, compared to release in the absence of the antibody; and Reducing cell growth of TIM3-expressing cells when cross-linked or immobilized (e.g., on a solid or semi-solid matrix), compared to cell growth in the absence of the antibody.

Any of the antibodies described herein can be a chimeric antibody or a humanized antibody. In some embodiments, the antibody is a TIM3-binding antibody fragment, e.g., an Fab. In some embodiments, the anti-TIM3 antibody is labeled with a detectable agent, e.g., as described below. In some embodiments, the anti-TIM3 antibody is attached to a therapeutic agent, e.g., a chemotherapeutic or cytotoxic agent as described below.

In some embodiments, the anti-TIM3 antibody binds to TIM3 from a human. In some embodiments, the anti-TIM3 antibody binds to TIM3 from a rodent (mouse or rat).

A. Methods of Making Antibodies

For preparation of suitable antibodies of the invention and for use according to the invention, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, can be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Antibodies can be produced using any number of expression systems, including prokaryotic and eukaryotic expression systems. In some embodiments, the expression system is a mammalian cell expression, such as a hybridoma, or a CHO cell expression system. Many such systems are widely available from commercial suppliers. In embodiments in which an antibody comprises both a $V_H$ and $V_L$ region, the $V_H$ and $V_L$ regions may be expressed using a single vector, e.g., in a di-cistronic expression unit, or under the control of different promoters. In other embodiments, the $V_H$ and $V_L$ region may be expressed using separate vectors. A $V_H$ or $V_L$ region as described herein may optionally comprise a methionine at the N-terminus.

An antibody of the invention can also be produced in various formats, including as a Fab, a Fab', a $F(ab')_2$, a scFv, or a dAB. The antibody fragments can be obtained by a variety of methods, including, digestion of an intact antibody with an enzyme, such as pepsin (to generate $(Fab')_2$ fragments) or papain (to generate Fab fragments); or de novo synthesis. Antibody fragments can also be synthesized using recombinant DNA methodology. In some embodiments, the anti-TIM3 antibody comprises $F(ab')_2$ fragments that specifically bind TIM3. An antibody of the invention can also include a human constant region. See, e.g., Fundamental Immunology (Paul ed., 4d ed. 1999); Bird, et al., *Science* 242:423 (1988); and Huston, et al., *Proc. Natl. Acad. Sci. USA* 85:5879 (1988).

Methods for humanizing or primatizing non-human antibodies are also known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

In some cases, the antibody or antibody fragment can be conjugated to another molecule, e.g., polyethylene glycol (PEGylation) or serum albumin, to provide an extended half-life in vivo. Examples of PEGylation of antibody fragments are provided in Knight et al. *Platelets* 15:409, 2004 (for abciximab); Pedley et al., *Br. J. Cancer* 70:1126, 1994 (for an anti-CEA antibody); Chapman et al., *Nature Biotech.*

17:780, 1999; and Humphreys, et al., *Protein Eng. Des.* 20: 227, 2007). The antibody or antibody fragment can also be labeled, or conjugated to a therapeutic agent as described below.

B. Binding Affinity

The specificity of the binding can be defined in terms of the comparative dissociation constants (Kd) of the antibody (or other targeting moiety) for target, as compared to the dissociation constant with respect to the antibody and other materials in the environment or unrelated molecules in general. Typically, the Kd for the antibody with respect to the unrelated material will be at least 2-fold, 3-fold, 4-fold, 5-fold, 10-fold, 20-fold, 50-fold, 100-fold, 200-fold or higher than Kd with respect to the target.

The desired affinity for an antibody, e.g., high (pM to low nM), medium (low nM to 100 nM), or low (about 100 nM or higher), may differ depending upon whether it is being used as a diagnostic or therapeutic. Without being limited to theory, in one example, an antibody with medium affinity may be more successful in localizing to a tumor as compared to one with a high affinity. Thus, antibodies having different affinities can be used for diagnostic and therapeutic applications.

A targeting moiety will typically bind with a Kd of less than about 1000 nM, e.g., less than 250, 100, 50, 20 or lower nM. In some embodiments, the Kd of the affinity agent is less than 15, 10, 5, or 1 nM. In some embodiments, the Kd is 1-100 nM, 0.1-50 nM, 0.1-10 nM, or 1-20 nM. The value of the dissociation constant (Kd) can be determined by well-known methods, and can be computed even for complex mixtures by methods as disclosed, e.g., in Caceci et al., Byte (1984) 9:340-362.

Affinity of an antibody, or any targeting agent, for a target can be determined according to methods known in the art, e.g., as reviewed in Ernst et al. Determination of Equilibrium Dissociation Constants, *Therapeutic Monoclonal Antibodies* (Wiley & Sons ed. 2009).

Quantitative ELISA, and similar array-based affinity methods can be used. ELISA (Enzyme linked immunosorbent signaling assay) is an antibody-based method. In some cases, an antibody specific for target of interest is affixed to a substrate, and contacted with a sample suspected of containing the target. The surface is then washed to remove unbound substances. Target binding can be detected in a variety of ways, e.g., using a second step with a labeled antibody, direct labeling of the target, or labeling of the primary antibody with a label that is detectable upon antigen binding. In some cases, the antigen is affixed to the substrate (e.g., using a substrate with high affinity for proteins, or a Strepavidin-biotin interaction) and detected using a labeled antibody (or other targeting moiety). Several permutations of the original ELISA methods have been developed and are known in the art (see Lequin (2005) *Clin. Chem.* 51:2415-18 for a review).

The Kd, Kon, and Koff can also be determined using surface plasmon resonance (SPR), e.g., as measured by using a Biacore T100 system. SPR techniques are reviewed, e.g., in Hahnfeld et al. Determination of Kinetic Data Using SPR Biosensors, *Molecular Diagnosis of Infectious Diseases* (2004). In a typical SPR experiment, one interactant (target or targeting agent) is immobilized on an SPR-active, gold-coated glass slide in a flow cell, and a sample containing the other interactant is introduced to flow across the surface. When light of a given frequency is shined on the surface, the changes to the optical reflectivity of the gold indicate binding, and the kinetics of binding.

Binding affinity can also be determined by anchoring a biotinylated interactant to a streptaviden (SA) sensor chip. The other interactant is then contacted with the chip and detected, e.g., as described in Abdessamad et al. (2002) *Nuc. Acids Res.* 30:e45.

C. Internalization

TIM3-specific antibodies described herein can be internalized into TIM3-expressing cells, including TIM3-expressing lymphoma and AML cells. For example, TIM3 specific antibodies are shown in the Examples (and FIGS. 3 and 4) to be internalized into B lymphoma cells. In some cases, the disclosed antibodies are internalized at a higher rate, or at a higher level, than the 2E2 anti-TIM3 antibody. As demonstrated herein, the TIM3-specific antibodies described herein provide an effective means for targeting TIM3-expressing cells, e.g., with cytotoxic agents.

The percent internalization and internalization rate of an antibody can be evaluated by using methods known in the art, including, e.g., flow cytometry (FACS) and confocal fluorescent microscopy. Such methods are described, e.g., in Lue et al. (2007) *Nature Protocols* (*Nature Med.* 13:587-96); Cho et al. (2010) Biomacromolecules and Corbani et al. (2004) *Endocrinology* 145:2876-85, and as described herein.

For FACS and confocal microscopy, cells are incubated with a fluorescently-labeled targeting agent, e.g., antibody. The cells are typically selected to express the target of the labeled antibody, e.g., TIM3. Control cells can then be used that do not express the target. Internalization typically occurs at 37° C., but not at 4° C., which provides another control for the reaction. The cells can thus be contacted with the labeled agent and incubated at 37° C. or 4° C. (e.g., to detect binding without internalization).

Unbound, and surface-bound agent is removed by washing the cells, e.g., in an acid wash, followed by wash with a buffer at normal pH.

If adherent cells are used, the cells are removed from substrate prior to flow cytometry. The percentage of fluorescent cells indicates the percent internalization of the fluorescently-labeled agent. Percent internalization can also be expressed, e.g., as a percent of initial labeled agent added to the cells.

Internalization of an agent can also be evaluated by determining the localization of the fluorescently labeled agent by confocal microscopy. Methods of using confocal microscopy to determine internalization are described in, e.g., Xiao et al. (2008) *Chem. Eur. J.,* 14:1769-1775. Briefly, the cells are contacted with labeled agent and incubated as described above. Following incubation, the cells can be incubated on ice, washed in PBS buffer at 4° C., treated with 0.25% trypsin (to remove from substrate, if applicable). The cell suspension can then be applied to slides for confocal fluorescent microscopy. Suitable confocal microscopes include the FV500-IX81 confocal microscope (Olympus America Inc.; Center Valley, Pa.) and Eclipse Ti-E (Nikon Instruments Inc.; Melville, N.Y.).

IV. Diagnostic Applications

The antibodies described herein specifically bind TIM3 and TIM3-expressing cells. The TIM3-specific antibodies can thus be used for in vitro and in vivo diagnostic assays to detect TIM3-expressing cells (e.g., CSCs, certain solid tumor cells, and hematopoietic cancer cells as indicated herein). For example, a sample (e.g., blood sample or tissue biopsy) can be obtained from a patient and contacted with a TIM3 antibody, and the presence of a TIM3 expressing cell in the patient sample can be determined by detecting antibody binding. Antibody binding can be detected directly (e.g., where the antibody itself is labeled) or by using a second detection agent, such as a secondary antibody. The detectable label can be associated with an antibody of the invention, either directly, or indirectly, e.g., via a chelator or linker.

In some embodiments, the anti-TIM3 antibody is contacted with a biological sample from an individual having or suspected of having a TIM3 associated disorder, and antibody binding to a cell in the sample is determined, wherein higher or lower than normal antibody binding indicates that the individual has a TIM3 associated disorder. In some embodiments, the biological sample is a blood sample or blood fraction (e.g., serum, plasma, platelets, red blood cells, white blood cells). In some embodiments, the biological sample is a tissue sample (biopsy), e.g., from a suspected tumor site, or from a tissue that is known to be affected, e.g., to determine the boundaries of a known tumor. In some embodiments, the biological sample is obtained from a site of inflammation.

Biopsies are typically performed to obtain samples from tissues, i.e., non-fluid cell types. The biopsy technique applied will depend on the tissue type to be evaluated (e.g., breast, skin, colon, prostate, kidney, lung, bladder, lymph node, liver, bone marrow, airway or lung). In the case of a cancer the technique will also depend on the size and type of the tumor (e.g., solid, suspended, or blood), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally obtains a suspension of cells from within the tumor mass. Biopsy techniques are discussed, for example, in *Harrison's Principles of Internal Medicine*, Kasper, et al., eds., 16th ed., 2005, Chapter 70, and throughout Part V.

Any method of detecting antibody binding to a cell in a sample can be used for the present diagnostic assays. Methods of detecting antibody binding are well known in the art, e.g., flow cytometry, fluorescent microscopy, ELISAs, etc. In some embodiments, the method comprises preparing the biological sample for detection prior to the determining step. For example, a subpopulation of cells (e.g., white blood cells) can be separated from the rest of the sample from the individual (e.g., other blood components) or cells in a tissue can be suspended for easier detection.

In some embodiments, the percentage of TIM3-expressing cells in the sample is determined and compared to a control, e.g., a sample from an individual or group of individuals that are known to have a TIM3 associated disorder (positive control) or from an individual or group of individuals that are known not to have a TIM3 associated disorder (normal, non-disease, or negative control). In some embodiments, the control is a standard range of TIM3 expression established for a given tissue. A higher or lower than normal percentage of TIM3 expressing cells, or higher or lower expression level, indicates that the individual has a TIM3 associated disorder.

In some embodiments, a labeled anti-TIM3 antibody can be provided (administered) to an individual to determine the applicability of an intended therapy. For example, a labeled antibody may be used to detect TIM3 density within a diseased area, where the density is typically high relative to non-diseased tissue. A labeled antibody can also indicate that the diseased area is accessible for therapy. Patients can thus be selected for therapy based on imaging results. Anatomical characterization, such as determining the precise boundaries of a cancer, can be accomplished using standard imaging techniques (e.g., CT scanning, MRI, PET scanning, etc.).

In some embodiments, labeled TIM3 specific antibodies as described herein can be further associated with a therapeutic compound, e.g., to form a "theranostic" composition. For example, an anti-TIM3 antibody described herein can be linked (directly or indirectly) to both a detectable label and a therapeutic agent, e.g., a cytotoxic agent to kill TIM3-expressing cancer cells. In some embodiments, a labeled TIM3 specific antibody is used for diagnosis and/or localization of a TIM3 expressing cancer cell, and the TIM3 expressing cancer cell is then targeted with a separate therapeutic TIM3 specific antibody. In some embodiments, the diagnostic TIM3 specific antibody is one that is not internalized into TIM3 expressing cells at a high rate or percentage. In some embodiments, the therapeutic TIM3 specific antibody is internalized into TIM3 expressing cells at a high rate or percentage (e.g., a higher rate than the 2E2 antibody, e.g., 1.7E10, 8.16C10, 27.2H4, 6.14B9), and is conjugated to a cytotoxic agent. In some embodiments, the therapeutic TIM3 specific antibody is an antibody that inhibits proliferation of TIM3 expressing cells upon cross-linking or multimerization (e.g., 1.7E10 or 7.10F6).

A. Labels

A diagnostic agent comprising an anti-TIM3 antibody can include any diagnostic agent known in the art, as provided, for example, in the following references: Armstrong et al., *Diagnostic Imaging*, 5$^{th}$ Ed., Blackwell Publishing (2004); Torchilin, V. P., Ed., *Targeted Delivery of Imaging Agents*, CRC Press (1995); Vallabhajosula, S., *Molecular Imaging: Radiopharmaceuticals for PET and SPECT*, Springer (2009). A diagnostic agent can be detected by a variety of ways, including as an agent providing and/or enhancing a detectable signal. Detectable signals include, but are not limited to, gamma-emitting, radioactive, echogenic, optical, fluorescent, absorptive, magnetic, or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like. The terms "detectable agent," "detectable moiety," "label," "imaging agent," and like terms are used synonymously herein.

In some embodiments, the label can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives. Fluorescent dyes are discussed, for example, in U.S. Pat. Nos. 4,452,720, 5,227,487, and 5,543,295.

The label can also be a radioisotope, e.g., radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Co, $^{64}$Co, $^{67}$Co, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In some embodiments, radioactive agents can include $^{111}$In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In some embodiments, the agents can include DOTA and its various analogs with $^{111}$In, $^{177}$Lu, $^{153}$Sm, $^{88/90}$Y, $^{62/64/67}$Cu or $^{67/68}$Ga. In some embodiments, a nanoparticle can be labeled by incorporation of lipids attached to chelates, such as DTPA-lipid, as provided in the following references: Phillips et al., *Wiley Interdisciplinary Reviews: Nanomedicine and Nanobiotechnology*, 1(1): 69-83 (2008); Torchilin, V. P. & Weissig, V., Eds. *Liposomes 2nd Ed.*: Oxford Univ. Press (2003); Elbayoumi, T. A. & Torchilin, V. P., *Eur. J. Nucl. Med. Mol. Imaging* 33:1196-1205 (2006); Mougin-Degraef, M. et al., *Int'l J. Pharmaceutics* 344:110-117 (2007).

In some embodiments, the diagnostic agent can be associated with a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Secondary binding ligands include, e.g., biotin and avidin or streptavidin compounds as known in the art.

In some embodiments, the labeled antibody can be further associated to a composition that improves stability in vivo, e.g. PEG or a nanoparticle such as a liposome, as described in more detail below.

B. Methods of Labeling

Techniques for conjugating detectable and therapeutic agents to antibodies are well known (see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)).

Typically, the antibody is attached to detectable moiety in an area that does not interfere with binding to the epitope. Thus in some cases, the detectable moiety is attached to the constant region, or outside the CDRs in the variable region. One of skill in the art will recognize that the optimal position for attachment may be located elsewhere on the antibody, so the position of the detectable moiety can be adjusted accordingly. In some embodiments, the ability of the antibody to associate with the epitope is compared before and after attachment to the detectable moiety to ensure that the attachment does not unduly disrupt binding.

In some embodiments, the antibody can be associated with an additional targeting moiety. For example, an antibody fragment, peptide, or aptamer that binds a different site on the target molecule or target cell can be conjugated to the antibody to optimize target binding, e.g., to a cancer cell.

V. Therapeutic Applications

TIM3 is aberrantly expressed in a number of disease states, and the TIM3-expressing cells in such conditions can be targeted using the TIM3-specific antibodies described herein. TIM3 expression is elevated on cancer cells (e.g., B cell lymphoma, AML cells, and solid tumor cells described herein) and CSCs (e.g., myeloid CSCs). TIM3 is not significantly expressed on normal hematopoietic stem cells (HSCs). A rapidly-internalized TIM3-targeted therapeutic antibody is particularly valuable in the case of myeloma, which has a very high rate of recurrence, though, as described herein, the present antibodies are useful for targeting and killing other TIM3-expressing cancers. As noted above, a therapeutic composition comprising an anti-TIM3 antibody can further include a detectable label to form a theranostic composition, e.g., for detection and localization of TIM3 expressing cells, and monitoring of therapeutic effect.

A. Chemotherapeutic and Cytotoxic Agents

As demonstrated herein, anti-TIM3 antibodies can inhibit cancer cell growth (proliferation), and thus can be considered chemotherapeutic agents. The following disclosure provides examples of chemotherapeutic and cytotoxic agents that can be linked to an anti-TIM3 antibody for delivery to TIM3-expressing cells.

A chemotherapeutic (anti-cancer) agent can be any agent capable of reducing cancer growth, interfering with cancer cell replication, directly or indirectly killing cancer cells, reducing metastasis, reducing tumor blood supply, etc. Chemotherapeutic agents thus include cytotoxic agents. Cytotoxic agents include but are not limited to saporin, taxanes, vinca alkaloids, anthracycline, and platinum-based agents. Classes of chemotherapeutic agents include but are not limited to alkylating agents, antimetabolites, e.g, methotrexate, plant alkaloids, e.g., vincristine, and antibiotics, e.g., doxorubicin as well as miscellaneous drugs that do not fall in to a particular class such as hydroxyurea. Platinum-based drugs, exemplified by cisplatin and oxaliplatin, represent a major class of chemotherapeutics. These drugs bind to DNA and interfere with replication. Taxanes, exemplified by taxol, represent another major class of chemotherapeutics. These compounds act by interfering with cytoskeletal and spindle formation to inhibit cell division, and thereby prevent growth of rapidly dividing cancer cells. Other chemotherapeutic drugs include hormonal therapy.

Chemotherapeutics currently used for treating myeloma include bortezomib, lenalidomide, and thalidomide. Additional therapeutic agents that can be administered to myeloma patients include bisphosphonates (to prevent bone fractures) and erythropoietin (to reduce anemia).

More than one therapeutic agent can be combined, either in the same composition, or in separate compositions. The therapeutic agent(s) can also be combined with additional therapeutic agents as appropriate for the particular individual. Common therapeutic agents provided to cancer patients include medications to address pain, nausea, anemia, infection, inflammation, and other symptoms commonly experienced by cancer patients.

B. Methods of Forming Therapeutic Compositions

Antibodies can be attached to a therapeutic agent, detectable agent, or nanocarrier using a variety of known cross-linking agents. Methods for covalent or non-covalent attachment of polypeptides are well known in the art. Such methods may include, but are not limited to, use of chemical cross-linkers, photoactivated cross-linkers and/or bifunctional cross-linking reagents. Exemplary methods for cross-linking molecules are disclosed in U.S. Pat. No. 5,603,872 and U.S. Pat. No. 5,401,511. Non-limiting examples of cross-linking reagents include glutaraldehyde, bifunctional oxirane, ethylene glycol diglycidyl ether, carbodiimides such as 1-ethyl-3-(3-dimethylaminopropyl) carbodiimide or dicyclohexylcarbodiimide, bisimidates, dinitrobenzene, N-hydroxysuccinimide ester of suberic acid, disuccinimidyl tartarate, dimethyl-3,3'-dithio-bispropionimidate, azidoglyoxal, N-succinimidyl-3-(2-pyridyldithio)propionate and 4-(bromoadminoethyl)-2-nitrophenylazide.

For antibodies conjugated to nanocarriers (e.g., liposomes), a certain number of antibodies will be present on the surface, i.e., at a given surface density. In some embodiments, the nanocarrier will have at least 5 antibodies per nanocarrier, e.g., at least 10, 30, 40, 50, 75, 100 or higher antibodies per nanocarrier. One of skill in the art will understand that surface density represents an average range, as the number of antibodies per nanocarrier will not be absolutely uniform for all members of the population.

Nanocarriers include vesicles such as liposomes and micelles, as well as polymeric nanoparticles, etc. Nanocarriers are useful for delivery of therapeutic and diagnostic agents, but can be particularly useful for shielding cytotoxic agents used to treat cancer. The nanocarrier can comprise lipids (e.g., phospholipids), hydrophilic polymers, hydrophobic polymers, amphipatic compounds, cross-linked polymers, and a polymeric matrix (see, e.g., WO2009/110939). Depending on the application, the nanocarrier can be designed to have a particular size, half-life, shelf life, and leakage rate.

Preparation of nanocarriers, such as an antibody targeted liposome, polymeric nanoparticle, or extended shelf-life liposome, is described, e.g., in U.S. Pat. Nos. 6,465,188, 7,122,202, 7,462,603 and 7,550,441.

In some embodiments, the antibody is linked to a stabilizing moiety such as PEG, or a liposome or other nanocarrier. U.S. Pat. Nos. 4,732,863 and 7,892,554 and Chattopadhyay et al. (2010) Mol Pharm 7:2194 describe methods for attaching the selected antibody to PEG, PEG derivatives, and nanoparticles (e.g., liposomes). Liposomes containing phosphatidyl-ethanolamine (PE) can be prepared by established procedures as described herein. The inclusion of PE provides an active functional site on the liposomal surface for attachment.

The antibody conjugate can also be formulated to provide more than one active compound, e.g., additional chemotherapeutic or cytotoxic agents, cytokines, or growth inhibitory agents. The active ingredients may also prepared as sustained-release preparations (e.g., semi-permeable matrices of solid hydrophobic polymers (e.g., polyesters, hydrogels (for example, poly (2-hydroxyethyl-methacrylate), or poly (vinylalcohol)), polylactides. The antibodies and immunoconjugates can be entrapped in a nanoparticle prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nanoparticles and nanocapsules) or in macroemulsions.

VI. Methods of Administration

The anti-TIM3 antibodies of the invention can efficiently deliver a therapeutic composition to TIM3-expressing cells in vivo. In some embodiments, the method of treatment comprises administering to an individual an effective amount of a therapeutic anti-TIM3 conjugate, e.g., an anti-TIM3 antibody attached to a therapeutic agent. In some embodiments, the individual has been diagnosed with cancer. In some embodiments, the individual is receiving or has received cancer therapy, e.g., surgery, radiotherapy, or chemotherapy. In some embodiments, the individual has been diagnosed, but the cancer is in remission.

In some embodiments, the anti-TIM3 conjugate includes a liposome. In some embodiments, the method further comprises monitoring the individual for progression of the cancer. In some embodiments, the dose of the anti-TIM3 conjugate for each administration is determined based on the therapeutic progress of the individual, e.g., where a higher dose of chemotherapeutic is administered if the individual is not responding sufficiently to therapy.

In some embodiments, the invention can include an antibody or antibody-targeted composition and a physiologically (i.e., pharmaceutically) acceptable carrier. The term "carrier" refers to a typically inert substance used as a diluent or vehicle for a diagnostic or therapeutic agent. The term also encompasses a typically inert substance that imparts cohesive qualities to the composition. Physiologically acceptable carriers can be liquid, e.g., physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Since physiologically acceptable carriers are determined in part by the particular composition being administered as well as by the particular method used to administer the composition, there are a wide variety of suitable formulations of pharmaceutical compositions of the present invention (See, e.g., Remington's Pharmaceutical Sciences, 17$^{th}$ ed., 1989).

The compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate. Sugars can also be included for stabilizing the compositions, such as a stabilizer for lyophilized antibody compositions.

Dosage forms can be prepared for mucosal (e.g., nasal, sublingual, vaginal, buccal, or rectal), parenteral (e.g., subcutaneous, intravenous, intramuscular, or intraarterial injection, either bolus or infusion), oral, or transdermal administration to a patient. Examples of dosage forms include, but are not limited to: dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Injectable (e.g., intravenous) compositions can comprise a solution of the antibody or antibody-targeted composition suspended in an acceptable carrier, such as an aqueous carrier. Any of a variety of aqueous carriers can be used, e.g., water, buffered water, 0.4% saline, 0.9% isotonic saline, 0.3% glycine, 5% dextrose, and the like, and may include glycoproteins for enhanced stability, such as albumin, lipoprotein, globulin, etc. Often, normal buffered saline (135-150 mM NaCl) will be used. The compositions can contain pharmaceutically acceptable auxiliary substances to approximate physiological conditions, such as pH adjusting and buffering agents, tonicity adjusting agents, wetting agents, e.g., sodium acetate, sodium lactate, sodium chloride, potassium chloride, calcium chloride, sorbitan monolaurate, triethanolamine oleate, etc. In some embodiments, the antibody-targeted composition can be formulated in a kit for intravenous administration.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, topically, intraperitoneally, intravesically, or intrathecally. Parenteral administration and intravenous administration are the preferred methods of administration. The formulations of targeted compositions can be presented in unit-dose or multi-dose sealed containers, such as ampoules and vials.

The targeted delivery composition of choice, alone or in combination with other suitable components, can be made into aerosol formulations ("nebulized") to be administered via inhalation. Aerosol formulations can be placed into pressurized acceptable propellants, such as dichlorodifluoromethane, propane, and nitrogen.

The pharmaceutical preparation can be packaged or prepared in unit dosage form. In such form, the preparation is subdivided into unit doses containing appropriate quantities of the active component, e.g., according to the dose of the therapeutic agent or concentration of antibody. The unit dosage form can be a packaged preparation, the package containing discrete quantities of preparation. The composition can, if desired, also contain other compatible therapeutic agents.

The antibody (or antibody-targeted composition) can be administered by injection or infusion through any suitable route including but not limited to intravenous, subcutaneous, intramuscular or intraperitoneal routes. An example of administration of a pharmaceutical composition includes storing the antibody at 10 mg/ml in sterile isotonic aqueous saline solution for injection at 4° C., and diluting it in either 100 ml or 200 ml 0.9% sodium chloride for injection prior to administration to the patient. The antibody is administered by intravenous infusion over the course of 1 hour at a dose of between 0.2 and 10 mg/kg. In other embodiments, the antibody is administered by intravenous infusion over a period of between 15 minutes and 2 hours. In still other embodiments, the administration procedure is via sub-cutaneous bolus injection.

The dose of antibody is chosen in order to provide effective therapy for the patient and is in the range of less than 0.1 mg/kg body weight to about 25 mg/kg body weight or in the range 1 mg-2 g per patient. In some cases, the dose is in the range 1-100 mg/kg, or approximately 50 mg-8000 mg/patient. The dose may be repeated at an appropriate frequency which may be in the range once per day to once every three months, depending on the pharmacokinetics of the antibody (e.g., half-life of the antibody in the circulation) and the pharmacodynamic response (e.g., the duration of the therapeutic effect of the antibody). In some embodiments, the in vivo half-life of between about 7 and about 25 days and antibody dosing is repeated between once per week and once every 3 months.

Administration can be periodic. Depending on the route of administration, the dose can be administered, e.g., once every 1, 3, 5, 7, 10, 14, 21, or 28 days or longer (e.g., once every 2, 3, 4, or 6 months). In some cases, administration is more frequent, e.g., 2 or 3 times per day. The patient can be monitored to adjust the dosage and frequency of administration depending on therapeutic progress and any adverse side effects, as will be recognized by one of skill in the art.

Thus in some embodiments, additional administration is dependent on patient progress, e.g., the patient is monitored between administrations. For example, after the first administration or round of administrations, the patient can be monitored for rate of tumor growth, recurrence (e.g., in the case of a post-surgical patient), or general disease-related symptoms such as weakness, pain, nausea, etc.

In therapeutic use for the treatment of cancer, an antibody-targeted composition (e.g., including a therapeutic and/or diagnostic agent) can be administered at the initial dosage of about 0.001 mg/kg to about 1000 mg/kg daily and adjusted over time. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosage is varied depending upon the requirements of the patient, the severity of the condition being treated, and the targeted composition being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a particular targeted composition in a particular patient, as will be recognized by the skilled practitioner.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entireties for all purposes.

VII. Examples

A. Example 1: TIM3-Specific Antibodies

Female Balb/C mice were immunized with recombinant human TIM3-Fc fusion protein four times. Two days after final injection, spleen and lymph node cells were fused with SP2/O cells using PEG and selected in HAT medium. Hybridomas were screened by ELISA for reactivity against recombinant TIM3 protein and positive cultures were confirmed by flow cytometry for recognition of TIM3 expressing cell lines. Selected hybridoma were subcloned by limiting dilution or single cell sorting. Subclones were confirmed by flow cytometry for binding to TIM3. Heavy chain and light chain variable region sequences were amplified using reverse transcriptase polymerase chain reaction (RT-PCR) with specific primers. cDNA products were then sequenced. Table 1 (SEQ ID NOS:3-5, 8-10; 13-15, 18-20; 23-25, 28-30; 73-75, 78-80; 83-85, 88-90; 93-95, 98-100; 103-105, 108-110; 33-35, 38-40; 43-45, 48-50; 53-55, 58-60; 63-65, 68-70; 113-115, 118-120) profiles the selected antibodies, e.g., for isotype and CDR sequences.

TABLE 1

| Hybridoma | Isotype | VH | DH | JH | VK | JK | CDRH1 |
|---|---|---|---|---|---|---|---|
| 1.7E 10 | IgG1,k | IGHV4-1*02 | DSP.9 | JH4 | IGKV3-5*01 | JK2 | GFDFSRYW |
| 7.10F6 | IgG1,k | IGHV5-6-3*01 | DSP2.10 | JH4 | IGKV8-27*01 | JK2 | GFIFSGYG |
| 8.16C10 | IgG1,k | IGHV1-11*02 | DSP2.4 | JH4 | IGKV4-79*01 | JK2 | GYTFTDYY |
| 33.1G12 | IgG1,k | IGHV1-20*02 | DSP2.2 | JH4 | IGKV3-5*01 | JK1 | GYSFTGYL |
| 33.2A5 | IgG1,k | VHJ558 | IGHD2-14*01 | JH4 | IGKV3-4*01 | JK2 | GYTSNYNW |
| 33.14A5 | IgG1,k | J558.46 | DSP2.8 | JH3 | Igk-V4/5 | JK5 | GYTFTSYW. |
| 27.12 E12 | IgG2b,k | IGHV14-1*02 | DFL16.2 | JH1 | IGKV6-15*01 | JK2 | GFNIKDYY |
| 27.2H4 | IgG1,k | IGHV14-1*02 | DST4.3 | JH4 | IGKV6-17*01 | JK1 | GFNIKHYY |
| 27.12A6 | IgG1,k | IGHV5-12-2*01 | DSP2.8 | JH4 | IGKV8-27*01 | JK1 | GFTFSSYT |
| 6.14B9 | IgG1,k | IGHV3-2*03 | DSP2.6 | JH2 | IGKV9-124*01 | JK5 | GYSITSDYA |
| 6.16F9 | IgG1,k | IGHV5-12-2*01 | DSP2.8 | JH4 | IGKV8-27*01 | JK1 | GFTFSSYT |
| 9.1G12 | IgG2b,l | IGHV5S9*01, | DSP2.12 | JH3 | | Jk5 | GFTFSSYA |

| Hybridoma | CDRH2 | CDRH3 | CDRL1 | CDRL2 | CDRL3 |
|---|---|---|---|---|---|
| 1.7E 10 | INPDSSTI | ARPSYDGYYGYAMDY | ESVDSYGKSF | RAS | QQSNEDPYT |
| 7.10F6 | INSNGGSV | ARIYYRCMDY | QSLLYSSNQKNY | WAS | HQYLSSYT |
| 8.16C10 | IYPGSGIT | AIYGYDGGYAMDY | SSVSSSY | STS | HQWSTYPYT |
| 33.1G12 | INPYNGDI | ARRDENFDYDNAMDY | ESVDIYGNSF | RAS | QQSNEDPWT |
| 33.2A5 | INPATGYT | TTGRNDEGGYALDS | QSVDHAGDSY | GAS | QQSNEDPYT |
| 33.14A5 | IDPSKSET | AQYGNHVLLLTGAKGHRSLSLH | SSVSSNY | STS | QLYSGYPLT |
| 27.12 E12 | IDPENVKT | TRDFGYVGFFDV | QNVGTN | SAS | QQYNSYPLT |
| 27.2H4 | IDPETGNT | ARGWSYAMDY | QDVNTA | SAS | QQHYSTPWT |
| 27.12A6 | ISSGGHST | ARGGYGNYGPYYNMDY | QSVLYSSNQKNY | WAS | HQYLSSWT |
| 6.14B9 | ISYSGSI | ARSGRLRRDFDY | QEISGY | AAS | LQYASYPLT |
| 6.16F9 | TSSSGAST | ARGGYGNYGPYYALDY | QSVLYSSNQKNY | WAS | HQYLSSWT |
| 9.1G12 | ISSGGTYT | VRPDYTHDDGGFAY | QGISNN | DAS | LQHRYLPHVRCW |

The polynucleotide and protein sequences for the heavy and light chain variable regions are provided in the sequence listing.

B. Example 2: Binding Profile for TIM3-Specific Antibodies

The binding profile of the selected TIM3-specific antibodies was tested on various TIM3-expressing cell lines. Table 2 shows the percentage of cell binding of the indicated antibodies to Pfeiffer cells, Daudi cells, and CMK cells. TIM3 2E2 is an antibody commercially available from eBioscience®, San Diego, Calif. (see, e.g., the website and catalog available at ebioscience.com, catalog number 17-3109, Hastings et al. (2009) *Eur. J. Immunol.* 39:2492).

TABLE 2

Profile of Tim3-specific antibody binding to myeloid and lymphoma cell lines

| Cell Line | Disease | 1.7E10 | 7.10F6.1 | 8.16C10 | 9.1G12 | 27.2H4 | 27.12E12 | Tim3 2E2 |
|---|---|---|---|---|---|---|---|---|
| Pfeiffer | Non Hodgkin's Lymphoma. Diffuse large B cell Lymphoma | 97% (Geomean = 439) 91% | 92% | 85% | 14% | 75% | 97% (Geomean = 458) | 97% (Geomean = 308) |
| Daudi | Burkitt's Lymphoma | 95% 97% | 98% | 67% | Neg. | 46% | 92% | 90% |

TABLE 2-continued

Profile of Tim3-specific antibody binding to myeloid and lymphoma cell lines

| Cell Line | Disease | 1.7E10 | 7.10F6.1 | 8.16C10 | 9.1G12 | 27.2H4 | 27.12E12 | Tim3 2E2 |
|---|---|---|---|---|---|---|---|---|
| CMK | Acute megakaryocytic leukemia. AML-M7 | 32% | ND | ND | 2% | Neg. | 18% | 19% |

The TIM3-specific antibodies were also tested for binding to peripheral blood cells from a normal (non-cancer) donor. As shown for 1.7E10 in FIG. 1, the antibodies do not bind significantly to mature peripheral blood cells, with the exception of low level binding to a small population of monocytes.

C. Example 3: Binding of TIM3-Specific Antibodies to Cancer Patient Samples

Figure 2:
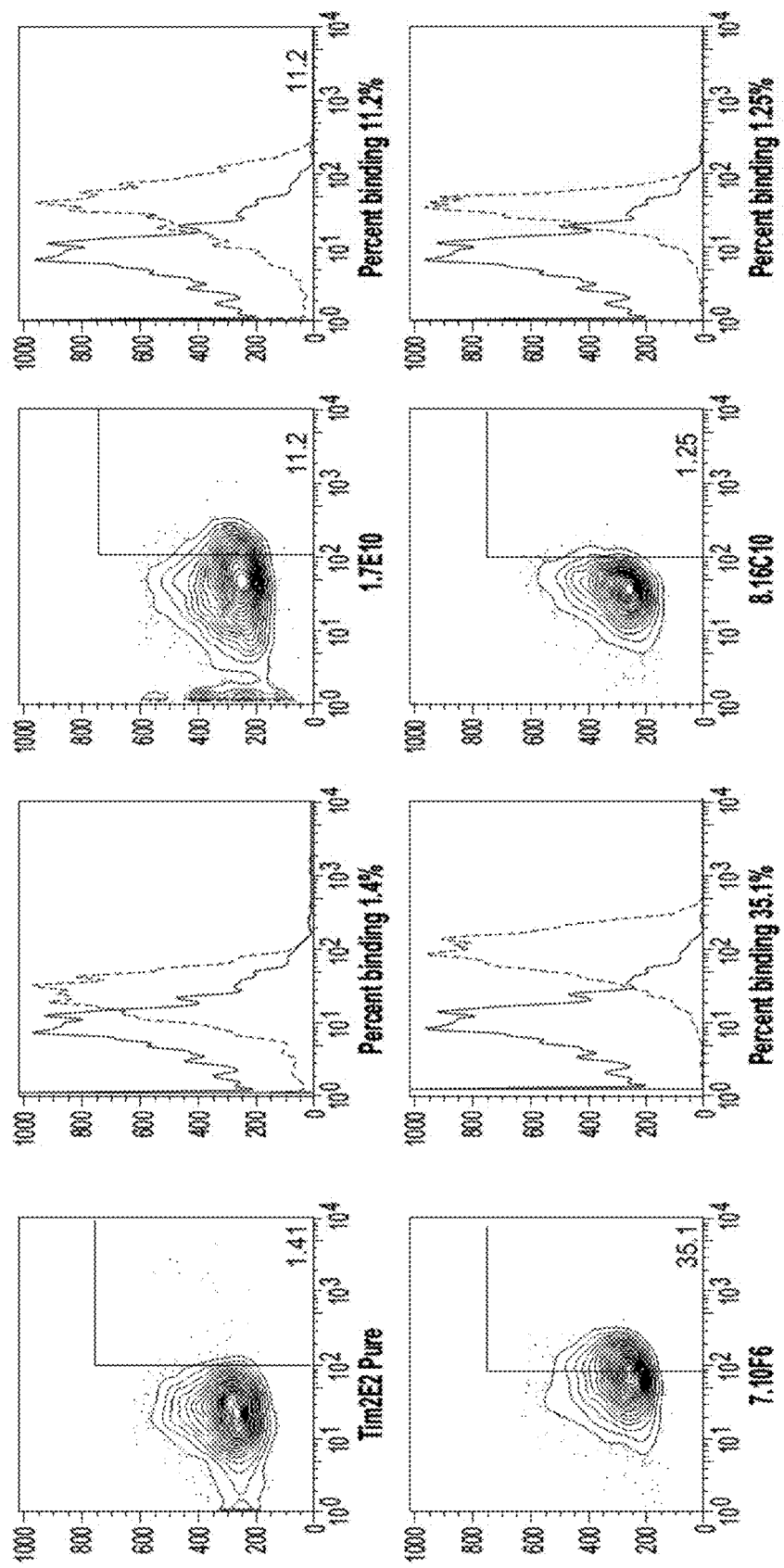
FIG. 2. The presently disclosed TIM3-specific antibodies bind more PBMCs from AML patients at a higher level than commercially available 2E2 antibody. PBMCs were stained with the indicated antibody and gated for live cells. The negative controls were negative for staining (goat anti-mouse IgG (GaMsIgG) and mouse IgG1 (msIgG1)).

In contrast to the lack of binding to normal peripheral blood cells, the Tim3-specific antibodies bind at a high level to AML cells from patient samples. FIG. 2 compares the peripheral blood binding profiles of Isotype control (msIgG1) and 2E2 antibodies to those for the 1.7E10, 7.10F6, and 8.16C10 antibodies. The 1.7E10.7 and 7.10F6 bind to significantly more cells, with higher fluorescence, than the commercially available antibody. The 8.16C10 antibody binds about the same number of cells as 2E2 at a slightly higher fluorescence.

Table 3 shows the binding profiles for peripheral blood from five different AML patient samples. In this case, the peripheral blood was separated into stem cell (CD34+ CD38−) and blast cells. Table 4 shows the binding profiles for these populations obtained from bone marrow.

D. Example 4: Internalization of TIM3-Specific Antibodies

The TIM3-specific antibodies were tested for internalization into TIM3-expressing cells (Pfeiffer B lymphoma cells). Pfeiffer cells were blocked with ice-cold PBS+3% human serum, followed by pre-incubation for 20 minutes at 4 C with the TIM3-specific antibodies or their corresponding isotype controls. Most of the TIM3-specific antibodies disclosed here are IgG1, though 27.12E12 is IgG2b. The cells were washed 3× with PBS and split into two sets for 20 minute incubations. The first set was incubated at 4 C, where internalization occurs at a very low level if at all, while the second set was incubated at 37 C. After incubation, the cells were washed with PBS and incubated with goat anti-mouse PE.

Figure 3:
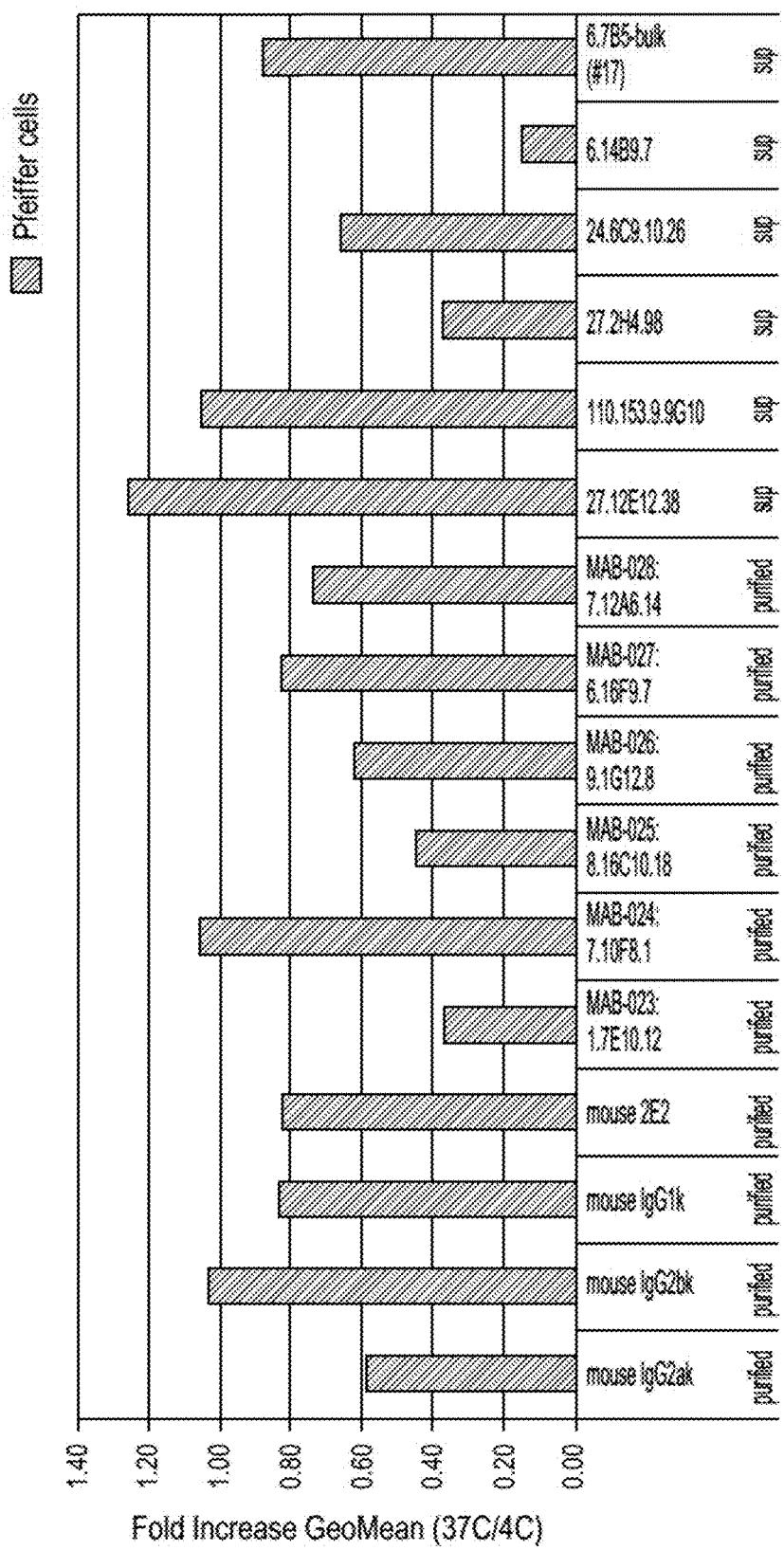
FIG. 3. The presently disclosed TIM3-specific antibodies are internalized into TIM3 expressing Pfeiffer cells at a high level. Results for isotype controls are indicated in the first three lanes, for the commercially available 2E2 antibody in lane 4, and for the presently disclosed antibodies in lanes 5-16.

FIG. 3 shows the results, expressed as a ratio of cell surface staining at 37 C/cell surface staining at 4 C. Thus, the more internalization, the lower the ratio. From the results shown in FIG. 3, the 1.7E10, 8.16C10, 9.1G12, 27.2H4, 24.6C9.10, and 6.14B9 antibodies show significant levels of internalization. In particular, more than 50% of the 1.7E10, 8.16C10, 27.2H4, and 6.14B9 antibodies are internalized after 20 minutes.

E. Example 5: Use of TIM3-Specific Antibodies for Antibody Drug Conjugates (ADC)

Given the internalization results, the TIM3-specific antibodies were also tested for ability to kill TIM3-expressing

TABLE 3

Percent binding of TIM3-specific antibodies to PBMCs from AML patients

| ID | Population | Diagnosis | 1.7E10 | 7.10F6 | 8.16C10 | 27.12E12 | 27.2H4 | 9.1G12 | TIM3 2E2 |
|---|---|---|---|---|---|---|---|---|---|
| 1 | Blast | AML with | 18.31% | 13.49% | 3.13% | N/A | N/A | N/A | 2.92% |
|   | CD34+CD38− | myelodysplasia-related change | 25.34% | 18.70% | 4.67% | N/A | N/A | N/A | 3.26% |
| 2 | Blast | AML with | 0.24% | 78.74% | 68.09% | N/A | N/A | N/A | 59.34% |
|   | CD34+CD38− | myelodysplasia-related change | 0.19% | 85.78% | 76.43% | N/A | N/A | N/A | 64.78% |
| 3 | Blast | unknown | 3.89% | 1.33% | 0.83% | 27.86% | 1.07% | 0.67% | 1.01% |
|   | CD34+CD38− |  | 1.00% | 0.60% | 0.49% | 2.66% | 0.69% | 0.23% | 0.17% |
| 4 | Blast | AML with | 88% | 94% | 78% | NA | NA | NA | NA |
|   | CD34+CD38− | monocytic differentiation | 94% | 98% | 87% |  |  |  | NA |
| 5 | Blast | Persistent/ | 29% | 49% | 25% | NA | NA | NA | NA |
|   | CD34+CD38− | recurrent AML (MDS/MPD) | 29% | 49% | 25% |  |  |  | NA |

TABLE 4

Percent binding of Tim3-specific antibodies to bone marrow cells from AML patients

| ID | Population | Diagnosis | 1.7E10 | 7.10F6 | 8.16C10 | 27.12E12 | 27.2H4 | 9.1G12 | Tim3 2E2 |
|---|---|---|---|---|---|---|---|---|---|
| 1 | Blast | Persistent/ | 34.79% | 18.96% | 55.59% | NA | NA | NA | NA |
|   | CD34+CD38− | recurrent AML | 5.8% | 8.61% | 19.19% | NA | NA | NA |  |
| 2 | Blast | AML with | 1.52% | 8.37% | 2.61% | NA | NA | NA | 1.80% |
|   | CD34+CD38− | t(8; 21)(q22; q22) | 0.60% | 4.83% | 1.47% | NA | NA | NA | 1.6% | cells when conjugated to a cytotoxic drug. The TIM3-specific antibodies were affinity purified using a Protein G column. The purified antibodies were biotinylated using EZ-link Sulfo NHS-LC-Biotinylated kit (ThermoFisher Scientific). Strepavidin-saporin conjugates (SAv-ZAP) were purchased from Advanced Targeting Systems. Saporin is a potent Type I ribosome inactivating toxin. SAv-ZAP was conjugated to the biotinylated antibodies at room temperature for 45 minutes. Pfeiffer cells were treated with different TIM3-specific antibodies or isotype controls at 5 nM for 72 hours. After 72 hours, cell viability was measured using the DHL™ Cell Cytotoxicity Assay kit. The assay measures released cytoplasmic lactate dehydrogenase (LDH) to determine cell membrane integrity and quantify cytotoxicity.

Figure 4:
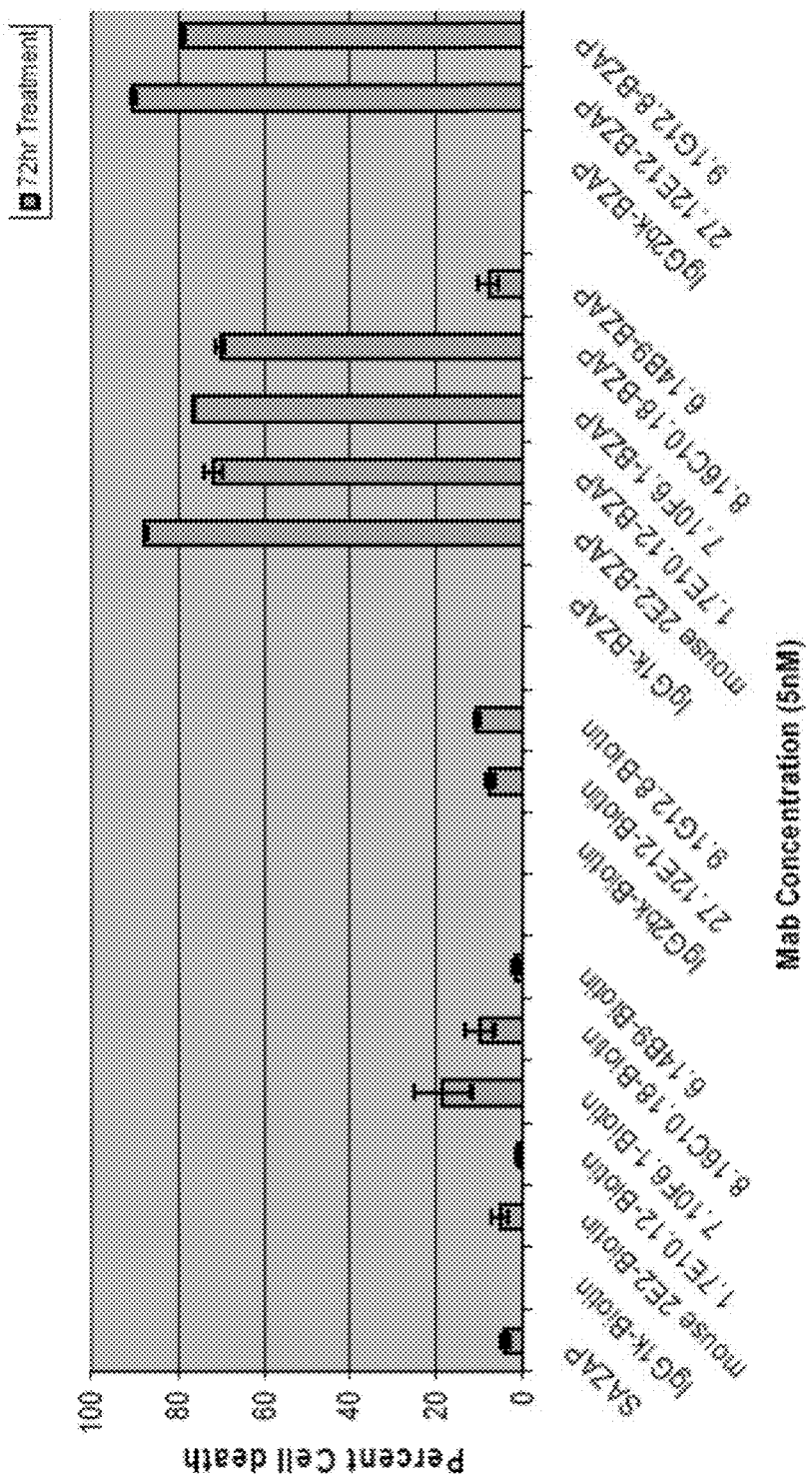
FIG. 4. TIM3-specific antibodies conjugated with saporin effectively kill TIM3-expressing Pfeiffer cells. SAZAP=strepavidin-saporin; Antibody-Biotin=biotin conjugated antibody; Antibody-BZAP=biotinylated, saporin conjugated antibody.

FIG. 4 shows the cytotoxicity results. The antibody-saporin conjugates (ADCs) are designated BZAP. Data are shown are presented as the mean of triplicates with bars showing standard deviation.

The data show that the TIM3-specific antibodies are capable of ADC activity. Of particular interest is the high level of cytotoxicity shown by the 27.12E12-BZAP and 9.1G12-BZAP antibody conjugates, which are of the IgG2 isotype.

Table 5 provides an overview of the data that indicates the level of TIM3 binding and binding profile for the antibodies and antibody conjugates.

TABLE 5

TIM3 binding profiles of antibody conjugates

| Anti- TIM3 antibody IDs | GeoMean (Intensity of TIM3 binding) | % Positive for TIM3 |
|---|---|---|
| Mouse IgG1k-Biotin | 5.06 | 0.192 |
| mouse 2E2-pure | 198 | 89.9 |
| 1.7E10.12-Biotin | 354 | 99.2 |
| 7.10F6.1-pure | 142 | 93.3 |
| 8.16C10.18-pure | 83.8 | 92.5 |
| 6.14B9-Biotin | 20.4 | 48.2 |
| Mouse IgG1k-BZAP | 5.33 | 0.501 |
| 1.7E10.12-BZAP | 436 | 99.3 |
| 6.14B9-BZAP | 22.5 | 43.9 |
| Mouse IgG2ak-Biotin | 5.83 | 0.49 |
| 27.12E12-Biotin | 202 | 96.8 |
| 9.1G12.8-Biotin | 23.1 | 55.4 |
| IgG2bk-BZAP | 6.48 | 0.195 |
| 27.12E12-BZAP | 268 | 98.8 |
| 9.1G12.8-BZAP | 168 | 97.4 |

F. Example 6: TIM3-Specific Antibodies Reduce Cell Proliferation

The TIM3-specific antibodies were tested for ability to reduce cell proliferation of AML cells. TIM3-specific antibodies (or controls) were coated on plates at various concentrations for 2 hours, followed by addition of $10^5$ CMK cells. The cells were incubated at 37 C in RPMI with 20% FBS for three days. FIG. 5 shows that the 1.7E10 and 7.10F6 antibodies, in particular, effectively inhibit AML cell growth.

The results indicate that cross-linking of the antibodies, e.g., by coating the antibodies on cell culture plates or beads, or mulimerizing antibodies into multivalent forms, improves the inhibition of cell growth.

G. Example 7: Complement Dependent Cytotoxicity (CDC) Activity of TIM3-Specific Antibodies A subset of the TIM3-specific antibodies were tested for CDC activity. Human Fc chimeras were generated for the 1.7E10, 7.10F6, and 8.16C10 antibodies. Pfeiffer cells were incubated with human complement and the chimeric antibodies at various concentrations for 45 minutes. Specific lysis was determined by measuring the total number of live cells (see FIG. 6). All of the TIM3-specific chimeric antibodies tested were capable of mediating complement dependent cytotoxicity in a dose-dependent fashion.

H. Example 8: TIM3-Specific Antibodies Inhibit Release of Th1 Cytokines from Activated CD4+ T Cells The TIM3-specific antibodies were tested for their effects on other cell types, namely CD4+ T cells. Fresh, purified PBMC were obtained from healthy donors, and isolated by Ficoll gradient. Naïve CD4+ T cells were isolated by negative selection. The CD4+ T cells were stimulated using CD3 and CD28 antibody-coated Dynabead® beads for 48 hours. TIM3-specific antibodies (or isotype controls) were added at the beginning of the culture at 5 µg/ml.

Following stimulation, Th1 cytokine levels, in particular, IL-6 and IFN-gamma, were tested by ELISA (using antibodies from eBioscience®). The results are shown in FIG. 7. Cytokine levels are shown relative to isotype controls, which are arbitrarily set at 1.0. Several of the TIM3-3 specific antibodies reduced the amount of inflammatory cytokine release from the activated T cells. For IFN-gamma, 1.7E10, 7.10F6, and 8.16C10 were particularly effective (>2-fold reduction compared to control). For IL-6, 8.16C10 and 9.1G12 were particularly effective (>2 fold reduction compared to control).

I. Example 9: TIM3 is Expressed on Solid Tumor Cells

A database of Affymetrix microarray gene expression studies indicated that TIM3 is expressed at an elevated level in certain solid tumor cells compared to normal, non-cancer cells of the same type. As expected, TIM3 was detected at a high frequency in AML and other hematopoietic cell cancer samples. Unexpectedly, a high level of TIM3 expression was also found at high frequency in the following diseased samples (number of samples showing HAVCR2 over-expression compared to control/number of samples analyzed).

| Burkitt's lymphoma | 4/4 |
| Myelodysplastic syndrome | 124/193 |
| Chronic myelodysplastic syndrome | 2/2 |
| Hodgkin's lymphoma | 5/5 |
| Colon carcinoma | 4/4 |
| Ovarian carcinoma | 4/4 |
| Liver carcinoma | 3/4 |
| Prostate carcinoma | 4/4 |
| Uterine carcinoma | 4/4 |
| Breast carcinoma | 4/4 |
| Renal carcinoma | 4/4 |

These results show that the TIM3 specific antibodies disclosed herein can be used to target solid tumor cells, as well as hematopoietic cancer cells for detection and/or therapy.

J. Example 10: TIM3-Specific Antibodies Bind AML Samples, but do not Bind CD34+ Cells from Normal Individuals Using light scatter properties, blast and CD34+/38− populations were identified in the low side scatter population which constituted gate 1. Gate 2 was drawn around the cells identified by gate 1 that were still viable by propidium iodide. The merge of gate 1 and 2 constituted the live "blast" population. The CD34+/38− population was then identified from the live blast population which was labeled gate 3. The entire CD34+ population was gated rather than the CD34+/38−.

Table 6 shows number of samples that stained positive for TIM3 using the presently-disclosed antibodies, and the percentage of samples labeled. Positivity was determined by at least one TIM3-specific antibody staining by flow cytometry. Samples were broken down into FAB classification (M1-M5, or "Others" if not available) and by sample type (bone marrow BM or peripheral blood PB).

TABLE 6

| Sample type | TIM3 antibody binding |
| --- | --- |
| All AML | 25/56 (45%) |
| M1 | 8/15 |
| M2 | 7/13 |
| M3 | 0/1 |
| M4 | 6/9 |
| M5 | 4/9 |
| Others | 0/9 |
| BM | 4/7 (57%) |
| PB | 21/49 (43%) |

The TIM3-specific antibodies were individually tested for binding to CD34+ cells from a set of AML samples as shown in Table 7.

TABLE 7

| Antibody | 1.7E10.12 | 12E12 | 9.1G12 | 2E2 |
| --- | --- | --- | --- | --- |
| Positive/total | 3/22 | 7/22 | 2/14 | 0/14 |

The staining characteristics were also determined for CD34+ cells from non-cancer (normal) individuals using the 1.7E10.12 and 12E12 TIM3-specific antibodies. Table 8 shows data from normal CD34+ samples. Positivity was determined by flow cytometry against target clonal antibody. Number in each cell indicates MFI (% of cells positive). These data show that the presently disclosed TIM3-specific antibodies have a low likelihood of false positivity.

TABLE 8

| | 1.7E10.12 | 12E12 |
| --- | --- | --- |
| Sample 1 | 1.72 (2.08%) | 1.45 (4.41%) |
| Sample 2 | 0.97 (0.88%) | 1.02 (2.62%) |

K. Example 11: Staining Characteristics of TIM3-Specific Antibodies on Other Hematological Malignancies Binding of the TIM3-specific antibodies was also examined in leukemic and non-leukemic lymphomas. A variety of different subtypes of lymphomas were examined and of the 9 non-leukemic lymphomas tested, 3 were positive (33%). The striking finding was the higher probability of detectable occurrence of TIM3 in leukemic-phase lymphomas where 5 of the 6 samples tested were positive. This mirrored the cell line data collected from Daudi and Pfeiffer cell lines, generated from leukemic-phase lymphomas. Table 9 shows number of samples that stained positive by flow cytometry. Positivity was determined by staining by at least one TIM3-specific antibody. Samples were broken down into subtypes and solid vs leukemic phenotype.

TABLE 9

| Hematological malignancy | TIM3 positive |
| --- | --- |
| Follicular | 1/3 |
| MCL | 1/3 |
| DLBCL | 2/5 |
| CLL/SLL | 2/2 |
| B-ALL | 2/2 |
| Non-leukemic | 3/9 |
| Leukemic | 5/6 |

Figure 8B:
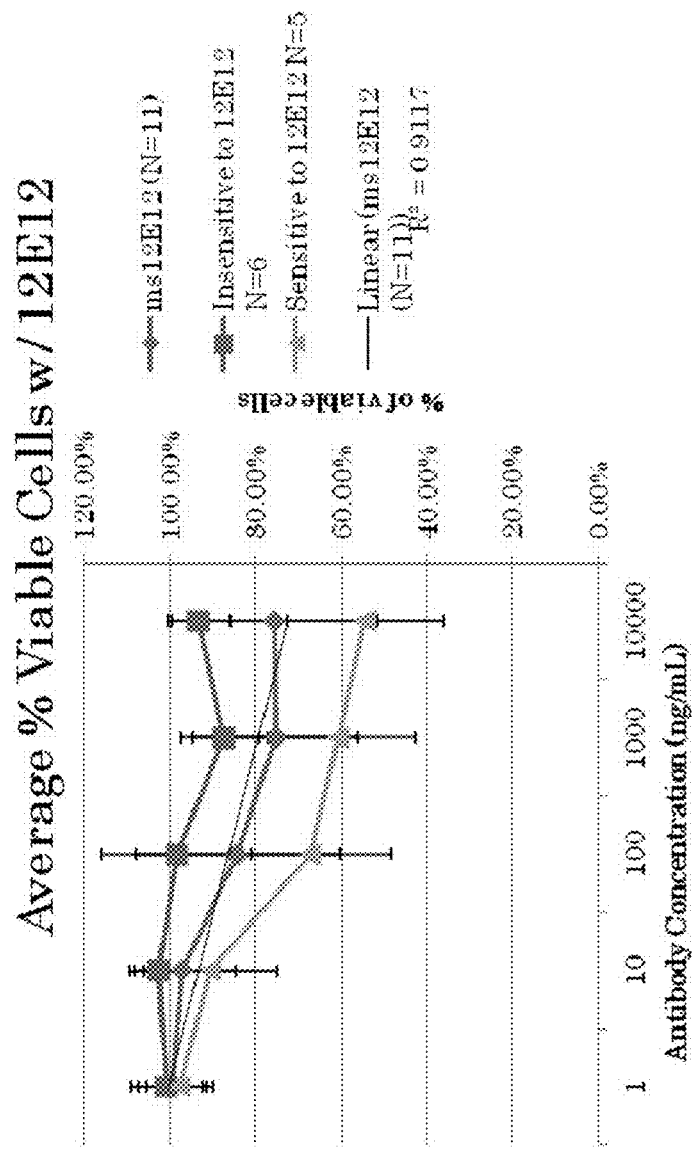

L. Example 12: TIM3-Specific Antibody Clone 12E12 has CDC Activity Against AML Cells from Patient Samples Cells from AML patient samples were washed and dead cells removed using Live-Dead Kit (Miltenyi). Cells were resuspended to a final concentration of $0.8 \times 10^6$/mL. 50 uL of the cell solution was added to each well of a black well, clear bottom 96-well plate (Costar). Two-fold stock antibody solutions (12E12) were prepared at a concentration of 20 ug/mL, 2 ug/mL, 200 ng/mL, 20 ng/mL or 2 ng/mL. 50 uL of the 2× antibody solution was added to each well containing cells allowing the final concentration in the wells to be 10 ug/mL, 1 ug/mL, 100 ng/mL, 10 ng/mL or 1 ng/mL. Cells and antibody were allowed to incubate for 10 minutes at room temperature prior to addition of baby rabbit complement. 1 mL of ice cold water was added to lyophilized complement (Cedarlane) and 10 uL was added to each cell+antibody solution well. Complement was also added to cells only as a cell+complement control. The plate was incubated at 37° C. for 2 hours before allowing to rest at room temperature for 10 minutes. Cell Titre-Glo (Promega) was prepared and 100 uL was added to each well and allowed to shake for 5-10 minutes prior to reading on a luminescent plate reader Eleven AML samples with 12E12-detectable TIM3 expression were used to determine CDC activity of the antibody. FIG. 8A shows that 12E12 CDC activity does not depend on level of TIM3 expression. On the whole, a dose-dependent toxicity curve could be determined (see FIG. 8B, ms12E12). However, several samples seemed to have no CDC activity mediated by 12E12 (FIG. 8B, Insensitive). When the CDC data of those samples were removed, the remaining samples showed a steeper dose-dependent toxicity curve. Standard student t-test was used to identify non-sensitive samples to 12E12 by comparing wells with 12E12 treatment to IgG treatment.

```
INFORMAL SEQUENCE LISTING
SEQ ID NO: 1 - 1.7E10 Heavy chain nucleotide sequence
GAGGTGAAGCTTCTCGAGTCTGGAGGTGGCCTGGTGCAGCCTGGAGGATCCCTGAAACTCTCCTGTGCAG
CCTCAGGATTCGATTTTAGTAGATACTGGATGAGTTGGGTCCGGCAGGCTCCAGGGAAAGGGCTAGAATG
GATTGGAGAAATTAATCCAGATAGCAGTACGATAAACTATACGCCATCTCTAAAGGATAAATTCATCATC
TCCAGAGACAACGCCAAAAATACGCTGTTCCTGCAAATGAGCAAAGTGAGATCTGAGGACACAGCCCTTT
ATTACTGTGCAAGACCGAGCTATGATGGTTACTACGGGTATGCTATGGACTACTGGGGTCAAGGAACCTC
AGTCACCGTCTCCTCA
```

-continued

SEQ ID NO: 2 - 1.7E10 Heavy chain protein sequence
EVKLLESGGGLVQPGGSLKLSCAASGFDFSRYWMSWVRQAPGKGLEWIGEINPDSSTINYTPSLKDKFII
SRDNAKNTLFLQMSKVRSEDTALYYCARPSYDGYYGYAMDYWGQGTSVTVSS

SEQ ID NO: 3 - 1.7E 10 CDRH1
GFDFSRYW

SEQ ID NO: 4 - 1.7E 10 CDRH2
INPDSSTI

SEQ ID NO: 5 - 1.7E 10 CDRH3
ARPSYDGYYGYAMDY

SEQ ID NO: 6 - 1.7E10 Light chain nucleotide sequence
GACATTGTACTGACCCAATCTCCAGCTTCTTTGGCTGTGTCTCTAGGGCAGAGGGCCACCATATCCTGCA
GAGCCAGTGAAAGTGTTGATAGTTATGGCAAGAGTTTTATGCACTGGTACCAGCAGAAACCAGGACAGCC
ACCCAAACTCCTCATCTATCGTGCATCCAACCTAGAATCTGGGATCCCTGCCAGGTTCAGTGGCAGTGGG
TCTAGGACAGACTTCACCCTCACCATTAATCCTGTGGAGGCTGATGATGTTGCAACCTATTACTGTCAGC
AAAGTAATGAGGATCCGTACACGTTCGGAGGGGGGACCAAGCTGGAAATAAAACG SEQ ID NO: 7 - 1.7E10 Light chain protein sequence
DIVLTQSPASLAVSLGQRATISCRASESVDSYGKSFMHWYQQKPGQPPKLLIYRASNLESGIPARFSGSG
SRTDFTLTINPVEADDVATYYCQQSNEDPYTFGGGTKLEIKR

SEQ ID NO: 8 - 1.7E 10 CDRL1
ESVDSYGKSF

SEQ ID NO: 9 - 1.7E 10 CDRL2
RAS

SEQ ID NO: 10 - 1.7E 10 CDRL3
QQSNEDPYT

SEQ ID NO: 11 - 7.10F6 Heavy chain nucleotide sequence
GAGGTGCAGCTGGTGGAGTCTGGGGGAGGCTTAGTGCAGCCTGGAGGGTCCCTGAAGCTCTCCTGTGCAG
CCTCTGGATTCATTTTCAGTGGCTATGGCATGTCTTGGGTTCGCCAGACTCCAGACAAGAGGCTGGAGTT
GGTCGCAATCATTAATAGCAATGGTGGTAGTGTTGATTATCCAGACAGTGTGAAGGGCCGAGTCACCATC
TCCAGAGACAATGCCAAGAACACCCTGTACCTGCAAATGAGCAGTCTGAAGTCTGAGGACACAGCCATGT
ATTACTGTGCAAGAATCTACTATAGATGTATGGACTACTGGGGTCAAGGAACCTCAGTCACCGTCTCCTC
A SEQ ID NO: 12 - 7.10F6 Heavy chain protein sequence
EVQLVESGGGLVQPGGSLKLSCAASGFIFSGYGMSWVRQTPDKRLELVAIINSNGGSVDYPDSVKGRVTI
SRDNAKNTLYLQMSSLKSEDTAMYYCARIYYRCMDYWGQGTSVTVSS

SEQ ID NO: 13 - 7.10F6 CDRH1
GFIFSGYG

SEQ ID NO: 14 - 7.10F6 CDRH2
INSNGGSV

SEQ ID NO: 15 - 7.10F6 CDRH3
ARIYYRCMDY

SEQ ID NO: 16 - 7.10F6 Light chain nucleotide sequence
AACATTATGATGACACAGTCGCCATCATCTCTGGCTGTGTCTGCAGGAGAAAAGGTCACTATGAGTTGTA
AGTCCAGTCAAAGTCTTTTATACAGTTCAAATCAGAAGAACTACTTGGCCTGGTACCAGCAAAAACCAGG
ACAGTCTCCTAAATTGCTGATCTACTGGGCTTCCGCTAGGGAATCTGGTGTCCCTGATCGCTTCACAGGC
GGTGGATCTGGGACAGATTTTACTCTTACCATCAGCAGTGTACAAGCTGAAGACCTGGCAGTTTATTACT
GTCATCAATACCTCTCCTCGTACACGTTCGGAGGGGGGACCAAGCTGGAGATAAAACG SEQ ID NO: 17 - 7.10F6 Light chain protein sequence
NIMMTQSPSSLAVSAGEKVTMSCKSSQSLLYSSNQKNYLAWYQQKPGQSPKLLIYWASARESGVPDRFTG
GGSGTDFTLTISSVQAEDLAVYYCHQYLSSYTFGGGTKLEIKR

SEQ ID NO: 18 - 7.10F6 CDRL1
QSLLYSSNQKNY

SEQ ID NO: 19 - 7.10F6 CDRL2
WAS

SEQ ID NO: 20 - 7.10F6 CDRL3
HQYLSSYT

SEQ ID NO: 21 - 8.16C10 Heavy chain nucleotide sequence
CAGATCCAGCTGCAGCAGTCTGGACCTGAGCTGGTGAAGCCTGGGGCTTCAGTGAAGATATCCTACAAGG
CTTCTGGCTACACCTTCACTGACTACTATATAAACTGGGTGAAGCAGAAGCCTGGACAGGGACTTGAGTG
AGATTGGATGGATTTTCCTGGAAGCGGTATTACTAAGTACAATGAGAAGTTCAAGGGCAAGGCCACATTG
ACTGTAGACTCATCCTCCAGCACAGCCTACATGCAGCTCAGCAGCCTGACATCTGAGGACACTGCTGTCT
ATTTCTGTGCGATATATGGTTACGACGGGGGATATGCTATGGACTACTGGGGTCAAGGAACCTCAGTCAC
CGTCTCCTCA -continued SEQ ID NO: 22 - 8.16C10 Heavy chain protein sequence
QIQLQQSGPELVKPGASVKISYKASGYTFTDYYINWVKQKPGQGLEWIGWIYPGSGITKYNEKFKGKATL
TVDSSSTAYMQLSSLTSEDTAVYFCAIYGYDGGYAMDYWGQGTSVTVSS

SEQ ID NO: 23 - 8.16C10 CDRH1
GYTFTDYY

SEQ ID NO: 24 - 8.16C10 CDRH2
IYPGSGIT

SEQ ID NO: 25 - 8.16C10 CDRH3
AIYGYDGGYAMDY

SEQ ID NO: 26 - 8.16C10 Light chain nucleotide sequence
CAAATTGTTCTCACCCAGTCTCCAGCAATCATGTCTGCATCTCCTGGGGAGAAGGTCACCTTGACCTGCA
GTGCCAGCTCAAGTGTAAGTTCCAGCTACTTGTACTGGTATCAGCAGAAGCCAGGATCCTCCCCCAAACT
CTGGATTTATAGCACATCCAACCTGGCTTCTGGAGTCCCTGCTCGCTTCAGTGGCGGTGGGTCTGGGACC
TCTTACTCTCTCACAATCAGCAGCATGGAGGCTGAAGATGCTGCCTCTTATTTCTGCCATCAGTGGAGTA
CTTACCCGTACACGTTCGGAGGGGGGACCAAGCTGGAAATAAAGCG SEQ ID NO: 27 - 8.16C10 Light chain protein sequence
QIVLTQSPAIMSASPGEKVTLTCSASSSVSSSYLYWYQQKPGSSPKLWIYSTSNLASGVPARFSGGGSGT
SYSLTISSMEAEDAASYFCHQWSTYPYTEGGGTKLEIKR

SEQ ID NO: 28 - 8.16C10 CDRL1
SSVSSSY

SEQ ID NO: 29 - 8.16C10 CDRL2
STS

SEQ ID NO: 30 - 8.16C10 CDRL3
HQWSTYPYT

SEQ ID NO: 31 - 27.2H4 (D2.1) Heavy chain nucleotide sequence
GGCCTGAACAGGGCCTGGAGTGGATTGGATGGATTGATCCTGAGACTGGTAATACTATATATGACCCGAA
GTTCCAGGGCAAGGCCAGTATAACAGCTGACACATCCTCCAGCACAGCCTACCTGCAGCTCAACAGCCTG
ACATCTGAGGACACTGCCGTCTATTGCTGTGCTAGAGGCTGGTCCTATGCTATGGACTACTGGGGTCAAG
GAACCTCAGTCATCGTCTCCTCA SEQ ID NO: 32 - 27.2H4 (D2.1) Heavy chain protein sequence
EVQLQQSGAELVRPGALVKLSCKASGFNIKHYYIHWVNQRPEQGLEWIGWIDPETGNTIYDPKFQGKASI
TADTSSSTAYLQLNSLTSEDTAVYCCARGWSYAMDYWGQGTSVIVSS

SEQ ID NO: 33 - 27.2H4 (D2.1) CDRH1
GFNIKHYY

SEQ ID NO: 34 - 27.2H4 (D2.1) CDRH2
IDPETGNT

SEQ ID NO: 35 - 27.2H4 (D2.1) CDRH3
ARGWSYAMDY

SEQ ID NO: 36 - 27.2H4 (D2.1) Light chain nucleotide sequence
GACATTGTGATGACCCAGTCTCACAAATTCATGTCCACATCAGTAGGAGACAGGGTCAGCATCACCTGCA
AGGCCAGTCAGGATGTGAATACTGCTGTAGCCTGGTATCAACAGAAACCAGGACATTCTCCTAAACTACT
GATTTACTCGGCATCCTACCACTACACTGGAGTCCCTGATCGCTTCACTGGCAGTGGATCTGGGACGGAT
TTCACTTTCACCATCAGCAGTGTGCAGGCTGAAGACCTGGCAGTTTATTACTGTCAGCAACATTATAGTA
CTCCGTGGACGTTCGGTGGAGGCACCAAGCTGGAAATCAAAC SEQ ID NO: 37 - 27.2H4 (D2.1) Light chain protein sequence
DIVMTQSHKFMSTSVGDRVSITCKASQDVNTAVAWYQQKPGHSPKLLIYSASYHYTGVPDRFTGSGSGTD
FTFTISSVQAEDLAVYYCQQHYSTPWTFGGGTKLEIK

SEQ ID NO: 38 - 27.2H4 (D2.1) CDRL1
QDVNTA

SEQ ID NO: 39 - 27.2H4 (D2.1) CDRL2
SAS

SEQ ID NO: 40 - 27.2H4 (D2.1) CDRL3
QQHYSTPWT

SEQ ID NO: 41 - 27.12A6 (D2.2) Heavy chain nucleotide sequence
GAAGTGAAGCTGGTGGAGTCTGGGGGAGGTTTAGTGCAGCCTGGAGGGTCCCTGAATCTCTCCTGTGCAG
CCTCTGGATTCACTTTCAGTAGCTATACCATGTCTTGGGTTCGCCAGACTCCAGAGAAGAGGCTGGAGTG
GTCGCATACATTAGTAGTGGTGGTTATAGCACCTACTTTCCAGACACTGTAAAGGGCCGATTCACCATC
TCCAGAGACAATGCCAAGAACACCCTGTACCTGCAGATGAGCAGTCTGAAGTCTGAGGACACGGCCGTGT
ATTACTGTGCAAGAGGGGGGTATGGTAACTACGGGCCCTACTATAATATGGACTACTGGGGTCAAGGAAC
CTCAGTCACCGTCTCCTCA

```
SEQ ID NO: 42 - 27.12A6 (D2.2) Heavy chain protein sequence
EVKLVESGGGLVQPGGSLNLSCAASGFTESSYTMSWVRQTPEKRLEWVAYISSGGHSTYFPDTVKGRFTI
SRDNAKNTLYLQMSSLKSEDTAVYYCARGGYGNYGPYYNMDYWGQGTSVTVSS

SEQ ID NO: 43 - 27.12A6 (D2.2) CDRH1
GFTFSSYT

SEQ ID NO: 44 - 27.12A6 (D2.2) CDRH2
ISSGGHST

SEQ ID NO: 45 - 27.12A6 (D2.2) CDRH3
ARGGYGNYGPYYNMDY

SEQ ID NO: 46 - 27.12A6 (D2.2) Light chain nucleotide sequence
AACATTATGATGACACAGTCGCCATCATCTCTGGCTGTGTCTGCAGGAGAAAAGGTCACTATGAGCTGTA
AGTCCAGTCAAAGTGTTTTATACAGTTCAAATCAGAAGAACTACTTGGCCTGGTACCAGCAGAAACCAGG
GCAGTCTCCTAAATTGCTGATCTATTGGGCATCCACTAGGGAATCTGGTGTCCCTGATCGCTTCACAGGC
AGTGGATCTGGGACAGATTTTACTCTTACCATCAACAATGTACAAGCTGAAGACCTGGCAGTTTATTACT
GTCATCAATACCTCTCCTCGTGGACGTTCGGTGGAGGCACCAAGCTGGAAATCAAAC SEQ ID NO: 47 - 27.12A6 (D2.2) Light chain protein sequence
NIMMTQSPSSLAVSAGEKVTMSCKSSQSVLYSSNQKNYLAWYQQKPGQSPKLLIYWASTRESGVPDRFTG
SGSGTDFTLTINNVQAEDLAVYYCHQYLSSWTFGGGTKLEIK

SEQ ID NO: 48 - 27.12A6 (D2.2) CDRL1
QSVLYSSNQKNY

SEQ ID NO: 49 - 27.12A6 (D2.2) CDRL2
WAS

SEQ ID NO: 50 - 27.12A6 (D2.2) CDRL3
HQYLSSWT

SEQ ID NO: 51 - 6.14B9 (D2.3) Heavy chain nucleotide sequence
TCTGATGTGCAGCTTCAGGAGTCGGGACCTGGCCTGGTGAAACCTTCTCAGTCTCTGTCCCTCACCTGCA
CTGTCACTGGCTACTCAATCACCAGTGATTATGCCTGGAACTGGATCCGGCAGTTTCCAGGAAACAAACT
GGAGTGGATGGGCTACATAAGCTACAGTGGTAGTATTAGCTACAACCCATCTCTCAAAAGTCGAATCTCT
ATCACTCGAGACACATCCAAGAACCAGTTCTTCCTGCAGTTGAATTCTGTGACTACTGAGGACACAGCCA
CATATTACTGTGCAAGATCCGGGAGGTTACGACGGGACTTTGACTACTGGGGCCAAGGCACCACTCTCAC
A SEQ ID NO: 52 - 6.14B9 (D2.3) Heavy chain protein sequence
SDVQLQESGPGLVKPSQSLSLTCTVTGYSITSDYAWNWIRQFPGNKLEWMGYISYSGSISYNPSLKSRIS
ITRDTSKNQFFLQLNSVTTEDTATYYCARSGRLRRDFDYWGQGTTLT

SEQ ID NO: 53 - 6.14B9 (D2.3) CDRH1
GYSITSDYA

SEQ ID NO: 54 - 6.14B9 (D2.3) CDRH2
ISYSGSI

SEQ ID NO: 55 - 6.14B9 (D2.3) CDRH3
ARSGRLRRDFDY

SEQ ID NO: 56 - 6.14B9 (D2.3) Light chain nucleotide sequence
GACATCCAGATGACCCAGTCTCCATCCTCCTTATCTGCCTCTCTGGGAGAAAGAGTCAGTCTCACTTGTC
GGGCAAGTCAGGAAATTAGTGGTTACTTAAGTTGGCTTCAGCAGAAACCAGATGGAACTATTAAACGCCT
GATCTACGCCGCATCCACTTTAGATTCTGGTGTCCCAAAAAGGTTCAGTGGCAGTAGGTCTGGGTCAGAT
TATTCTCTCACCATCAGCAGCCTTGAGTCTGAAGATTTTGCAGACTATTACTGTCTACAATATGCTAGTT
ATCCTCTCACGTTCGGTGCTGGGACCAAGCTGGAGCTGAAAC SEQ ID NO: 57 - 6.14B9 (D2.3) Light chain protein sequence
DIQMTQSPSSLSASLGERVSLTCRASQEISGYLSWLQQKPDGTIKRLIYAASTLDSGVPKRFSGSRSGSD
YSLTISSLESEDFADYYCLQYASYPLTFGAGTKLELK

SEQ ID NO: 58 - 6.14B9 (D2.3) CDRL1
QEISGY

SEQ ID NO: 59 - 6.14B9 (D2.3) CDRL2
AAS

SEQ ID NO: 60 - 6.14B9 (D2.3) CDRL3
LQYASYPLT

SEQ ID NO: 61 - 6.16F9 (D2.4) Heavy chain nucleotide sequence
GAAGTGAACCTGGTGGAGTCTGGGGGAGGTTTAGTGCAGCCTGGAGGGTCCCTGAAACTCTCCTGTGCAG
CCTCTGGATTCACTTTCAGTAGCTATACCATGTCTTGGGTTCGCCAGAGTCCAGAGAAGAGGCTGGAGTG
GTCGCATACACTAGTAGTAGTGGTGCCAGCACCTACTATCCAGACACTGTAAAGGGCCGATTCACCATC
TCCAGAGACAATGCCAAGAACACCCTGCACCTGCAAATGAGTAGTCTCAAGTCTGAGGACACGGCCATGT
ATTACTGTGCAAGAGGGGGGTATGGTAACTACGGGCCCTACTATGCTTTGGACTACTGGGGTCAAGGAAC
CTCAGTCACCGTCTCCTCA
```

-continued

SEQ ID NO: 62 - 6.16F9 (D2.4) Heavy chain protein sequence
EVNLVESGGGLVQPGGSLKLSCAASGFTESSYTMSWVRQSPEKRLEWVAYTSSSGASTYYPDTVKGRFTI
SRDNAKNTLHLQMSSLKSEDTAMYYCARGGYGNYGPYYALDYWGQGTSVTVSS

SEQ ID NO: 63 - 6.16F9 (D2.4) CDRH1
GFTFSSYT

SEQ ID NO: 64 - 6.16F9 (D2.4) CDRH2
TSSSGAST

SEQ ID NO: 65 - 6.16F9 (D2.4) CDRH3
ARGGYGNYGPYYALDY

SEQ ID NO: 66 - 6.16F9 (D2.4) Light chain nucleotide sequence
AACATTATGATGACACAGTCGCCATCATCTCTGGCTGTGTCTGCAGGAGAAAAGGTCACTATGAGCTGTA
AGTCCAGTCAAAGTGTTTTATACAGTTCAAATCAGAAGAACTACTTGGCCTGGTACCAGCAGAAACCAGG
GCAGTCTCCTAAGCTGCTGATCTACTGGGCATCCACTAGGGAATCTGGTGTCCCTGATCGCTTCACAGGC
AGTGGATCTGAGACAGATTTTACTCTTACCATCAGCAGTGTACAAACTGAAGACCTGGCAGTTTATTACT
GTCATCAATACCTCTCCTCGTGGACGTTCGGTGGAGGCACCAAGCTGGAAATCAAAC SEQ ID NO: 67 - 6.16F9 (D2.4) Light chain protein sequence
NIMMTQSPSSLAVSAGEKVTMSCKSSQSVLYSSNQKNYLAWYQQKPGQSPKLLIYWASTRESGVPDRFTG
SGSETDFTLTISSVQTEDLAVYYCHQYLSSWTFGGGTKLEIK

SEQ ID NO: 68 - 6.16F9 (D2.4) CDRL1
QSVLYSSNQKNY

SEQ ID NO: 69 - 6.16F9 (D2.4) CDRL2
WAS

SEQ ID NO: 70 - 6.16F9 (D2.4) CDRL3
HQYLSSWT

SEQ ID NO: 71 - 33.1G12 Heavy chain nucleotide sequence
GAGGTTCAGTTGCAGCAGTCTGGACCTGAGCTGGTGAAGCCTGGGGCTTCAGTGAAGATATCCTGCAAGG
CTTCTGGTTACTCATTTACTGGCTACTTAATGAACTGGGTGATGCAGAGCCATGGAAAGAGTCTTGAGTG
GATTGGACGTATTAATCCTTACAATGGTGATATTTTCTACAACCAGAAGTTCAAGGACAAGGCCACATTG
ACTGTAGACAAATCCTCTAGTACAGCCCACATGGAGCTCCGGAGCCTGGCATCTGAGGACTCTGCAGTCT
ATTATTGTGCAAGAAGGGATGAGAACTTTGATTATGACAATGCTATGGACTACTGGGGTCAAGGAACCTC
AGTCACCG SEQ ID NO: 72 - 33.1G12 Heavy chain protein sequence
EVQLQQSGPELVKPGASVKISCKASGYSFTGYLMNWVMQSHGKSLEWIGRINPYNGDIFYNQKFKDKATL
TVDKSSSTAHMELRSLASEDSAVYYCARRDENFDYDNAMDYWGQGTSVT

SEQ ID NO: 73 - 33.1G12 CDRH1
GYSFTGYL

SEQ ID NO: 74 - 33.1G12 CDRH2
INPYNGDI

SEQ ID NO: 75 - 33.1G12 CDRH3
ARRDENFDYDNAMDY

SEQ ID NO: 76 - 33.1G12 Light chain nucleotide sequence
GACATTGTGCTGACCCAATCTCCAGCTTCTTTGGCTGTGTCTCTAGGGCAGAGGGCCACCATATCCTGCA
GAGCCAGTGAAAGTGTTGATATTTATGGCAATAGTTTTATGCACTGGTACCAGCAGAAACCAGGACAGCC
ACCCAAACTCCTCATCTATCGTGCGTCCAACCTAGAATCTGGGATCCCTGCCAGGTTCAGAGGCAGTGGG
TCTAGGACAGACTTCACCCTCACCATTTATCCTGTGGAGGCTGATGATGTTGCCACCTATTACTGTCAGC
AAAGTAATGAGGATCCGTGGACGTTCGGTGGAGGCACCAAGCTGGAAATCAAAC SEQ ID NO: 77 - 33.1G12 Light chain protein sequence
DIVLTQSPASLAVSLGQRATISCRASESVDIYGNSFMHWYQQKPGQPPKLLIYRASNLESGIPARFRGSG
SRTDFTLTIYPVEADDVATYYCQQSNEDPWTFGGGTKLEIK

SEQ ID NO: 78 - 33.1G12 CDRL1
ESVDIYGNSF

SEQ ID NO: 79 - 33.1G12 CDRL2
RAS

SEQ ID NO: 80 - 33.1G12 CDRL3
QQSNEDPWT

SEQ ID NO: 81 - 33.2A5 Heavy chain nucleotide sequence
CAGGTCCAGCTTCAGCAGTCTGGGGCTGAACTGGCAAAACCTGGGGTCTCAGTGAAGATGTCCTGCAAGG
CTTCTGGCTACACCTCTAATTATAACTGGATACATTGGATAAAACAGAGGCCTGGACAGGGTCTGGAATG
GATTGGATACATTAATCCTGCCACTGGTTATACTGACTACAATCAGAAGTTCAGGGACAAGGTCACATTG
ACTGCAGACAAATCCTCCAGCACAGCCTACATGCAACTGAGTAGTCTGACATCTGAGGACTCTGCACTCT
ATTACTGTACAACAGGGAGGAACGACGAGGGGGGCTATGCTCTGGACTCCTGGGGTCAAGGAACCTCAGT
CACCGTCTCCTCA -continued SEQ ID NO: 82 - 33.2A5 Heavy chain protein sequence
QVQLQQSGAELAKPGVSVKMSCKASGYTSNYNWIHWIKQRPGQGLEWIGYINPATGYTDYNQKFRDKVTL
TADKSSSTAYMQLSSLTSEDSALYYCTTGRNDEGGYALDSWGQGTSVTVSS

SEQ ID NO: 83 - 33.2A5 CDRH1
GYTSNYNW

SEQ ID NO: 84 - 33.2A5 CDRH2
INPATGYT

SEQ ID NO: 85 - 33.2A5 CDRH3
TTGRNDEGGYALDS

SEQ ID NO: 86 - 33.2A5 Light chain nucleotide sequence
GGCGTTGTGGTGACCCAATCTCCAACTTCTTTGGCTGTGTCTCTAGGGCAGAGGGCCACCATCTCCTGCA
AGGCCAGCCAAAGTGTTGATCATGCTGGTGATAGTTATATGAACTGGTACCAACAGAAAGCAGGGCAGCC
ACCCAAACTCCTCATCTATGGTGCATCCTATCTAGAATCTGTGATCCCAGGCAGGTTTAGTGGCAGTGGG
TCTGGGACAGACTTCACCCTCAACATCCATCCTGTGGAGGAGGAGGATGTTGCAACCTATTTCTGTCAGC
AAAGTAATGAGGATCCGTACACGTTCGGA SEQ ID NO: 87 - 33.2A5 Light chain protein sequence
GVVVTQSPTSLAVSLGQRATISCKASQSVDHAGDSYMNWYQQKAGQPPKLLIYGASYLESVIPGRFSGSG
SGTDFTLNIHPVEEEDVATYFCQQSNEDPYTFG

SEQ ID NO: 88 - 33.2A5 CDRL1
QSVDHAGDSY

SEQ ID NO: 89 - 33.2A5 CDRL2
GAS

SEQ ID NO: 90 - 33.2A5 CDRL3
QQSNEDPYT

SEQ ID NO: 91 - 33.14A5 (D1.5-1) Heavy chain nucleotide sequence
CAGGTCCAACTGCAGCAGTCTGGGCCTGAGCTGGTGAGGCCTGGGCCTTCAATGAGGATGTCCTGCAAGG
CTTCAGGCTATACCTTCACCAGCTACTGGATGTACTGGGTGAAAAAGAGGCCTGGACAAGGCCTTGAATG
GATTGGCATGATTGATCCTTCCAAGAGTGAAACTAGGTTAAATCAGAAGTGCGAGGACAAGGCCACATTG
AATGGAGAGAAAGCCTCCAACACAGCCTACATGGAGGTCAGCAGCCTGACATCTGATGACTCTGCAGTCC
ATTACTGTGCCCAGTATGGTAACCACGTCCTTTTGCTAACTGGGGCCAAGGGACACCGGTCACTGTCTCT
GCA SEQ ID NO: 92 - 33.14A5 (D1.5-1) Heavy chain protein sequence
QVQLQQSGPELVRPGPSMRMSCKASGYTFTSYWMYWVKKRPGQGLEWIGMIDPSKSETRLNQKCEDKATL
NGEKASNTAYMEVSSLTSDDSAVHYCAQYGNHVLLLTGAKGHRSLSLH

SEQ ID NO: 93 - 33.14A5 (D1.5-1) CDRH1
GYTFTSYW

SEQ ID NO: 94 - 33.14A5 (D1.5-1) CDRH2
IDPSKSET

SEQ ID NO: 95 - 33.14A5 (D1.5-1) CDRH3
AQYGNHVLLLTGAKGHRSLSLH

SEQ ID NO: 96 - 33.14A5 (D1.5-1) Light chain nucleotide sequence
GAAAATGTGCTCACCCAGTCTCCAGCAATCATGTCTGCATCTCCAGGGGAAAAGGTCACCATGACCTGCA
GGGCCAGCTCAAGTGTGAGTTCCAATTACTTGCACTGGTACCAGCAGAAGTCAGGTGCCTCCCCCAAACT
CTGGATTTATAGCACATCCAACTTGGCTTCTGGAGTCCCTGATCGCTTCAGGGGCAGTGGGTCTGGGACC
TCTTACTCTCTCACAATCACCAGTGTGGAGGCTGAAGATGCTGCCACTTACTACTGCCAGCTGTACAGTG
GTTACCCACTCACGTTCGGTGCTGGGACCAAGCTGGAGCTGAAAC SEQ ID NO: 97 - 33.14A5 (D1.5-1) Light chain protein sequence
ENVLTQSPAIMSASPGEKVTMTCRASSSVSSNYLHWYQQKSGASPKLWIYSTSNLASGVPDRERGSGSGT
SYSLTITSVEAEDAATYYCQLYSGYPLTFGAGTKLELK

SEQ ID NO: 98 - 33.14A5 (D1.5-1) CDRL1
SSVSSNY

SEQ ID NO: 99 - 33.14A5 (D1.5-1) CDRL2
STS

SEQ ID NO: 100 - 33.14A5 (D1.5-1) CDRL3
QLYSGYPLT

SEQ ID NO: 101 - 27.12E12 Heavy chain nucleotide sequence
GAGGTTCAGCTGCAGCAGTCTGGGGCTGAGCTTGTGAGGCCAGGGGCCTTAGTCAAGTTGTCCTGCAAAG
CTTCTGGCTTCAACATTAAAGACTACTATATGTATTGGATGAAGCAGAGGCCTGAACAGGGCCTGGAGTG
GATTGGATGGATTGATCCTGAGAATGTTAAGACTATATATGACCCGAAGTTCCAGGGCAGGGCCACTTTA
ACAGCAGACACATCCTCCAACACAGCCTACCTGCAGCTCAGCAGCCTGACATCTGAGGACACTGCCGTCT
ATTACTGTACTAGGGACTTCGGCTACGTTGGGTTCTTCGATGTCTGGGGCGCAGGGACCACGGTCACCGT
CTCCTCA SEQ ID NO: 102 - 27.12E12 Heavy chain protein sequence
EVQLQQSGAELVRPGALVKLSCKASGENIKDYYMYWMKQRPEQGLEWIGWIDPENVKTIYDPKFQGRATL
TADTSSNTAYLQLSSLTSEDTAVYYCTRDFGYVGFFDVWGAGTTVTVSS

SEQ ID NO: 103 - 27.12E12 CDRH1
GFNIKDYY

SEQ ID NO: 104 - 27.12E12 CDRH2
IDPENVKT

SEQ ID NO: 105 - 27.12E12 CDRH3
TRDFGYVGFFDV

SEQ ID NO: 106 - 27.12E12 Light chain nucleotide sequence
GACATTGTGATGACCCAGTCTCAAAAATTCATGTCCACATCAGTAGGAGACAGGGTCAGCGTCAATTGTA
AGGCCAGTCAGAATGTGGGTACTAATGTAGTCTGGTATCAACAGAAACCAGGGCAATCTCCTAAAGCACT
GATTTACTCGGCATCCTACCGGTACAGTGGAGTCCCTGATCGCTTCACAGGCAGTGGATCTGGGACAGAT
TTCACTCTCACCATCAGCACTGTGCAGTCTGAAGACTTGGCAGAATATTTCTGTCAGCAATATAACAGCT
ATCCTCTAACGTTCGGAGGGGGGACCAAGCTGGAAATAAAACG SEQ ID NO: 107 - 27.12E12 Light chain protein sequence
DIVMTQSQKFMSTSVGDRVSVNCKASQNVGTNVVWYQQKPGQSPKALIYSASYRYSGVPDRFTGSGSGTD
FTLTISTVQSEDLAEYFCQQYNSYPLTEGGGTKLEIKR

SEQ ID NO: 108 - 27.12E12 CDRL1
QNVGTN

SEQ ID NO: 109 - 27.12E12 CDRL2
SAS

SEQ ID NO: 110 - 27.12E12 CDRL3
QQYNSYPLT

SEQ ID NO: 111 - 9.1G12 Heavy chain nucleotide sequence
GAAGTGATGCTGGTGGAGTCTGGGGGAGGCTTAGTGAAGCCTGGAGGGTCCCTGAAACTCTCCTGTGCAG
CCTCTGGATTCACTTTCAGTAGCTATGCCATGTCTTGGGTTCGCCAGACTCCGGAGAGGAAGCTGGAGTG
GGTCGCAACCATTAGTAGTGGTGGTACTTATACCTACTATCCAGACAGTGTGAAGGGGCGATTCACCATC
TCCAGAGACAATGCCAAGAACCGCCTGTACCTGCAAATGAGCGGTCTGAGGTCTGAGGGCACGGCCATGT
ATTACTGTGTAAGACCTGACTATACTCACGACGACGGCGGTTTTGCTTACTGGGGCCAAGGGACTCTGGT
CACTGTCTCTGCA SEQ ID NO: 112 - 9.1G12 Heavy chain protein sequence
EVMLVESGGGLVKPGGSLKLSCAASGFTFSSYAMSWVRQTPERKLEWVATISSGGTYTYYPDSVKGRFTI
SRDNAKNRLYLQMSGLRSEGTAMYYCVRPDYTHDDGGFAYWGQGTLVTVSA

SEQ ID NO: 113 - 9.1G12 CDRH1
GFTFSSYA

SEQ ID NO: 114 - 9.1G12 CDRH2
ISSGGTYT

SEQ ID NO: 115 - 9.1G12 CDRH3
VRPDYTHDDGGFAY

SEQ ID NO: 116 - 9.1G12 Light Chain nucleotide sequence
CAGGCTGTTGTGACTCAGGAATCTGCACTCACCACATCACCTGGTGAAACAGTCACACTCACTTGTCGCT
CAAGTACTGGGGCTGTTACAACTAGTAACTATGCCAACTGGGTCCAAGAAAAACCAGATCATTTATTCAC
TGGTCTAATAGGTGGTACCAACAACCGAGCTCCAGGTGTTCCTGCCAGATTCTCAGGCTCCCTGATTGGA
GACAAGGCTGCCCTCACCATCACAGGGGCACAGACTGAGGATGAGGCAATATATTTCTGTGCTCTATGGT
ACAGCAACCATTGGGTGTTCGGTGGAGGAACCAAACTGACTGTCCTAG SEQ ID NO: 117 - 9.1G12 Light Chain protein sequence
QAVVTQESALTTSPGETVTLTCRSSTGAVTTSNYANWVQEKPDHLFTGLIGGTNNRAPGVPARFSGSLIG
DKAALTITGAQTEDEAIYFCALWYSNHWVFGGGTKLTVL

SEQ ID NO: 118 - 9.1G12 CDRL1
QGISNN

SEQ ID NO: 119 - 9.1G12 CDRL2
DAS

SEQ ID NO: 120 - 9.1G12 CDRL3
LQHRYLPHVRCW

SEQ ID NO: 121 - Human TIM3 coding sequence
GCTCAGTGGGGCGGCTACTGCTCATGTGATTGTGGAGTAGACAGTTGGAAGAAGTACCCAGTCCATTTG
GAGAGAGTTAAAACTGTGCCTAACAGAGGTGTCCTCTGACTTTTCTTCTGCAAGCTCCATGTTTTCACATCT
TCCCTTTGACTGTGTCCTGCTGCTGCTGCTACTACTTACAAGGTCCTCAGAAGTGGAATACAGAGCG
GAGGTCGGTCAGAATGCCTATCTGCCCTGCTTCTACACCCCAGCCGCCCAGGGAACCTCGTGCCCGTCT
GCTGGGGCAAAGGAGCCTGTCCTGTGTTTGAATGTGGCAACGTGGTGCTCAGGACTGATGAAAGGGATGT
GAATTATTGGACATCCAGATACTGGCTAAATGGGGATTTCCGCAAAGGAGATGTGTCCCTGACCATAGAG -continued

```
AATGTGATTCTAGCAGACAGTGGGATCTACTGCTGCCGGATCCAAATCCCAGGCATAATGAATGATGAAA
AATTTAACCTGAAGTTGGTCATCAAACCAGCCAAGGTCACCCCTGCACCGACTCTGCAGAGAGACTTCAC
TGCAGCCTTTCCAAGGATGCTTACCACCAGGGGACATGGCCCAGCAGAGACACAGACACTGGGGAGCCTC
CCTGATATAAATCTAACACAAATATCCACATTGGCCAATGAGTTACGGGACTCTAGATTGGCCAATGACT
TACGGGACTCTGGAGCAACCATCAGAATAGGCATCTACATCGGAGCAGGGATCTGTGCTGGGCTGGCTCT
GGCTCTTATCTTCGGCGCTTTAATTTTCAAATGGTATTCTCATAGCAAAGAAGATACAGAATTTAAGC
CTCATCTCTTTGGCCAACCTCCCTCCCTCAGGATTGGCAAATGCAGTAGCAGAGGGAATTCGCTCAGAAG
AAAACATCTATACCATTGAAGAGAACGTATATGAAGTGGAGGAGCCCAATGAGTATTATTGCTATGTCAG
CAGCAGGCAGCAACCCTCACAACCTTTGGGTTGTCGCTTTGCAATGCCATAGATCCAACCACCTTATTTT
TGAGCTTGGTGTTTTGTCTTTTTCAGAAACTATGAGCTGTGTCACCTGACTGGTTTTGGAGGTTCTGTCC
ACTGCTATGGAGCAGAGTTTTCCCATTTTCAGAAGATAATGACTCACATGGGAATTGAACTGGGACCTGC
ACTGAACTTAAACAGGCATGTCATTGCCTCTGTATTTAAGCCAACAGAGTTACCCAACCCAGAGACTGTT
AATCATGATGTTAGAGCTCAAACGGGCTTTTATATACACTAGGAATTCTTGACGTGGGGTCTCTGGAGC
TCCAGGAAATTCGGGCACATCATATGTCCATGAAACTTCAGATAAACTAGGGAAAACTGGGTGCTGAGGT
GAAAGCATAACTTTTTTGGCACAGAAAGTCTAAAGGGGCCACTGATTTTCAAAGAGATCTGTGATCCCTT
TTTGTTTTTTGTTTTTGAGATGGAGTCTTGCTCTGTTGCCCAGGCTGGAGTGCAATGGCACAATCTCGGC
TCACTGCAAGCTCCGCCTCCTGGGTTCAAGCGATTCTCCTGCCTCAGCCTCCTGAGTGGCTGGGATTACA
GGCATGCACCACCATGCCCAGCTAATTTGTTGTATTTTTAGTAGAGACAGGGTTTCACCATGTTGGCCAG
TGTGGTCTCAAACTCCTGACCTCATGATTTGCCTGCCTCGGCCTCCCAAAGCACTGGGATTACAGGCGTG
AGCCACCACATCCAGCCAGTGATCCTTAAAAGATTAAGAGATGACTGGACTAGGTCTACCTTGATCTTGA
AGATTCCCTTGGAATGTTGAGATTTAGGCTTATTTGAGCACTACCTGCCCAACTGTCAGTGCCAGTGCAT
AGCCCTTCTTTTGTCTCCCTTATGAAGACTGCCCTGCAGGGCTGAGATGTGGCAGGAGCTCCCAGGGAAA
AAGGAAGTGCATTTGATTGGTGTGTATTGGCCAAGTTTTGCTTGTTGTGTGCTTGAAAGAAAATATCTCT
GACCAACTTCTGTATTCGTGGACCAAACTGAAGCTATATTTTTCACAGAAGAAGAAGCAGTGACGGGGAC
ACAAATTCTGTTGCCTGGTGGAAAGAAGGCAAAGGCCTTCAGCAATCTATATTACCAGCGCTGGATCCTT
TGACAGAGAGTGGTCCCTAAACTTAAATTTCAAGACGGTATAGGCTTGATCTGTCTTGCTTATTGTTGCC
CCCTGCGCCTAGCACAATTTTGACACACAATTGGAACTTACTAAAAATTTTTTTTACTGTTAAAAAAAA
AAAAAAAAAA

SEQ ID NO: 122 - Human TIM3 protein sequence
MFSHLPFDCVLLLLLLLTRSSEVEYRAEVGQNAYLPCFYTPAAPGNLVPVCWGKGACPVFECGNVVLRT
DERDVNYWTSRYWLNGDFRKGDVSLTIENVTLADSGIYCCRIQIPGIMNDEKFNLKLVIKPAKVTPAPTR
QRDFTAAFPRMLTTRGHGPAETQTLGSLPDINLTQISTLANELRDSRLANDLRDSGATIRIGIYIGAGIC
AGLALALIFGALIFKWYSHSKEKIQNLSLISLANLPPSGLANAVAEGIRSEENIYTIEENVYEVEEPNEY
YCYVSSRQQPSQPLGCRFAMP
```

---

What is claimed is:

1. An antibody that specifically binds the extracellular domain of human T-cell Immunoglobulin Mucin (TIM) 3, wherein said binding results in internalization into a TIM3-expressing cell, and wherein the antibody is selected from the group consisting of
    (i) an antibody having light chain complementarity determining region (CDR) sequences of SEQ ID NOs:8-10 and heavy chain CDR sequences of SEQ ID NOs:3-5;
    (ii) an antibody having light chain CDR sequences of SEQ ID NOs:18-20 and heavy chain CDR sequences of SEQ ID NOs:13-15;
    (iii) an antibody having light chain CDR sequences of SEQ ID NOs:28-30 and heavy chain CDR sequences of SEQ ID NOs:23-25;
    (iv) an antibody having light chain CDR sequences of SEQ ID NOs:108-110 and heavy chain CDR sequences of SEQ ID NOs:103-105; and
    (v) an antibody having light chain CDR sequences of SEQ ID NOs:118-120 and heavy chain CDR sequences of SEQ ID NOs:113-115.

2. The antibody of claim 1, wherein said TIM3-expressing cells are acute myeloid leukemia (AML) cells.

3. The antibody of claim 1, wherein the TIM3-expressing cells are B lymphoma cells.

4. The antibody of claim 1, wherein the antibody has light chain complementarity determining region (CDR) sequences of SEQ ID NOs:8-10 and heavy chain CDR sequences of SEQ ID NOs:3-5.

5. The antibody of claim 1, wherein the antibody has light chain CDR sequences of SEQ ID NOs:18-20 and heavy chain CDR sequences of SEQ ID NOs:13-15.

6. The antibody of claim 1, wherein the antibody has light chain CDR sequences of SEQ ID NOs:28-30 and heavy chain CDR sequences of SEQ ID NOs:23-25.

7. The antibody of claim 1, wherein the antibody has light chain CDR sequences of SEQ ID NOs:108-110 and heavy chain CDR sequences of SEQ ID NOs:103-105.

8. The antibody of claim 1, wherein the antibody has light chain CDR sequences of SEQ ID NOs:118-120 and heavy chain CDR sequences of SEQ ID NOs: 113-115.

9. The antibody of claim 1, wherein said antibody is cross-linked or multimerized.

10. The antibody of claim 1, wherein the antibody is a chimeric antibody.

11. The antibody of claim 1, wherein the antibody is a humanized antibody.

12. A pharmaceutical composition comprising the antibody of claim 1.

* * * * *

SEQUENCE LISTING

```
<160> NUMBER OF SEQ IDS: 122

<210> SEQ ID NO 1
<211> LENGTH: 366
<212> TYPE: DNA
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 1.7E10
      heavy chain

<400> SEQUENCE: 1
gaggtgaagc ttctcgagtc tggaggtggc ctggtgcagc ctggaggatc cctgaaactc      60
tcctgtgcag cctcaggatt cgattttagt agatactgga tgagttgggt ccggcaggct    120
ccagggaaag ggctagaatg gattggagaa attaatccag atagcagtac gataaactat    180
acgccatctc taaggataa attcatcatc tccagagaca acgccaaaaa tacgctgttc     240
ctgcaaatga gcaaagtgag atctgaggac acagcccttt attactgtgc aagaccgagc    300
tatgatggtt actacgggta tgctatggac tactggggtc aaggaacctc agtcaccgtc    360
tcctca                                                               366

<210> SEQ ID NO 2
<211> LENGTH: 122
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 1.7E10
      heavy chain
```

```
<400> SEQUENCE: 2

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Phe
65                  70                  75                  80

Leu Gln Met Ser Lys Val Arg Ser Glu Asp Thr Ala Leu Tyr Tyr Cys
                85                  90                  95

Ala Arg Pro Ser Tyr Asp Gly Tyr Tyr Gly Tyr Ala Met Asp Tyr Trp
            100                 105                 110

Gly Gln Gly Thr Ser Val Thr Val Ser Ser
        115                 120

<210> SEQ ID NO 3
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 1.7E10
      heavy chain CDRH1

<400> SEQUENCE: 3

Gly Phe Asp Phe Ser Arg Tyr Trp
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 1.7E10
      heavy chain CDRH2

<400> SEQUENCE: 4

Ile Asn Pro Asp Ser Ser Thr Ile
1               5

<210> SEQ ID NO 5
<211> LENGTH: 15
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 1.7E10
      heavy chain CDRH3

<400> SEQUENCE: 5

Ala Arg Pro Ser Tyr Asp Gly Tyr Tyr Gly Tyr Ala Met Asp Tyr
1               5                   10                  15

<210> SEQ ID NO 6
<211> LENGTH: 335
<212> TYPE: DNA
<213> ORGANISM: Artificial Sequence
```

<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 1.7E10
      light chain

<400> SEQUENCE: 6

```
gacattgtac tgacccaatc tccagcttct ttggctgtgt ctctagggca gagggccacc      60
atatcctgca gagccagtga agtgttgat agttatggca agagtttat gcactggtac      120 cagcagaaac aggacagcc acccaaactc ctcatctatc gtgcatccaa cctagaatct      180
gggatccctg ccaggttcag tggcagtggg tctaggacag acttcaccct caccattaat      240
cctgtggagg ctgatgatgt tgcaacctat tactgtcagc aaagtaatga ggatccgtac      300
acgttcggag gggggaccaa gctggaaata aaacg                                335
```

<210> SEQ ID NO 7
<211> LENGTH: 112
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 1.7E10
      light chain

<400> SEQUENCE: 7

```
Asp Ile Val Leu Thr Gln Ser Pro Ala Ser Leu Ala Val Ser Leu Gly
  1               5                  10                  15

Gln Arg Ala Thr Ile Ser Cys Arg Ala Ser Glu Ser Val Asp Ser Tyr
             20                  25                  30

Gly Lys Ser Phe Met His Trp Tyr Gln Gln Lys Pro Gly Gln Pro Pro
         35                  40                  45

Lys Leu Leu Ile Tyr Arg Ala Ser Asn Leu Glu Ser Gly Ile Pro Ala
     50                  55                  60

Arg Phe Ser Gly Ser Gly Ser Arg Thr Asp Phe Thr Leu Thr Ile Asn
 65                  70                  75                  80

Pro Val Glu Ala Asp Asp Val Ala Thr Tyr Tyr Cys Gln Gln Ser Asn
                 85                  90                  95

Glu Asp Pro Tyr Thr Phe Gly Gly Gly Thr Lys Leu Glu Ile Lys Arg
            100                 105                 110
```

<210> SEQ ID NO 8
<211> LENGTH: 10
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 1.7E10
      light chain CDRL1

<400> SEQUENCE: 8

```
Glu Ser Val Asp Ser Tyr Gly Lys Ser Phe
  1               5                  10
```

<210> SEQ ID NO 9
<211> LENGTH: 3
<212> TYPE: PRT
<213> ORGANISM: Artificial Sequence

```
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 1.7E10
      light chain CDRL2

<400> SEQUENCE: 9

Arg Ala Ser
1

<210> SEQ ID NO 10
<211> LENGTH: 9
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 1.7E10
      light chain CDRL3

<400> SEQUENCE: 10

Gln Gln Ser Asn Glu Asp Pro Tyr Thr
1               5

<210> SEQ ID NO 11
<211> LENGTH: 351
<212> TYPE: DNA
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 7.10F6
      heavy chain

<400> SEQUENCE: 11
gaggtgcagc tggtggagtc tggggggaggc ttagtgcagc ctggagggtc cctgaagctc        60
tcctgtgcag cctctggatt catttttcagt ggctatggca tgtcttgggt tcgccagact      120
ccagacaaga ggctggagtt ggtcgcaatc attaatagca atggtggtag tgttgattat      180
ccagacagtg tgaagggccg agtcaccatc tccagagaca atgccaagaa cacctgtac      240 ctgcaaatga gcagtctgaa gtctgaggac acagccatgt attactgtgc aagaatctac      300
tatagatgta tggactactg gggtcaagga acctcagtca ccgtctcctc a                351

<210> SEQ ID NO 12
<211> LENGTH: 117
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 7.10F6
      heavy chain

<400> SEQUENCE: 12

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Gly Tyr
            20                  25                  30

Gly Met Ser Trp Val Arg Gln Thr Pro Asp Lys Arg Leu Glu Leu Val
        35                  40                  45

Ala Ile Ile Asn Ser Asn Gly Gly Ser Val Asp Tyr Pro Asp Ser Val
    50                  55                  60

Lys Gly Arg Val Thr Ile Ser Arg Asp Asn Ala Lys Asn Thr Leu Tyr
65                  70                  75                  80
```

```
Leu Gln Met Ser Ser Leu Lys Ser Glu Asp Thr Ala Met Tyr Tyr Cys
             85                  90                  95

Ala Arg Ile Tyr Tyr Arg Cys Met Asp Tyr Trp Gly Gln Gly Thr Ser
        100                 105                 110

Val Thr Val Ser Ser
        115

<210> SEQ ID NO 13
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 7.10F6
      heavy chain CDRH1

<400> SEQUENCE: 13

Gly Phe Ile Phe Ser Gly Tyr Gly
1               5

<210> SEQ ID NO 14
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 7.10F6
      heavy chain CDRH2

<400> SEQUENCE: 14

Ile Asn Ser Asn Gly Gly Ser Val
1               5

<210> SEQ ID NO 15
<211> LENGTH: 10
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 7.10F6
      heavy chain CDRH3

<400> SEQUENCE: 15

Ala Arg Ile Tyr Tyr Arg Cys Met Asp Tyr
1               5                   10

<210> SEQ ID NO 16
<211> LENGTH: 338
<212> TYPE: DNA
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 7.10F6
      light chain

<400> SEQUENCE: 16
aacattatga tgacacagtc gccatcatct ctggctgtgt ctgcaggaga aaaggtcact      60
atgagttgta agtccagtca aagtctttta tacagttcaa atcagaagaa ctacttggcc     120
tggtaccagc aaaaaccagg acagtctcct aaattgctga tctactgggc ttccgctagg     180
gaatctggtg tccctgatcg cttcacaggc ggtggatctg gacagattt tactcttacc      240
```

```
atcagcagtg tacaagctga agacctggca gtttattact gtcatcaata cctctcctcg    300
tacacgttcg gagggggggac caagctggag ataaaacg                            338
```

<210> SEQ ID NO 17
<211> LENGTH: 113
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 7.10F6
      light chain

<400> SEQUENCE: 17

```
Asn Ile Met Met Thr Gln Ser Pro Ser Ser Leu Ala Val Ser Ala Gly
 1               5                  10                  15

Glu Lys Val Thr Met Ser Cys Lys Ser Ser Gln Ser Leu Leu Tyr Ser
             20                  25                  30

Ser Asn Gln Lys Asn Tyr Leu Ala Trp Tyr Gln Gln Lys Pro Gly Gln
         35                  40                  45

Ser Pro Lys Leu Leu Ile Tyr Trp Ala Ser Ala Arg Glu Ser Gly Val
     50                  55                  60

Pro Asp Arg Phe Thr Gly Gly Gly Ser Gly Thr Asp Phe Thr Leu Thr
 65                  70                  75                  80

Ile Ser Ser Val Gln Ala Glu Asp Leu Ala Val Tyr Tyr Cys His Gln
                 85                  90                  95

Tyr Leu Ser Ser Tyr Thr Phe Gly Gly Gly Thr Lys Leu Glu Ile Lys
            100                 105                 110

Arg
```

<210> SEQ ID NO 18
<211> LENGTH: 12
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 7.10F6
      light chain CDRL1

<400> SEQUENCE: 18

```
Gln Ser Leu Leu Tyr Ser Ser Asn Gln Lys Asn Tyr
 1               5                  10
```

<210> SEQ ID NO 19
<211> LENGTH: 3
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 7.10F6
      light chain CDRL2

<400> SEQUENCE: 19

```
Trp Ala Ser
 1
```

<210> SEQ ID NO 20
<211> LENGTH: 8
<212> TYPE: PRT
<213> ORGANISM: Artificial Sequence

```
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 7.10F6
      light chain CDRL3

<400> SEQUENCE: 20

His Gln Tyr Leu Ser Ser Tyr Thr
 1               5

<210> SEQ ID NO 21
<211> LENGTH: 360
<212> TYPE: DNA
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 8.16C10
      heavy chain

<400> SEQUENCE: 21
cagatccagc tgcagcagtc tggacctgag ctggtgaagc ctggggcttc agtgaagata     60
tcctacaagg cttctggcta caccttcact gactactata aaactgggt gaagcagaag    120 cctggacagg gacttgagtg gattggatgg atttatcctg gaagcggtat tactaagtac    180
aatgagaagt tcaagggcaa ggccacattg actgtagact catcctccag cacagcctac    240
atgcagctca gcagcctgac atctgaggac actgctgtct atttctgtgc gatatatggt    300
tacgacgggg gatatgctat ggactactgg ggtcaaggaa cctcagtcac cgtctcctca    360

<210> SEQ ID NO 22
<211> LENGTH: 120
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 8.16C10
      heavy chain

<400> SEQUENCE: 22

Gln Ile Gln Leu Gln Gln Ser Gly Pro Glu Leu Val Lys Pro Gly Ala
 1               5                  10                  15

Ser Val Lys Ile Ser Tyr Lys Ala Ser Gly Tyr Thr Phe Thr Asp Tyr
                20                  25                  30

Tyr Ile Asn Trp Val Lys Gln Lys Pro Gly Gln Gly Leu Glu Trp Ile
            35                  40                  45

Gly Trp Ile Tyr Pro Gly Ser Gly Ile Thr Lys Tyr Asn Glu Lys Phe
        50                  55                  60

Lys Gly Lys Ala Thr Leu Thr Val Asp Ser Ser Ser Ser Thr Ala Tyr
65                  70                  75                  80

Met Gln Leu Ser Ser Leu Thr Ser Glu Asp Thr Ala Val Tyr Phe Cys
                85                  90                  95

Ala Ile Tyr Gly Tyr Asp Gly Gly Tyr Ala Met Asp Tyr Trp Gly Gln
                100                 105                 110

Gly Thr Ser Val Thr Val Ser Ser
        115                 120

<210> SEQ ID NO 23
<211> LENGTH: 8
<212> TYPE: PRT
<213> ORGANISM: Artificial Sequence
```

<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 8.16C10
      heavy chain CDRH1

<400> SEQUENCE: 23

Gly Tyr Thr Phe Thr Asp Tyr Tyr
1               5

<210> SEQ ID NO 24
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 8.16C10
      heavy chain CDRH2

<400> SEQUENCE: 24

Ile Tyr Pro Gly Ser Gly Ile Thr
1               5

<210> SEQ ID NO 25
<211> LENGTH: 13
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 8.16C10
      heavy chain CDRH3

<400> SEQUENCE: 25

Ala Ile Tyr Gly Tyr Asp Gly Gly Tyr Ala Met Asp Tyr
1               5                   10

<210> SEQ ID NO 26
<211> LENGTH: 326
<212> TYPE: DNA
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 8.16C10
      light chain

<400> SEQUENCE: 26
caaattgttc tcacccagtc tccagcaatc atgtctgcat ctcctgggga gaaggtcacc      60
ttgacctgca gtgccagctc aagtgtaagt tccagctact tgtactggta tcagcagaag    120
ccaggatcct cccccaaact ctggatttat agcacatcca acctggcttc tggagtccct    180
gctcgcttca gtggcggtgg gtctgggacc tcttactctc tcacaatcag cagcatggag    240
gctgaagatg ctgcctctta tttctgccat cagtggagta cttacccgta cacgttcgga    300
gggggaccca agctggaaat aaagcg                                          326

<210> SEQ ID NO 27
<211> LENGTH: 109
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 8.16C10
      light chain -continued

<400> SEQUENCE: 27

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Val Ser Ser Ser
            20                  25                  30

Tyr Leu Tyr Trp Tyr Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Gly Gly Ser Gly Thr Ser Tyr Ser Leu Thr Ile Ser Ser Met Glu
65              70                  75                  80

Ala Glu Asp Ala Ala Ser Tyr Phe Cys His Gln Trp Ser Thr Tyr Pro
                85                  90                  95

Tyr Thr Phe Gly Gly Gly Thr Lys Leu Glu Ile Lys Arg
            100                 105

<210> SEQ ID NO 28
<211> LENGTH: 7
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 8.16C10
      light chain CDRL1

<400> SEQUENCE: 28

Ser Ser Val Ser Ser Ser Tyr
1               5

<210> SEQ ID NO 29
<211> LENGTH: 3
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 8.16C10
      light chain CDRL2

<400> SEQUENCE: 29

Ser Thr Ser
1

<210> SEQ ID NO 30
<211> LENGTH: 9
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 8.16C10
      light chain CDRL3

<400> SEQUENCE: 30

His Gln Trp Ser Thr Tyr Pro Tyr Thr
1               5

<210> SEQ ID NO 31
<211> LENGTH: 233
<212> TYPE: DNA
<213> ORGANISM: Artificial Sequence
<220> FEATURE:
<223> OTHER INFORMATION: synthetic anti-T cell immunoglobulin- and mucin
domain-containing molecule 3 (TIM3, HAVCR2, KIM-3,
TIMD3, and FLJ14428) monoclonal antibody 27.2H4
(D2.1) heavy chain

<400> SEQUENCE: 31

```
ggcctgaaca gggcctggag tggattggat ggattgatcc tgagactggt aatactatat    60
atgacccgaa gttccagggc aaggccagta taacagctga cacatcctcc agcacagcct   120
acctgcagct caacagcctg acatctgagg acactgccgt ctattgctgt gctagaggct   180
ggtcctatgc tatggactac tggggtcaag gaacctcagt catcgtctcc tca           233
```

<210> SEQ ID NO 32
<211> LENGTH: 117
<212> TYPE: PRT
<213> ORGANISM: Artificial Sequence
<220> FEATURE:
<223> OTHER INFORMATION: synthetic anti-T cell immunoglobulin- and mucin
domain-containing molecule 3 (TIM3, HAVCR2, KIM-3,
TIMD3, and FLJ14428) monoclonal antibody 27.2H4
(D2.1) heavy chain

<400> SEQUENCE: 32

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys His Tyr
            20                  25                  30

Tyr Ile His Trp Val Asn Gln Arg Pro Glu Gln Gly Leu Glu Trp Ile
        35                  40                  45

Gly Trp Ile Asp Pro Glu Thr Gly Asn Thr Ile Tyr Asp Pro Lys Phe
    50                  55                  60

Gln Gly Lys Ala Ser Ile Thr Ala Asp Thr Ser Ser Ser Thr Ala Tyr
65                  70                  75                  80

Leu Gln Leu Asn Ser Leu Thr Ser Glu Asp Thr Ala Val Tyr Cys Cys
                85                  90                  95

Ala Arg Gly Trp Ser Tyr Ala Met Asp Tyr Trp Gly Gln Gly Thr Ser
            100                 105                 110

Val Ile Val Ser Ser
        115

<210> SEQ ID NO 33
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
domain-containing molecule 3 (TIM3, HAVCR2, KIM-3,
TIMD3, and FLJ14428) monoclonal antibody 27.2H4
(D2.1) heavy chain CDRH1

<400> SEQUENCE: 33

Gly Phe Asn Ile Lys His Tyr Tyr
1               5

<210> SEQ ID NO 34
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
domain-containing molecule 3 (TIM3, HAVCR2, KIM-3,
TIMD3, and FLJ14428) monoclonal antibody 27.2H4
(D2.1) heavy chain CDRH2

```
<400> SEQUENCE: 34

Ile Asp Pro Glu Thr Gly Asn Thr
1               5

<210> SEQ ID NO 35
<211> LENGTH: 10
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.2H4
      (D2.1) heavy chain CDRH3

<400> SEQUENCE: 35

Ala Arg Gly Trp Ser Tyr Ala Met Asp Tyr
1               5                   10

<210> SEQ ID NO 36
<211> LENGTH: 322
<212> TYPE: DNA
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.2H4
      (D2.1) light chain

<400> SEQUENCE: 36
gacattgtga tgacccagtc tcacaaattc atgtccacat cagtaggaga cagggtcagc     60
atcacctgca aggccagtca ggatgtgaat actgctgtag cctggtatca acagaaacca   120
ggacattctc ctaaactact gatttactcg gcatcctacc actacactgg agtccctgat   180
cgcttcactg gcagtggatc tgggacggat ttcactttca ccatcagcag tgtgcaggct   240
gaagacctgg cagtttatta ctgtcagcaa cattatagta ctccgtggac gttcggtgga   300
ggcaccaagc tggaaatcaa ac                                             322

<210> SEQ ID NO 37
<211> LENGTH: 107
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.2H4
      (D2.1) light chain

<400> SEQUENCE: 37

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Tyr His Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
                100                 105
```

<210> SEQ ID NO 38
<211> LENGTH: 6
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.2H4
      (D2.1) light chain CDRL1

<400> SEQUENCE: 38

Gln Asp Val Asn Thr Ala
 1               5

<210> SEQ ID NO 39
<211> LENGTH: 3
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.2H4
      (D2.1) light chain CDRL2

<400> SEQUENCE: 39

Ser Ala Ser
 1

<210> SEQ ID NO 40
<211> LENGTH: 9
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.2H4
      (D2.1) light chain CDRL3

<400> SEQUENCE: 40

Gln Gln His Tyr Ser Thr Pro Trp Thr
 1               5

<210> SEQ ID NO 41
<211> LENGTH: 369
<212> TYPE: DNA
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12A6
      (D2.2) heavy chain

<400> SEQUENCE: 41
gaagtgaagc tggtggagtc tgggggaggt ttagtgcagc ctggagggtc cctgaatctc      60
tcctgtgcag cctctggatt cactttcagt agctatacca tgtcttgggt tcgccagact     120
ccagagaaga ggctggagtg gtcgcatac attagtagtg gtggtcatag cacctacttt     180
ccagacactg taaagggccg attcaccatc tccagagaca atgccaagaa caccctgtac     240
ctgcagatga gcagtctgaa gtctgaggac acggccgtgt attactgtgc aagaggggg     300 tatggtaact acgggcccta ctataatatg gactactggg gtcaaggaac ctcagtcacc     360
gtctcctca                                                             369

<210> SEQ ID NO 42
<211> LENGTH: 123
<212> TYPE: PRT
<213> ORGANISM: Artificial Sequence

```
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12A6
      (D2.2) heavy chain

<400> SEQUENCE: 42

Glu Val Lys Leu Val Glu Ser Gly Gly Gly Leu Val Gln Pro Gly Gly
1               5                   10                  15

Ser Leu Asn Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Tyr Ile Ser Ser Gly Gly His Ser Thr Tyr Phe Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Val Tyr Tyr Cys
                85                  90                  95

Ala Arg Gly Gly Tyr Gly Asn Tyr Gly Pro Tyr Tyr Asn Met Asp Tyr
            100                 105                 110

Trp Gly Gln Gly Thr Ser Val Thr Val Ser Ser
        115                 120

<210> SEQ ID NO 43
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12A6
      (D2.2) heavy chain CDRH1

<400> SEQUENCE: 43

Gly Phe Thr Phe Ser Ser Tyr Thr
1               5

<210> SEQ ID NO 44
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12A6
      (D2.2) heavy chain CDRH2

<400> SEQUENCE: 44

Ile Ser Ser Gly Gly His Ser Thr
1               5

<210> SEQ ID NO 45
<211> LENGTH: 16
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12A6
      (D2.2) heavy chain CDRH3

<400> SEQUENCE: 45

Ala Arg Gly Gly Tyr Gly Asn Tyr Gly Pro Tyr Tyr Asn Met Asp Tyr
1               5                   10                  15
```

<210> SEQ ID NO 46
<211> LENGTH: 337
<212> TYPE: DNA
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12A6
      (D2.2) light chain

<400> SEQUENCE: 46
aacattatga tgacacagtc gccatcatct ctggctgtgt ctgcaggaga aaaggtcact      60
atgagctgta agtccagtca aagtgtttta tacagttcaa atcagaagaa ctacttggcc    120
tggtaccagc agaaaccagg gcagtctcct aaattgctga tctattgggc atccactagg    180
gaatctggtg tccctgatcg cttcacaggc agtggatctg ggacagattt tactcttacc    240
atcaacaatg tacaagctga agacctggca gtttattact gtcatcaata cctctcctcg    300
tggacgttcg gtggaggcac caagctggaa atcaaac                             337

<210> SEQ ID NO 47
<211> LENGTH: 112
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12A6
      (D2.2) light chain

<400> SEQUENCE: 47

Asn Ile Met Met Thr Gln Ser Pro Ser Ser Leu Ala Val Ser Ala Gly
 1               5                  10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Asn Asn Val Gln Ala Glu Asp Leu Ala Val Tyr Tyr Cys His Gln
                85                  90                  95

Tyr Leu Ser Ser Trp Thr Phe Gly Gly Gly Thr Lys Leu Glu Ile Lys
            100                 105                 110

<210> SEQ ID NO 48
<211> LENGTH: 12
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12A6
      (D2.2) light chain CDRL1

<400> SEQUENCE: 48

Gln Ser Val Leu Tyr Ser Ser Asn Gln Lys Asn Tyr
 1               5                  10

<210> SEQ ID NO 49
<211> LENGTH: 3
<212> TYPE: PRT
<213> ORGANISM: Artificial Sequence

```
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12A6
      (D2.2) light chain CDRL2

<400> SEQUENCE: 49

Trp Ala Ser
1

<210> SEQ ID NO 50
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12A6
      (D2.2) light chain CDRL3

<400> SEQUENCE: 50

His Gln Tyr Leu Ser Ser Trp Thr
1               5

<210> SEQ ID NO 51
<211> LENGTH: 351
<212> TYPE: DNA
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 6.14B9
      (D2.3) heavy chain

<400> SEQUENCE: 51
tctgatgtgc agcttcagga gtcgggacct ggcctggtga aaccttctca gtctctgtcc      60
ctcacctgca ctgtcactgg ctactcaatc accagtgatt atgcctggaa ctggatccgg     120
cagtttccag gaaacaaact ggagtggatg ggctacataa gctacagtgg tagtattagc     180
tacaacccat ctctcaaaag tcgaatctct atcactcgag acacatccaa gaaccagttc     240
ttcctgcagt tgaattctgt gactactgag gacacagcca catattactg tgcaagatcc     300
gggaggttac gacgggactt tgactactgg ggccaaggca ccactctcac a              351

<210> SEQ ID NO 52
<211> LENGTH: 117
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 6.14B9
      (D2.3) heavy chain

<400> SEQUENCE: 52

Ser Asp Val Gln Leu Gln Glu Ser Gly Pro Gly Leu Val Lys Pro Ser
1               5                   10                  15

Gln Ser Leu Ser Leu Thr Cys Thr Val Thr Gly Tyr Ser Ile Thr Ser
            20                  25                  30

Asp Tyr Ala Trp Asn Trp Ile Arg Gln Phe Pro Gly Asn Lys Leu Glu
        35                  40                  45

Trp Met Gly Tyr Ile Ser Tyr Ser Gly Ser Ile Ser Tyr Asn Pro Ser
    50                  55                  60

Leu Lys Ser Arg Ile Ser Ile Thr Arg Asp Thr Ser Lys Asn Gln Phe
65                  70                  75                  80
```

```
Phe Leu Gln Leu Asn Ser Val Thr Thr Glu Asp Thr Ala Thr Tyr Tyr
                85                  90                  95

Cys Ala Arg Ser Gly Arg Leu Arg Arg Asp Phe Asp Tyr Trp Gly Gln
            100                 105                 110

Gly Thr Thr Leu Thr
        115
```

<210> SEQ ID NO 53
<211> LENGTH: 9
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 6.14B9
      (D2.3) heavy chain CDRH1

<400> SEQUENCE: 53

```
Gly Tyr Ser Ile Thr Ser Asp Tyr Ala
 1               5
```

<210> SEQ ID NO 54
<211> LENGTH: 7
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 6.14B9
      (D2.3) heavy chain CDRH2

<400> SEQUENCE: 54

```
Ile Ser Tyr Ser Gly Ser Ile
 1               5
```

<210> SEQ ID NO 55
<211> LENGTH: 12
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 6.14B9
      (D2.3) heavy chain CDRH3

<400> SEQUENCE: 55

```
Ala Arg Ser Gly Arg Leu Arg Arg Asp Phe Asp Tyr
 1               5                  10
```

<210> SEQ ID NO 56
<211> LENGTH: 322
<212> TYPE: DNA
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 6.14B9
      (D2.3) light chain

<400> SEQUENCE: 56

```
gacatccaga tgacccagtc tccatcctcc ttatctgcct ctctgggaga aagagtcagt    60
ctcacttgtc gggcaagtca ggaaattagt ggttacttaa gttggcttca gcagaaacca   120
gatggaacta ttaaacgcct gatctacgcc gcatccactt tagattctgg tgtcccaaaa   180
aggttcagtg gcagtaggtc tgggtcagat tattctctca ccatcagcag ccttgagtct   240
```

```
gaagattttg cagactatta ctgtctacaa tatgctagtt atcctctcac gttcggtgct    300
gggaccaagc tggagctgaa ac                                            322
```

<210> SEQ ID NO 57
<211> LENGTH: 107
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 6.14B9
      (D2.3) light chain

<400> SEQUENCE: 57

Asp Ile Gln Met Thr Gln Ser Pro Ser Ser Leu Ser Ala Ser Leu Gly
 1               5                  10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Leu
                85                  90                  95

Thr Phe Gly Ala Gly Thr Lys Leu Glu Leu Lys
            100                 105

<210> SEQ ID NO 58
<211> LENGTH: 6
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 6.14B9
      (D2.3) light chain CDRL1

<400> SEQUENCE: 58

Gln Glu Ile Ser Gly Tyr
 1               5

<210> SEQ ID NO 59
<211> LENGTH: 3
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 6.14B9
      (D2.3) light chain CDRL2

<400> SEQUENCE: 59

Ala Ala Ser
 1

<210> SEQ ID NO 60
<211> LENGTH: 9
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 6.14B9
      (D2.3) light chain CDRL3

<400> SEQUENCE: 60

Leu Gln Tyr Ala Ser Tyr Pro Leu Thr
 1               5

<210> SEQ ID NO 61
<211> LENGTH: 369
<212> TYPE: DNA
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 6.16F9
      (D2.4) heavy chain

<400> SEQUENCE: 61
gaagtgaacc tggtggagtc tgggggaggt ttagtgcagc ctggagggtc cctgaaactc      60
tcctgtgcag cctctggatt cactttcagt agctatacca tgtcttgggt tcgccagagt     120
ccagagaaga ggctggagtg ggtcgcatac actagtagta gtggtgccag cacctactat     180
ccagacactg taaagggccg attcaccatc tccagagaca atgccaagaa caccctgcac     240
ctgcaaatga gtagtctcaa gtctgaggac acggccatgt attactgtgc aagaggggggg    300 tatggtaact acgggcccta ctatgctttg gactactggg gtcaaggaac ctcagtcacc     360
gtctcctca                                                             369

<210> SEQ ID NO 62
<211> LENGTH: 123
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 6.16F9
      (D2.4) heavy chain

<400> SEQUENCE: 62

Glu Val Asn Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Ser Tyr
             20                  25                  30

Thr Met Ser Trp Val Arg Gln Ser Pro Glu Lys Arg Leu Glu Trp Val
         35                  40                  45

Ala Tyr Thr Ser Ser Ser Gly Ala Ser Thr Tyr Tyr Pro Asp Thr Val
     50                  55                  60

Lys Gly Arg Phe Thr Ile Ser Arg Asp Asn Ala Lys Asn Thr Leu His
 65                  70                  75                  80

Leu Gln Met Ser Ser Leu Lys Ser Glu Asp Thr Ala Met Tyr Tyr Cys
                 85                  90                  95

Ala Arg Gly Gly Tyr Gly Asn Tyr Gly Pro Tyr Tyr Ala Leu Asp Tyr
            100                 105                 110

Trp Gly Gln Gly Thr Ser Val Thr Val Ser Ser
            115                 120

<210> SEQ ID NO 63
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
domain-containing molecule 3 (TIM3, HAVCR2, KIM-3,
TIMD3, and FLJ14428) monoclonal antibody 6.16F9
(D2.4) heavy chain CDRH1

<400> SEQUENCE: 63

Gly Phe Thr Phe Ser Ser Tyr Thr
 1               5

<210> SEQ ID NO 64
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
domain-containing molecule 3 (TIM3, HAVCR2, KIM-3,
TIMD3, and FLJ14428) monoclonal antibody 6.16F9
(D2.4) heavy chain CDRH2

<400> SEQUENCE: 64

Thr Ser Ser Ser Gly Ala Ser Thr
 1               5

<210> SEQ ID NO 65
<211> LENGTH: 16
<212> TYPE: PRT
<213> ORGANISM: Artificial Sequence
<220> FEATURE:
<223> OTHER INFORMATION: synthetic anti-T cell immunoglobulin- and mucin
domain-containing molecule 3 (TIM3, HAVCR2, KIM-3,
TIMD3, and FLJ14428) monoclonal antibody 6.16F9
(D2.4) heavy chain CDRH3

<400> SEQUENCE: 65

Ala Arg Gly Gly Tyr Gly Asn Tyr Gly Pro Tyr Tyr Ala Leu Asp Tyr
 1               5                  10                  15

<210> SEQ ID NO 66
<211> LENGTH: 337
<212> TYPE: DNA
<213> ORGANISM: Artificial Sequence
<220> FEATURE:
<223> OTHER INFORMATION: synthetic anti-T cell immunoglobulin- and mucin
domain-containing molecule 3 (TIM3, HAVCR2, KIM-3,
TIMD3, and FLJ14428) monoclonal antibody 6.16F9
(D2.4) light chain

<400> SEQUENCE: 66
aacattatga tgacacagtc gccatcatct ctggctgtgt ctgcaggaga aaaggtcact      60
atgagctgta agtccagtca aagtgtttta tacagttcaa atcagaagaa ctacttggcc    120
tggtaccagc agaaaccagg gcagtctcct aagctgctga tctactgggc atccactagg    180
gaatctggtg tccctgatcg cttcacaggc agtggatctg agacagattt tactcttacc    240
atcagcagtg tacaaactga agacctggca gtttattact gtcatcaata cctctcctcg    300
tggacgttcg gtggaggcac caagctggaa atcaaac                             337

<210> SEQ ID NO 67
<211> LENGTH: 112
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 6.16F9
      (D2.4) light chain

<400> SEQUENCE: 67

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Glu Thr Asp Phe Thr Leu Thr
65                  70                  75                  80

Ile Ser Ser Val Gln Thr Glu Asp Leu Ala Val Tyr Tyr Cys His Gln
                85                  90                  95

Tyr Leu Ser Ser Trp Thr Phe Gly Gly Gly Thr Lys Leu Glu Ile Lys
            100                 105                 110

<210> SEQ ID NO 68
<211> LENGTH: 12
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 6.16F9
      (D2.4) light chain CDRL1

<400> SEQUENCE: 68

Gln Ser Val Leu Tyr Ser Ser Asn Gln Lys Asn Tyr
1               5                   10

<210> SEQ ID NO 69
<211> LENGTH: 3
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 6.16F9
      (D2.4) light chain CDRL2

<400> SEQUENCE: 69

Trp Ala Ser
1

<210> SEQ ID NO 70
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 6.16F9
      (D2.4) light chain CDRL3

<400> SEQUENCE: 70

His Gln Tyr Leu Ser Ser Trp Thr
1               5

<210> SEQ ID NO 71
<211> LENGTH: 358
<212> TYPE: DNA
<213> ORGANISM: Artificial Sequence
<220> FEATURE:
<223> OTHER INFORMATION: synthetic anti-T cell immunoglobulin- and mucin
domain-containing molecule 3 (TIM3, HAVCR2, KIM-3,
TIMD3, and FLJ14428) monoclonal antibody 33.1G12
heavy chain

<400> SEQUENCE: 71

```
gaggttcagt tgcagcagtc tggacctgag ctggtgaagc ctggggcttc agtgaagata      60
tcctgcaagg cttctggtta ctcatttact ggctacttaa tgaactgggt gatgcagagc     120
catggaaaga gtcttgagtg gattggacgt attaatcctt acaatggtga tattttctac     180
aaccagaagt tcaaggacaa ggccacattg actgtagaca atcctctag tacagcccac      240 atggagctcc ggagcctggc atctgaggac tctgcagtct attattgtgc aagaagggat     300
gagaactttg attatgacaa tgctatggac tactggggtc aaggaacctc agtcaccg      358
```

<210> SEQ ID NO 72
<211> LENGTH: 120
<212> TYPE: PRT
<213> ORGANISM: Artificial Sequence
<220> FEATURE:
<223> OTHER INFORMATION: synthetic anti-T cell immunoglobulin- and mucin
domain-containing molecule 3 (TIM3, HAVCR2, KIM-3,
TIMD3, and FLJ14428) monoclonal antibody 33.1G12
heavy chain

<400> SEQUENCE: 72

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Leu Met Asn Trp Val Met Gln Ser His Gly Lys Ser Leu Glu Trp Ile
        35                  40                  45

Gly Arg Ile Asn Pro Tyr Asn Gly Asp Ile Phe Tyr Asn Gln Lys Phe
    50                  55                  60

Lys Asp Lys Ala Thr Leu Thr Val Asp Lys Ser Ser Ser Thr Ala His
65                  70                  75                  80

Met Glu Leu Arg Ser Leu Ala Ser Glu Asp Ser Ala Val Tyr Tyr Cys
                85                  90                  95

Ala Arg Arg Asp Glu Asn Phe Asp Tyr Asp Asn Ala Met Asp Tyr Trp
            100                 105                 110

Gly Gln Gly Thr Ser Val Thr Leu
        115                 120
```

<210> SEQ ID NO 73
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
domain-containing molecule 3 (TIM3, HAVCR2, KIM-3,
TIMD3, and FLJ14428) monoclonal antibody 33.1G12
heavy chain CDRH1

<400> SEQUENCE: 73

```
Gly Tyr Ser Phe Thr Gly Tyr Leu
1               5
```

<210> SEQ ID NO 74
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.1G12
      heavy chain CDRH2

<400> SEQUENCE: 74

Ile Asn Pro Tyr Asn Gly Asp Ile
1               5

<210> SEQ ID NO 75
<211> LENGTH: 15
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.1G12
      heavy chain CDRH3

<400> SEQUENCE: 75

Ala Arg Arg Asp Glu Asn Phe Asp Tyr Asp Asn Ala Met Asp Tyr
1               5                   10                  15

<210> SEQ ID NO 76
<211> LENGTH: 334
<212> TYPE: DNA
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.1G12
      light chain

<400> SEQUENCE: 76
gacattgtgc tgacccaatc tccagcttct ttggctgtgt ctctagggca gagggccacc      60
atatcctgca gagccagtga agtgttgat atttatggca atagttttat gcactggtac     120
cagcagaaac aggacagcc acccaaactc ctcatctatc gtgcgtccaa cctagaatct     180
gggatccctg ccaggttcag aggcagtggg tctaggacag acttcaccct caccatttat     240
cctgtggagg ctgatgatgt tgccacctat tactgtcagc aaagtaatga ggatccgtgg     300
acgttcggtg gaggcaccaa gctggaaatc aaac                                 334

<210> SEQ ID NO 77
<211> LENGTH: 111
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.1G12
      light chain

<400> SEQUENCE: 77

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ile Tyr
            20                  25                  30

Gly Asn Ser Phe Met His Trp Tyr Gln Gln Lys Pro Gly Gln Pro Pro
        35                  40                  45

```
Lys Leu Leu Ile Tyr Arg Ala Ser Asn Leu Glu Ser Gly Ile Pro Ala
    50                  55                  60

Arg Phe Arg Gly Ser Gly Ser Arg Thr Asp Phe Thr Leu Thr Ile Tyr
65                  70                  75                  80

Pro Val Glu Ala Asp Asp Val Ala Thr Tyr Tyr Cys Gln Gln Ser Asn
                85                  90                  95

Glu Asp Pro Trp Thr Phe Gly Gly Gly Thr Lys Leu Glu Ile Lys
            100                 105                 110

<210> SEQ ID NO 78
<211> LENGTH: 10
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.1G12
      light chain CDRL1

<400> SEQUENCE: 78

Glu Ser Val Asp Ile Tyr Gly Asn Ser Phe
1               5                   10

<210> SEQ ID NO 79
<211> LENGTH: 3
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.1G12
      light chain CDRL2

<400> SEQUENCE: 79

Arg Ala Ser
1

<210> SEQ ID NO 80
<211> LENGTH: 9
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.1G12
      light chain CDRL3

<400> SEQUENCE: 80

Gln Gln Ser Asn Glu Asp Pro Trp Thr
1               5

<210> SEQ ID NO 81
<211> LENGTH: 363
<212> TYPE: DNA
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.2A5
      heavy chain

<400> SEQUENCE: 81
caggtccagc ttcagcagtc tggggctgaa ctggcaaaac ctggggtctc agtgaagatg      60
tcctgcaagg cttctggcta cacctctaat tataactgga cattggat aaaacagagg      120 cctggacagg gtctggaatg gattggatac attaatcctg ccactggtta tactgactac      180
```

-continued

```
aatcagaagt tcagggacaa ggtcacattg actgcagaca atcctccag cacagcctac    240 atgcaactga gtagtctgac atctgaggac tctgcactct attactgtac aacagggagg    300
aacgacgagg ggggctatgc tctggactcc tggggtcaag aacctcagt caccgtctcc    360 tca                                                                  363
```

<210> SEQ ID NO 82
<211> LENGTH: 121
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.2A5
      heavy chain

<400> SEQUENCE: 82

```
Gln Val Gln Leu Gln Gln Ser Gly Ala Glu Leu Ala Lys Pro Gly Val
 1               5                  10                  15

Ser Val Lys Met Ser Cys Lys Ala Ser Gly Tyr Thr Ser Asn Tyr Asn
            20                  25                  30

Trp Ile His Trp Ile Lys Gln Arg Pro Gly Gln Gly Leu Glu Trp Ile
        35                  40                  45

Gly Tyr Ile Asn Pro Ala Thr Gly Tyr Thr Asp Tyr Asn Gln Lys Phe
    50                  55                  60

Arg Asp Lys Val Thr Leu Thr Ala Asp Lys Ser Ser Ser Thr Ala Tyr
65                  70                  75                  80

Met Gln Leu Ser Ser Leu Thr Ser Glu Asp Ser Ala Leu Tyr Tyr Cys
                85                  90                  95

Thr Thr Gly Arg Asn Asp Glu Gly Gly Tyr Ala Leu Asp Ser Trp Gly
            100                 105                 110

Gln Gly Thr Ser Val Thr Val Ser Ser
        115                 120
```

<210> SEQ ID NO 83
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.2A5
      heavy chain CDRH

<400> SEQUENCE: 83

```
Gly Tyr Thr Ser Asn Tyr Asn Trp
 1               5
```

<210> SEQ ID NO 84
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.2A5
      heavy chain CDRH2

<400> SEQUENCE: 84

```
Ile Asn Pro Ala Thr Gly Tyr Thr
 1               5
```

<210> SEQ ID NO 85
<211> LENGTH: 14
<212> TYPE: PRT
<213> ORGANISM: Artificial Sequence
<220> FEATURE:
<223> OTHER INFORMATION: synthetic anti-T cell immunoglobulin- and mucin
domain-containing molecule 3 (TIM3, HAVCR2, KIM-3,
TIMD3, and FLJ14428) monoclonal antibody 33.2A5
heavy chain CDRH3

<400> SEQUENCE: 85

Thr Thr Gly Arg Asn Asp Glu Gly Gly Tyr Ala Leu Asp Ser
1               5                   10

<210> SEQ ID NO 86
<211> LENGTH: 309
<212> TYPE: DNA
<213> ORGANISM: Artificial Sequence
<220> FEATURE:
<223> OTHER INFORMATION: synthetic anti-T cell immunoglobulin- and mucin
domain-containing molecule 3 (TIM3, HAVCR2, KIM-3,
TIMD3, and FLJ14428) monoclonal antibody 33.2A5
light chain

<400> SEQUENCE: 86
ggcgttgtgg tgacccaatc tccaacttct ttggctgtgt ctctagggca gagggccacc      60
atctcctgca aggccagcca aagtgttgat catgctggtg atagttatat gaactggtac     120
caacagaaag cagggcagcc acccaaactc ctcatctatg gtgcatccta tctagaatct     180
gtgatcccag gcaggtttag tggcagtggg tctgggacag acttcaccct caacatccat     240
cctgtggagg aggaggatgt tgcaacctat ttctgtcagc aaagtaatga ggatccgtac     300
acgttcgga                                                             309

<210> SEQ ID NO 87
<211> LENGTH: 103
<212> TYPE: PRT
<213> ORGANISM: Artificial Sequence
<220> FEATURE:
<223> OTHER INFORMATION: synthetic anti-T cell immunoglobulin- and mucin
domain-containing molecule 3 (TIM3, HAVCR2, KIM-3,
TIMD3, and FLJ14428) monoclonal antibody 33.2A5
light chain

<400> SEQUENCE: 87

Gly Val Val Val Thr Gln Ser Pro Thr Ser Leu Ala Val Ser Leu Gly
1               5                   10                  15

Gln Arg Ala Thr Ile Ser Cys Lys Ala Ser Gln Ser Val Asp His Ala
            20                  25                  30

Gly Asp Ser Tyr Met Asn Trp Tyr Gln Gln Lys Ala Gly Gln Pro Pro
        35                  40                  45

Lys Leu Leu Ile Tyr Gly Ala Ser Tyr Leu Glu Ser Val Ile Pro Gly
    50                  55                  60

Arg Phe Ser Gly Ser Gly Ser Gly Thr Asp Phe Thr Leu Asn Ile His
65                  70                  75                  80

Pro Val Glu Glu Glu Asp Val Ala Thr Tyr Phe Cys Gln Gln Ser Asn
                85                  90                  95

Glu Asp Pro Tyr Thr Phe Gly
            100

<210> SEQ ID NO 88
<211> LENGTH: 10
<212> TYPE: PRT
<213> ORGANISM: Artificial Sequence

```
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.2A5
      light chain CDRL1

<400> SEQUENCE: 88

Gln Ser Val Asp His Ala Gly Asp Ser Tyr
1               5                   10

<210> SEQ ID NO 89
<211> LENGTH: 3
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.2A5
      light chain CDRL2

<400> SEQUENCE: 89

Gly Ala Ser
1

<210> SEQ ID NO 90
<211> LENGTH: 9
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.2A5
      light chain CDRL3

<400> SEQUENCE: 90

Gln Gln Ser Asn Glu Asp Pro Tyr Thr
1               5

<210> SEQ ID NO 91
<211> LENGTH: 353
<212> TYPE: DNA
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.14A5
      (D1.5-1) heavy chain

<400> SEQUENCE: 91
caggtccaac tgcagcagtc tgggcctgag ctggtgaggc ctgggccttc aatgaggatg     60
tcctgcaagg cttcaggcta taccttcacc agctactgga tgtactgggt gaaaagagg    120 cctggacaag gccttgaatg gattggcatg attgatcctt ccaagagtga aactaggtta   180
aatcagaagt gcgaggacaa ggccacattg aatggagaga agcctccaa cacagcctac   240 atggaggtca gcagcctgac atctgatgac tctgcagtcc attactgtgc ccagtatggt   300
aaccacgtcc ttttgctaac tggggccaag ggacaccggt cactgtctct gca          353

<210> SEQ ID NO 92
<211> LENGTH: 118
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.14A5
      (D1.5-1) heavy chain
```

```
<400> SEQUENCE: 92

Gln Val Gln Leu Gln Gln Ser Gly Pro Glu Leu Val Arg Pro Gly Pro
1               5                   10                  15

Ser Met Arg Met Ser Cys Lys Ala Ser Gly Tyr Thr Phe Thr Ser Tyr
            20                  25                  30

Trp Met Tyr Trp Val Lys Lys Arg Pro Gly Gln Gly Leu Glu Trp Ile
        35                  40                  45

Gly Met Ile Asp Pro Ser Lys Ser Glu Thr Arg Leu Asn Gln Lys Cys
    50                  55                  60

Glu Asp Lys Ala Thr Leu Asn Gly Glu Lys Ala Ser Asn Thr Ala Tyr
65                  70                  75                  80

Met Glu Val Ser Ser Leu Thr Ser Asp Asp Ser Ala Val His Tyr Cys
                85                  90                  95

Ala Gln Tyr Gly Asn His Val Leu Leu Leu Thr Gly Ala Lys Gly His
            100                 105                 110

Arg Ser Leu Ser Leu His
        115

<210> SEQ ID NO 93
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.14A5
      (D1.5-1) heavy chain CDRH1

<400> SEQUENCE: 93

Gly Tyr Thr Phe Thr Ser Tyr Trp
1               5

<210> SEQ ID NO 94
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.14A5
      (D1.5-1) heavy chain CDRH2

<400> SEQUENCE: 94

Ile Asp Pro Ser Lys Ser Glu Thr
1               5

<210> SEQ ID NO 95
<211> LENGTH: 22
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.14A5
      (D1.5-1) heavy chain CDRH3

<400> SEQUENCE: 95

Ala Gln Tyr Gly Asn His Val Leu Leu Leu Thr Gly Ala Lys Gly His
1               5                   10                  15

Arg Ser Leu Ser Leu His
            20
```

<210> SEQ ID NO 96
<211> LENGTH: 325
<212> TYPE: DNA
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.14A5
      (D1.5-1) light chain

<400> SEQUENCE: 96
gaaaatgtgc tcacccagtc tccagcaatc atgtctgcat ctccagggga aaaggtcacc      60
atgacctgca gggccagctc aagtgtgagt tccaattact tgcactggta ccagcagaag     120
tcaggtgcct cccccaaact ctggatttat agcacatcca acttggcttc tggagtccct     180
gatcgcttca gggcagtgg gtctgggacc tcttactctc tcacaatcac cagtgtggag      240
gctgaagatg ctgccactta ctactgccag ctgtacagtg gttacccact cacgttcggt     300
gctgggacca agctggagct gaaac                                            325

<210> SEQ ID NO 97
<211> LENGTH: 108
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.14A5
      (D1.5-1) light chain

<400> SEQUENCE: 97

Glu Asn Val Leu Thr Gln Ser Pro Ala Ile Met Ser Ala Ser Pro Gly
1               5                   10                  15

Glu Lys Val Thr Met Thr Cys Arg Ala Ser Ser Ser Val Ser Ser Asn
            20                  25                  30

Tyr Leu His Trp Tyr Gln Gln Lys Ser Gly Ala Ser Pro Lys Leu Trp
        35                  40                  45

Ile Tyr Ser Thr Ser Asn Leu Ala Ser Gly Val Pro Asp Arg Phe Arg
    50                  55                  60

Gly Ser Gly Ser Gly Thr Ser Tyr Ser Leu Thr Ile Thr Ser Val Glu
65                  70                  75                  80

Ala Glu Asp Ala Ala Thr Tyr Tyr Cys Gln Leu Tyr Ser Gly Tyr Pro
                85                  90                  95

Leu Thr Phe Gly Ala Gly Thr Lys Leu Glu Leu Lys
            100                 105

<210> SEQ ID NO 98
<211> LENGTH: 7
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.14A5
      (D1.5-1) light chain CDRL1

<400> SEQUENCE: 98

Ser Ser Val Ser Ser Asn Tyr
1               5

<210> SEQ ID NO 99
<211> LENGTH: 3
<212> TYPE: PRT
<213> ORGANISM: Artificial Sequence

```
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.14A5
      (D1.5-1) light chain CDRL2

<400> SEQUENCE: 99

Ser Thr Ser
 1

<210> SEQ ID NO 100
<211> LENGTH: 9
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 33.14A5
      (D1.5-1) light chain CDRL3

<400> SEQUENCE: 100

Gln Leu Tyr Ser Gly Tyr Pro Leu Thr
 1               5

<210> SEQ ID NO 101
<211> LENGTH: 357
<212> TYPE: DNA
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12E12
      heavy chain

<400> SEQUENCE: 101
gaggttcagc tgcagcagtc tggggctgag cttgtgaggc caggggcctt agtcaagttg      60
tcctgcaaag cttctggctt caacattaaa gactactata tgtattggat gaagcagagg     120
cctgaacagg gcctggagtg gattggatgg attgatcctg agaatgttaa gactatatat     180
gacccgaagt tccagggcag ggccacttta acagcagaca catcctccaa cacagcctac     240
ctgcagctca gcagcctgac atctgaggac actgccgtct attactgtac tagggacttc     300
ggctacgttg ggttcttcga tgtctggggc cagggacca cggtcaccgt ctcctca         357

<210> SEQ ID NO 102
<211> LENGTH: 119
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12E12
      heavy chain

<400> SEQUENCE: 102

Glu Val Gln Leu Gln Gln Ser Gly Ala Glu Leu Val Arg Pro Gly Ala
 1               5                  10                  15

Leu Val Lys Leu Ser Cys Lys Ala Ser Gly Phe Asn Ile Lys Asp Tyr
             20                  25                  30

Tyr Met Tyr Trp Met Lys Gln Arg Pro Glu Gln Gly Leu Glu Trp Ile
         35                  40                  45

Gly Trp Ile Asp Pro Glu Asn Val Lys Thr Ile Tyr Asp Pro Lys Phe
     50                  55                  60

Gln Gly Arg Ala Thr Leu Thr Ala Asp Thr Ser Ser Asn Thr Ala Tyr
65                  70                  75                  80
```

Leu Gln Leu Ser Ser Leu Thr Ser Glu Asp Thr Ala Val Tyr Tyr Cys
            85                  90                  95

Thr Arg Asp Phe Gly Tyr Val Gly Phe Phe Asp Val Trp Gly Ala Gly
            100                 105                 110

Thr Thr Val Thr Val Ser Ser
        115

<210> SEQ ID NO 103
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12E12
      heavy chain CDRH1

<400> SEQUENCE: 103

Gly Phe Asn Ile Lys Asp Tyr Tyr
1               5

<210> SEQ ID NO 104
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12E12
      heavy chain CDRH2

<400> SEQUENCE: 104

Ile Asp Pro Glu Asn Val Lys Thr
1               5

<210> SEQ ID NO 105
<211> LENGTH: 12
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12E12
      heavy chain CDRH3

<400> SEQUENCE: 105

Thr Arg Asp Phe Gly Tyr Val Gly Phe Phe Asp Val
1               5                   10

<210> SEQ ID NO 106
<211> LENGTH: 323
<212> TYPE: DNA
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12E12
      light chain

<400> SEQUENCE: 106
gacattgtga tgacccagtc tcaaaaattc atgtccacat cagtaggaga cagggtcagc      60
gtcaattgta aggccagtca gaatgtgggt actaatgtag tctggtatca acagaaacca     120
gggcaatctc ctaaagcact gatttactcg gcatcctacc ggtacagtgg agtccctgat     180
cgcttcacag gcagtggatc tgggacagat ttcactctca ccatcagcac tgtgcagtct     240

```
gaagacttgg cagaatattt ctgtcagcaa tataacagct atcctctaac gttcggaggg      300
gggaccaagc tggaaataaa acg                                              323
```

<210> SEQ ID NO 107
<211> LENGTH: 108
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12E12
      light chain

<400> SEQUENCE: 107

```
Asp Ile Val Met Thr Gln Ser Gln Lys Phe Met Ser Thr Ser Val Gly
1               5                   10                  15

Asp Arg Val Ser Val Asn Cys Lys Ala Ser Gln Asn Val Gly Thr Asn
            20                  25                  30

Val Val Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Thr Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Gly Gly Thr Lys Leu Glu Ile Lys Arg
            100                 105
```

<210> SEQ ID NO 108
<211> LENGTH: 6
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12E12
      light chain CDRL1

<400> SEQUENCE: 108

```
Gln Asn Val Gly Thr Asn
1               5
```

<210> SEQ ID NO 109
<211> LENGTH: 3
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12E12
      light chain CDRL2

<400> SEQUENCE: 109

```
Ser Ala Ser
1
```

<210> SEQ ID NO 110
<211> LENGTH: 9
<212> TYPE: PRT
<213> ORGANISM: Artificial Sequence

```
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 27.12E12
      light chain CDRL3

<400> SEQUENCE: 110

Gln Gln Tyr Asn Ser Tyr Pro Leu Thr
1               5

<210> SEQ ID NO 111
<211> LENGTH: 363
<212> TYPE: DNA
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 9.1G12
      heavy chain

<400> SEQUENCE: 111
gaagtgatgc tggtggagtc tggggggaggc ttagtgaagc ctggagggtc cctgaaactc      60
tcctgtgcag cctctggatt cactttcagt agctatgcca tgtcttgggt tcgccagact     120
ccggagagga agctggagtg ggtcgcaacc attagtagtg gtggtactta tacctactat     180
ccagacagtg tgaaggggcg attcaccatc tccagagaca atgccaagaa ccgcctgtac     240
ctgcaaatga gcggtctgag gtctgagggc acggccatgt attactgtgt aagacctgac     300
tatactcacg acgacggcgg ttttgcttac tggggccaag ggactctggt cactgtctct     360
gca                                                                   363

<210> SEQ ID NO 112
<211> LENGTH: 121
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 9.1G12
      heavy chain

<400> SEQUENCE: 112

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Arg Lys Leu Glu Trp Val
        35                  40                  45

Ala Thr Ile Ser Ser Gly Gly Thr Tyr Thr Tyr Tyr Pro Asp Ser Val
    50                  55                  60

Lys Gly Arg Phe Thr Ile Ser Arg Asp Asn Ala Lys Asn Arg Leu Tyr
65                  70                  75                  80

Leu Gln Met Ser Gly Leu Arg Ser Glu Gly Thr Ala Met Tyr Tyr Cys
                85                  90                  95

Val Arg Pro Asp Tyr Thr His Asp Asp Gly Gly Phe Ala Tyr Trp Gly
            100                 105                 110

Gln Gly Thr Leu Val Thr Val Ser Ala
        115                 120
```

<210> SEQ ID NO 113
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
domain-containing molecule 3 (TIM3, HAVCR2, KIM-3,
TIMD3, and FLJ14428) monoclonal antibody 9.1G12
heavy chain CDRH1

<400> SEQUENCE: 113

Gly Phe Thr Phe Ser Ser Tyr Ala
1               5

<210> SEQ ID NO 114
<211> LENGTH: 8
<212> TYPE: PRT
<213> ORGANISM: Artificial Sequence
<220> FEATURE:
<223> OTHER INFORMATION: synthetic anti-T cell immunoglobulin- and mucin
domain-containing molecule 3 (TIM3, HAVCR2, KIM-3,
TIMD3, and FLJ14428) monoclonal antibody 9.1G12
heavy chain CDRH2

<400> SEQUENCE: 114

Ile Ser Ser Gly Gly Thr Tyr Thr
1               5

<210> SEQ ID NO 115
<211> LENGTH: 14
<212> TYPE: PRT
<213> ORGANISM: Artificial Sequence
<220> FEATURE:
<223> OTHER INFORMATION: synthetic anti-T cell immunoglobulin- and mucin
domain-containing molecule 3 (TIM3, HAVCR2, KIM-3,
TIMD3, and FLJ14428) monoclonal antibody 9.1G12
heavy chain CDRH3

<400> SEQUENCE: 115

Val Arg Pro Asp Tyr Thr His Asp Asp Gly Gly Phe Ala Tyr
1               5                   10

<210> SEQ ID NO 116
<211> LENGTH: 328
<212> TYPE: DNA
<213> ORGANISM: Artificial Sequence
<220> FEATURE:
<223> OTHER INFORMATION: synthetic anti-T cell immunoglobulin- and mucin
domain-containing molecule 3 (TIM3, HAVCR2, KIM-3,
TIMD3, and FLJ14428) monoclonal antibody 9.1G12
light chain

<400> SEQUENCE: 116
caggctgttg tgactcagga atctgcactc accacatcac ctggtgaaac agtcacactc      60
acttgtcgct caagtactgg ggctgttaca actagtaact atgccaactg gtccaagaa     120 aaaccagatc atttattcac tggtctaata ggtggtacca caaccgagc tccaggtgtt     180 cctgccagat tctcaggctc cctgattgga acaaggctg ccctcaccat cacaggggca     240
cagactgagg atgaggcaat atatttctgt gctctatggt acagcaacca ttgggtgttc    300
ggtggaggaa ccaaactgac tgtcctag                                       328

<210> SEQ ID NO 117
<211> LENGTH: 109
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 9.1G12
      light chain

<400> SEQUENCE: 117

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105

<210> SEQ ID NO 118
<211> LENGTH: 6
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 9.1G12
      light chain CDRL1

<400> SEQUENCE: 118

Gln Gly Ile Ser Asn Asn
1               5

<210> SEQ ID NO 119
<211> LENGTH: 3
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 9.1G12
      light chain CDRL2

<400> SEQUENCE: 119

Asp Ala Ser
1

<210> SEQ ID NO 120
<211> LENGTH: 12
<212> TYPE: PRT
<213> ORGANISM: Artificial Sequence
<220> FEATURE:
<223> OTHER INFORMATION: synthetic anti-T cell immunoglobulin- and mucin
      domain-containing molecule 3 (TIM3, HAVCR2, KIM-3,
      TIMD3, and FLJ14428) monoclonal antibody 9.1G12
      light chain CDRL3

<400> SEQUENCE: 120

Leu Gln His Arg Tyr Leu Pro His Val Arg Cys Trp
1               5                   10

<210> SEQ ID NO 121
<211> LENGTH: 2320
<212> TYPE: DNA
<213> ORGANISM: Homo sapiens
<220> FEATURE:
<223> OTHER INFORMATION: human T cell immunoglobulin- and mucin
    domain-containing molecule 3 (TIM3, HAVCR2, KIM-3,
    TIMD3, and FLJ14428) coding sequence

<400> SEQUENCE: 121

```
gctcagtggg ggcggctact gctcatgtga ttgtggagta gacagttgga agaagtaccc      60
agtccatttg gagagttaaa actgtgccta acagaggtgt cctctgactt ttcttctgca     120
agctccatgt tttcacatct tccctttgac tgtgtcctgc tgctgctgct gctactactt     180
acaaggtcct cagaagtgga atacagagcg gaggtcggtc agaatgccta tctgccctgc     240
ttctacaccc cagccgcccc agggaacctc gtgcccgtct gctggggcaa aggagcctgt     300
cctgtgtttg aatgtggcaa cgtggtgctc aggactgatg aaagggatgt gaattattgg     360
acatccagat actggctaaa tgggattttc gcaaaggag atgtgtccct gaccatagag      420
aatgtgattc tagcagacag tgggatctac tgctgccgga tccaaatccc aggcataatg     480
aatgatgaaa aatttaacct gaagttggtc atcaaaccag ccaaggtcac ccctgcaccg     540
actctgcaga gagacttcac tgcagccttt ccaaggatgc ttaccaccag gggacatggc     600
ccagcagaga cacagacact ggggagcctc cctgatataa atctaacaca aatatccaca     660
ttggccaatg agttacggga ctctagattg gccaatgact acgggactc tggagcaacc     720
atcagaatag catctacat cggagcaggg atctgtgctg ggctggctct ggctcttatc     780
ttcggcgctt taatttttcaa atggtattct catagcaaag aagataca gaatttaagc     840
ctcatctctt tggccaacct ccctccctca ggattggcaa atgcagtagc agagggaatt     900
cgctcagaag aaaacatcta taccattgaa gagaacgtat atgaagtgga ggagcccaat     960
gagtattatt gctatgtcag cagcaggcag caaccctcac aaccctttgg gttgtcgcttt    1020
gcaatgccat agatccaacc accttatttt tgagcttggt gttttgtctt tttcagaaac    1080
tatgagctgt gtcacctgac tggttttgga ggttctgtcc actgctatgg agcagagttt    1140
tcccattttc agaagataat gactcacatg ggaattgaac tgggacctgc actgaactta    1200
aacaggcatg tcattgcctc tgtatttaag ccaacagagt tacccaaccc agagactgtt    1260
aatcatggat gttagagctc aaacgggctt ttatatacac taggaattct tgacgtgggg    1320
tctctggagc tccaggaaat tcgggcacat catatgtcca tgaaacttca gataaactag    1380
ggaaaactgg gtgctgaggt gaaagcataa cttttttggc acagaaagtc taaaggggcc    1440
actgattttc aaagagatct gtgatcccctt tttgttttttt gttttttgaga tggagtcttg    1500
ctctgttgcc caggctggag tgcaatggca caatctcggc tcactgcaag ctccgcctcc    1560
tgggttcaag cgattctcct gcctcagcct cctgagtggc tgggattaca ggcatgcacc    1620
accatgccca gctaatttgt tgtatttttta gtagagacag ggtttcacca tgttggccag    1680
tgtggtctca aactcctgac ctcatgattt gcctgcctcg gcctcccaaa gcactgggat    1740
tacaggcgtg agccaccaca tccagccagt gatccttaaa agattaagag atgactggac    1800
taggtctacc ttgatcttga agattccctt ggaatgttga gatttaggct tatttgagca    1860
ctacctgccc aactgtcagt gccagtgcat agcccttctt ttgtctccct tatgaagact    1920
gccctgcagg gctgagatgt ggcaggagct cccagggaaa aaggaagtgc atttgattgg    1980
tgtgtattgg ccaagttttg cttgttgtgt gcttgaaaga aatatctct gaccaacttc     2040
```

```
tgtattcgtg gaccaaactg aagctatatt tttcacagaa gaagaagcag tgacggggac  2100
acaaattctg ttgcctggtg gaaagaaggc aaaggccttc agcaatctat attaccagcg  2160
ctggatcctt tgacagagag tggtccctaa acttaaattt caagacggta taggcttgat  2220
ctgtcttgct tattgttgcc ccctgcgcct agcacaattt tgacacacaa ttggaactta  2280
ctaaaaattt tttttactg ttaaaaaaaa aaaaaaaaa                          2320
```

<210> SEQ ID NO 122
<211> LENGTH: 301
<212> TYPE: PRT
<213> ORGANISM: Homo sapiens
<220> FEATURE:
<223> OTHER INFORMATION: human T cell immunoglobulin- and mucin
      domain-containing molecule 3 (TIM3, HAVCR2, KIM-3,
      TIMD3, and FLJ14428)
<220> FEATURE:
<221> NAME/KEY: DOMAIN
<222> LOCATION: (22)...(202)
<223> OTHER INFORMATION: extracellular domain
<220> FEATURE:
<221> NAME/KEY: DOMAIN
<222> LOCATION: (203)...(223)
<223> OTHER INFORMATION: transmembrane domain
<220> FEATURE:
<221> NAME/KEY: DOMAIN
<222> LOCATION: (224)...(301)
<223> OTHER INFORMATION: cytoplasmic domain

<400> SEQUENCE: 122

Met Phe Ser His Leu Pro Phe Asp Cys Val Leu Leu Leu Leu Leu Leu
 1               5                  10                  15

Leu Leu Thr Arg Ser Ser Glu Val Glu Tyr Arg Ala Glu Val Gly Gln
             20                  25                  30

Asn Ala Tyr Leu Pro Cys Phe Tyr Thr Pro Ala Ala Pro Gly Asn Leu
         35                  40                  45

Val Pro Val Cys Trp Gly Lys Gly Ala Cys Pro Val Phe Glu Cys Gly
     50                  55                  60

Asn Val Val Leu Arg Thr Asp Glu Arg Asp Val Asn Tyr Trp Thr Ser
 65                  70                  75                  80

Arg Tyr Trp Leu Asn Gly Asp Phe Arg Lys Gly Asp Val Ser Leu Thr
                 85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

-continued

```
Ser Leu Ala Asn Leu Pro Pro Ser Gly Leu Ala Asn Ala Val Ala Glu
            245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300
```